United States Patent [19]

Johnson

[11] Patent Number: 5,753,446
[45] Date of Patent: May 19, 1998

[54] MITOGEN ERK KINASE KINASE (MEKK) ASSAY

[75] Inventor: Gary L. Johnson, Boulder, Colo.

[73] Assignee: National Jewish Center for Immunology & Respiratory Medicine, Denver, Colo.

[21] Appl. No.: 472,934

[22] Filed: Jun. 6, 1995

Related U.S. Application Data

[63] Continuation-in-part of Ser. No. 323,460, Oct. 14, 1994, and Ser. No. 440,421, May 12, 1995, which is a continuation-in-part of Ser. No. 354,516, Feb. 21, 1995, abandoned, which is a division of Ser. No. 49,254, filed as PCT/US94/11690 Oct. 14, 1994, published as WO95/28421 Oct. 26, 1995, and filed as PCT/US94/04178 Apr. 15, 1994, published as WO94/24159 Oct. 27, 1994, Pat. No. 5,405,941, said Ser. No. 323,460, is a continuation-in-part of Ser. No. 49,254.

[51] Int. Cl.$^6$ .................................................. G01N 33/53
[52] U.S. Cl. .................. 435/7.1; 435/69.1; 435/252.3; 435/320.1; 435/325; 530/300; 530/350; 536/23.1; 536/23.5
[58] Field of Search .................. 435/7.1, 69.1, 435/252.3, 320.1; 530/300, 350; 536/23.1, 23.5

[56] References Cited

U.S. PATENT DOCUMENTS

| 5,283,173 | 2/1994 | Fields et al. | 435/6 |
|---|---|---|---|
| 5,405,941 | 4/1995 | Johnson et al. | 530/350 |

FOREIGN PATENT DOCUMENTS

| WO 94/24159 | 10/1994 | WIPO . |
|---|---|---|
| WO 95/28421 | 10/1995 | WIPO . |

OTHER PUBLICATIONS

Marshall, C., "MAP Kinase Kinase Kinase, MAP Kinase Kinase and MAP Kinase," *Current Opinion in Genetics and Development*, vol. 4, 82–89 (1994).

Masuda, T., et al., "Protein Kinase Byr2 is a Target of Ras1 in the Fission Yeast *Schizosaccharomyces pombe,*" *The Journal of Biological Chemistry*, vol. 270, No. 5, 1979–1982 (1995).

Minden, A., et al., "Differential Activation of ERK and JNK Mitogen–Activated Protein Kinases by Raf–1 and MEKK," *Science*, vol. 266, 1719–1723 (1994).

Reuter, C., et al., "Biochemical Analysis of MEK Activation in NIH3T3 Fibroblasts," *The Journal of Biological Chemistry*, vol. 270, No. 13, 7644–7655 (1995).

Russell, M., et al., "Direct Interaction Betweeen Ras and the Kinase Domain of Mitogen–activated Protein Kinase Kinase Kinase (MEKK1)," *The Journal of Biological Chemistry*, vol. 270, No. 20, 11757–11760 (1995).

Sánchez, I., et al., "Role Of SAPK/ERK Kinase–1 in the Stress–Activated Pathway Regulating Transcription Factor c–Jun," *Nature*, vol. 372, 794–798 (1994).

Ueki, K., et al., "Feedback Regulation of Mitogen–activated Protein Kinase Kinase Kinase Activity Of c–Raf–1 by Insulin and Phorbol Ester Stimulation," *The Journal of Biological Chemistry*, vol. 269, No. 22, 15756–15761 (1994).

Whitehurst, C., et al., "The MEK Kinase Activity of the Catalytic Domain of Raf–1 is Regulated Independently of Ras Binding in T Cells," *The Journal of Biological Chemistry*, vol. 270, No. 10, 5594–5599 (1995).

Winston, B., et al., "Tumor Necrosis Factor α Rapidly Activates the Mitogen–Activated Protein Kinase (MAPK) Cascade in a MAPK Kinase Kinase–dependent, c–Raf–1–independent Fashion in Mouse Macrophages," *Proc. Natl. Acad. Sci. USA*, vol. 92, 1614–1618 (1995).

Yan, M., and Templeton, D., "Identification of 2 Serine Residues of MEK–1 that are Differentially Phosphorylated During Activation by raf and MEK Kinase," *The Journal of Biological Chemistry*, vol. 269, No. 29, 19067–19073 (1994).

Yan, M., et al., "Activation of Stress–Activated Protein Kinase by MEKK1 Phosphorylation of its Activator SEK1," *Nature*, vol. 372, 798–800 (1994).

Zheng, C. and Guan, K., "Activation of MEK Family Kinases Requires Phosphorylation of Two Conserved Ser/Thr Residues," *The EMBO Journal*, vol. 13, No. 5, 1123–1131 (1994).

Blumer, K., et al., "Mammalian Mitogen–Activated Protein Kinase Kinase Kinase (MEKK) can Function in a Yeast mitogen–Activated Protein Kinase Pathway Downstream of Protein Kinase C," *Proc. Natl. Acad. Sci. USA*, vol. 91, 4925–4929 (1994).

Büscher, D., et al., "Ras–Dependent and–Independent Pathways Target the Mitogen–Activated Protein Kinase Network in Macrophages," *Mol. Cell. Biol.*, vol. 15, 466–475 (1995).

Chaleff, D. and Tatchell, K., "Molecular Cloning and Characterization of the STE7 and STE11 Genes of *Saccharomyces cerevisiae,*" *Molecular and Cellular Biology*, vol. 5, 1878–1886 (1985).

Crews, C., et al., "The Primary Structure of MEK, a Protein Kinase that Phosphorylates the ERK Gene Product," *Science*, vol. 258, 478–480 (1992).

Dent, P., et al., "Activation of Mitogen–Activated Protein Kinase Kinase by v–Raf in NIH 3T3 Cells and in Vitro," *Science*, vol. 257, 1404–1407 (1992).

Dérijard, B., et al., "Independent Human MAP Kinase Signal Transduction Pathways Defined by MEK and MKK Isoforms," *Science*, vol. 267, 682–285 (1995).

(List continued on next page.)

*Primary Examiner*—Sephen Walsh
*Assistant Examiner*—Kenneth A. Sorensen
*Attorney, Agent, or Firm*—Lahive & Cockfield, LLP; Giulio A. DeConti, Jr.; Catherine J. Kara

[57] ABSTRACT

The present invention relates to isolated MEKK proteins, nucleic acid molecules having sequences that encode such proteins, and antibodies raised against such proteins. The present invention also includes methods useful for identifying compounds capable of specifically regulating signal transduction in cells expressing MEKK protein.

30 Claims, No Drawings

OTHER PUBLICATIONS

Gardner, A., et al., "MEK-1 Phosphorylation by MEK Kinase, Raf, and Mitogen–activated Protein Kinase: Analysis of Phosphopeptides and Regulation of Activity," *Molecular Biology of the Cell*, vol. 5, 193–201 (1994).

Kyriakis, J., et al., "Raf–1 Activates MAP Kinase–kinase," Nature, vol. 358, 417–421 (1992).

Lange–Carter, C. and Johnson, G., "Ras–Dependent Growth Factor Regulation of MEK Kinase in PC12 Cells," *Science*, vol. 265, 1458–1461 (1994).

Lange–Carter, C., et al., "A Divergence in the MAP Kinase Regulatory Network Defined by MEK Kinase and Raf," *Science*, vol. 260, 315–319 (1993).

Lin, A., et al., "Identification of a Dual Specificity Kinase that Activates the Jun Kinases and p38–Mpk2," *Science*, vol. 268, 286–290 (1995).

Wang et al., (1991) Molec. Cell. Biol. 11:3554–3563.

Cichowski et al. (1992) J. Biol. Chem. 267:5025–5028.

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
( A ) LENGTH: 3260 base pairs
( B ) TYPE: nucleic acid
( C ) STRANDEDNESS: double
( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
( A ) ORGANISM: MEKK
( B ) STRAIN: murine ( v i i ) IMMEDIATE SOURCE:
( A ) LIBRARY: mouse liver
( B ) CLONE: MEKK cDNA ( i x ) FEATURE:
    ( A ) NAME/KEY: 5'UTR
    ( B ) LOCATION: 1..485
    ( A ) NAME/KEY: CDS
    ( B ) LOCATION: 486..2501
    ( A ) NAME/KEY: 3'UTR
    ( B ) LOCATION: 2502..3260

( x i ) SEQUENCE DESCRIPTION: SEQ ID NO:1:

```
TACACTCCTT  GCCACAGTCT  GGCAGAAAGA  ATCAAACTTC  AGAGACTCCT  CCGGCCAGTT     60

GTAGACACTA  TCCTTGTCAA  GTGTGCAGAT  CCAACAGCCG  CACGAGTCAG  CTGTCCATAT    120

CTACAGTGCT  GGAACTCTGC  AAGGGCCAAG  CAGGAGAGCT  GGCGGTTGGG  AGAGAAATAC    180

TTAAAGCTGG  GTCCATCGGG  GTTGGTGGTG  TCGATTACGT  CTTAAGTTGT  ATCCTTGGAA    240

ACCAAGCTGA  ATCAAACAAC  TGGCAAGAAC  TGCTGGGTCG  CCTCTGTCTT  ATAGACAGGT    300

TGCTGTTGGA  ATTTCCTGCT  GAATTCTATC  CTCATATTGT  CAGTACTGAT  GTCTCACAAG    360

CTGAGCCTGT  TGAAATCAGG  TACAAGAAGC  TGCTCTCCCT  CTTAACCTTT  GCCTTGCAAT    420

CCATTGACAA  TTCCCACTCG  ATGGTTGGCA  AGCTCTCTCG  GAGGATATAT  CTGAGCTCTG    480
```

```
CCAGG ATG GTG ACC GCA GTG CCC GCT GTG TTT TCC AAG CTG GTA ACC            527
      Met Val Thr Ala Val Pro Ala Val Phe Ser Lys Leu Val Thr
      1               5                   10

ATG CTT AAT GCT TCT GGC TCC ACC CAC TTC ACC AGG ATG CGC CGG CGT          575
Met Leu Asn Ala Ser Gly Ser Thr His Phe Thr Arg Met Arg Arg Arg
15              20                  25                  30

CTG ATG GCT ATC GCG GAT GAG GTA GAA ATT GCC GAG GTC ATC CAG CTG          623
Leu Met Ala Ile Ala Asp Glu Val Glu Ile Ala Glu Val Ile Gln Leu
                35                  40                  45

GGT GTG GAG GAC ACT GTG GAT GGG CAT CAG GAC AGC TTA CAG GCC GTG          671
Gly Val Glu Asp Thr Val Asp Gly His Gln Asp Ser Leu Gln Ala Val
                50                  55                  60

GCC CCC ACC AGC TGT CTA GAA AAC AGC TCC CTT GAG CAC ACA GTC CAT          719
Ala Pro Thr Ser Cys Leu Glu Asn Ser Ser Leu Glu His Thr Val His
            65                  70                  75

AGA GAG AAA ACT GGA AAA GGA CTA AGT GCT ACG AGA CTG AGT GCC AGC          767
Arg Glu Lys Thr Gly Lys Gly Leu Ser Ala Thr Arg Leu Ser Ala Ser
        80                  85                  90

TCG GAG GAC ATT TCT GAC AGA CTG GCC GGC GTC TCT GTA GGA CTT CCC          815
Ser Glu Asp Ile Ser Asp Arg Leu Ala Gly Val Ser Val Gly Leu Pro
95                  100                 105                 110

AGC TCA ACA ACA ACA GAA CAA CCA AAG CCA GCG GTT CAA ACA AAA GGC          863
Ser Ser Thr Thr Thr Glu Gln Pro Lys Pro Ala Val Gln Thr Lys Gly
                115                 120                 125

AGA CCC CAC AGT CAG TGT TTG AAC TCC TCC CCT TTG TCT CAT GCT CAA          911
Arg Pro His Ser Gln Cys Leu Asn Ser Ser Pro Leu Ser His Ala Gln
            130                 135                 140

TTA ATG TTC CCA GCA CCA TCA GCC CCT TGT TCC TCT GCC CCG TCT GTC          959
Leu Met Phe Pro Ala Pro Ser Ala Pro Cys Ser Ser Ala Pro Ser Val
        145                 150                 155

CCA GAT ATT TCT AAG CAC AGA CCC CAG GCA TTT GTT CCC TGC AAA ATA         1007
Pro Asp Ile Ser Lys His Arg Pro Gln Ala Phe Val Pro Cys Lys Ile
160                 165                 170

CCT TCC GCA TCT CCT CAG ACA CAG CGC AAG TTC TCT CTA CAA TTC CAG         1055
Pro Ser Ala Ser Pro Gln Thr Gln Arg Lys Phe Ser Leu Gln Phe Gln
175                 180                 185                 190

AGG AAC TGC TCT GAA CAC CGA GAC TCA GAC CAG CTC TCC CCA GTC TTC         1103
Arg Asn Cys Ser Glu His Arg Asp Ser Asp Gln Leu Ser Pro Val Phe
                195                 200                 205

ACT CAG TCA AGA CCC CCA CCC TCC AGT AAC ATA CAC AGG CCA AAG CCA         1151
Thr Gln Ser Arg Pro Pro Pro Ser Ser Asn Ile His Arg Pro Lys Pro
```

-continued

|     |     |     | 210 |     |     |     |     | 215 |     |     |     |     | 220 |     |      |
|-----|-----|-----|-----|-----|-----|-----|-----|-----|-----|-----|-----|-----|-----|-----|------|
| TCC | CGA | CCC | GTT | CCG | GGC | AGT | ACA | AGC | AAA | CTA | GGG | GAC | GCC | ACA | AAA | 1199 |
| Ser | Arg | Pro | Val | Pro | Gly | Ser | Thr | Ser | Lys | Leu | Gly | Asp | Ala | Thr | Lys |
|     |     | 225 |     |     |     |     | 230 |     |     |     |     | 235 |     |     |     |

| AGT | AGC | ATG | ACA | CTT | GAT | CTG | GGC | AGT | GCT | TCC | AGG | TGT | GAC | GAC | AGC | 1247 |
| Ser | Ser | Met | Thr | Leu | Asp | Leu | Gly | Ser | Ala | Ser | Arg | Cys | Asp | Asp | Ser |
|     | 240 |     |     |     |     | 245 |     |     |     |     | 250 |     |     |     |     |

| TTT | GGC | GGC | GGC | GGC | AAC | AGT | GGC | AAC | GCC | GTC | ATA | CCC | AGC | GAC | GAG | 1295 |
| Phe | Gly | Gly | Gly | Gly | Asn | Ser | Gly | Asn | Ala | Val | Ile | Pro | Ser | Asp | Glu |
| 255 |     |     |     |     | 260 |     |     |     |     | 265 |     |     |     |     | 270 |

| ACA | GTG | TTC | ACG | CCG | GTG | GAG | GAC | AAG | TGC | AGG | TTA | GAT | GTG | AAC | ACC | 1343 |
| Thr | Val | Phe | Thr | Pro | Val | Glu | Asp | Lys | Cys | Arg | Leu | Asp | Val | Asn | Thr |
|     |     |     |     | 275 |     |     |     |     | 280 |     |     |     |     | 285 |     |

| GAG | CTC | AAC | TCC | AGC | ATC | GAG | GAC | CTT | CTT | GAA | GCA | TCC | ATG | CCT | TCA | 1391 |
| Glu | Leu | Asn | Ser | Ser | Ile | Glu | Asp | Leu | Leu | Glu | Ala | Ser | Met | Pro | Ser |
|     |     |     |     | 290 |     |     |     |     | 295 |     |     |     | 300 |     |     |

| AGT | GAC | ACG | ACA | GTC | ACT | TTC | AAG | TCC | GAA | GTC | GCC | GTC | CTC | TCT | CCG | 1439 |
| Ser | Asp | Thr | Thr | Val | Thr | Phe | Lys | Ser | Glu | Val | Ala | Val | Leu | Ser | Pro |
|     |     |     | 305 |     |     |     |     | 310 |     |     |     |     | 315 |     |     |

| GAA | AAG | GCC | GAA | AAT | GAC | GAC | ACC | TAC | AAA | GAC | GAC | GTC | AAT | CAT | AAT | 1487 |
| Glu | Lys | Ala | Glu | Asn | Asp | Asp | Thr | Tyr | Lys | Asp | Asp | Val | Asn | His | Asn |
|     | 320 |     |     |     |     | 325 |     |     |     |     | 330 |     |     |     |     |

| CAA | AAG | TGC | AAA | GAA | AAG | ATG | GAA | GCT | GAA | GAG | GAG | GAG | GCT | TTA | GCG | 1535 |
| Gln | Lys | Cys | Lys | Glu | Lys | Met | Glu | Ala | Glu | Glu | Glu | Glu | Ala | Leu | Ala |
| 335 |     |     |     |     | 340 |     |     |     |     | 345 |     |     |     |     | 350 |

| ATC | GCC | ATG | GCG | ATG | TCA | GCG | TCT | CAG | GAT | GCC | CTC | CCC | ATC | GTC | CCT | 1583 |
| Ile | Ala | Met | Ala | Met | Ser | Ala | Ser | Gln | Asp | Ala | Leu | Pro | Ile | Val | Pro |
|     |     |     |     | 355 |     |     |     |     | 360 |     |     |     |     | 365 |     |

| CAG | CTG | CAG | GTG | GAA | AAT | GGA | GAA | GAT | ATT | ATC | ATC | ATT | CAG | CAG | GAC | 1631 |
| Gln | Leu | Gln | Val | Glu | Asn | Gly | Glu | Asp | Ile | Ile | Ile | Ile | Gln | Gln | Asp |
|     |     |     | 370 |     |     |     |     | 375 |     |     |     |     | 380 |     |     |

| ACA | CCA | GAA | ACT | CTT | CCA | GGA | CAT | ACC | AAA | GCG | AAA | CAG | CCT | TAC | AGA | 1679 |
| Thr | Pro | Glu | Thr | Leu | Pro | Gly | His | Thr | Lys | Ala | Lys | Gln | Pro | Tyr | Arg |
|     |     |     | 385 |     |     |     |     | 390 |     |     |     |     | 395 |     |     |

| GAA | GAC | GCT | GAG | TGG | CTG | AAA | GGC | CAG | CAG | ATA | GGC | CTC | GGA | GCA | TTT | 1727 |
| Glu | Asp | Ala | Glu | Trp | Leu | Lys | Gly | Gln | Gln | Ile | Gly | Leu | Gly | Ala | Phe |
|     | 400 |     |     |     |     | 405 |     |     |     |     | 410 |     |     |     |     |

| TCT | TCC | TGT | TAC | CAA | GCA | CAG | GAT | GTG | GGG | ACT | GGG | ACT | TTA | ATG | GCT | 1775 |
| Ser | Ser | Cys | Tyr | Gln | Ala | Gln | Asp | Val | Gly | Thr | Gly | Thr | Leu | Met | Ala |
| 415 |     |     |     |     | 420 |     |     |     |     | 425 |     |     |     |     | 430 |

| GTG | AAA | CAG | GTG | ACG | TAC | GTC | AGA | AAC | ACA | TCC | TCC | GAG | CAG | GAG | GAG | 1823 |
| Val | Lys | Gln | Val | Thr | Tyr | Val | Arg | Asn | Thr | Ser | Ser | Glu | Gln | Glu | Glu |
|     |     |     |     | 435 |     |     |     |     | 440 |     |     |     |     | 445 |     |

| GTG | GTG | GAA | GCG | TTG | AGG | GAA | GAG | ATC | CGG | ATG | ATG | GGT | CAC | CTC | AAC | 1871 |
| Val | Val | Glu | Ala | Leu | Arg | Glu | Glu | Ile | Arg | Met | Met | Gly | His | Leu | Asn |
|     |     |     | 450 |     |     |     |     | 455 |     |     |     |     | 460 |     |     |

| CAT | CCA | AAC | ATC | ATC | CGG | ATG | CTG | GGG | GCC | ACG | TGC | GAG | AAG | AGC | AAC | 1919 |
| His | Pro | Asn | Ile | Ile | Arg | Met | Leu | Gly | Ala | Thr | Cys | Glu | Lys | Ser | Asn |
|     |     |     | 465 |     |     |     |     | 470 |     |     |     |     | 475 |     |     |

| TAC | AAC | CTC | TTC | ATT | GAG | TGG | ATG | GCG | GGA | GGA | TCT | GTG | GCT | CAC | CTC | 1967 |
| Tyr | Asn | Leu | Phe | Ile | Glu | Trp | Met | Ala | Gly | Gly | Ser | Val | Ala | His | Leu |
|     | 480 |     |     |     |     | 485 |     |     |     |     | 490 |     |     |     |     |

| TTG | AGT | AAA | TAC | GGA | GCT | TTC | AAG | GAG | TCA | GTC | GTC | ATT | AAC | TAC | ACT | 2015 |
| Leu | Ser | Lys | Tyr | Gly | Ala | Phe | Lys | Glu | Ser | Val | Val | Ile | Asn | Tyr | Thr |
| 495 |     |     |     |     | 500 |     |     |     |     | 505 |     |     |     |     | 510 |

| GAG | CAG | TTA | CTG | CGT | GGC | CTT | TCC | TAT | CTC | CAC | GAG | AAC | CAG | ATC | ATT | 2063 |
| Glu | Gln | Leu | Leu | Arg | Gly | Leu | Ser | Tyr | Leu | His | Glu | Asn | Gln | Ile | Ile |
|     |     |     |     | 515 |     |     |     |     | 520 |     |     |     |     | 525 |     |

| CAC | AGA | GAC | GTC | AAA | GGT | GCC | AAC | CTG | CTC | ATT | GAC | AGC | ACC | GGT | CAG | 2111 |
| His | Arg | Asp | Val | Lys | Gly | Ala | Asn | Leu | Leu | Ile | Asp | Ser | Thr | Gly | Gln |

|   |   |   |   |   |   |   |   |   |   |   |   |   |   |   |   |      |
|---|---|---|---|---|---|---|---|---|---|---|---|---|---|---|---|------|
|   |   | 530 |   |   |   |   | 535 |   |   |   |   | 540 |   |   |   |      |
| AGG | CTG | AGA | ATT | GCA | GAC | TTT | GGA | GCT | GCT | GCC | AGG | TTG | GCA | TCA | AAA | 2159 |
| Arg | Leu | Arg | Ile | Ala | Asp | Phe | Gly | Ala | Ala | Ala | Arg | Leu | Ala | Ser | Lys |      |
|     |     | 545 |     |     |     |     | 550 |     |     |     |     | 555 |     |     |     |      |
| GGA | ACC | GGT | GCA | GGA | GAG | TTC | CAG | GGA | CAG | TTA | CTG | GGG | ACA | ATT | GCA | 2207 |
| Gly | Thr | Gly | Ala | Gly | Glu | Phe | Gln | Gly | Gln | Leu | Leu | Gly | Thr | Ile | Ala |      |
|     | 560 |     |     |     |     |     | 565 |     |     |     |     | 570 |     |     |     |      |
| TTC | ATG | GCG | CCT | GAG | GTC | CTA | AGA | GGT | CAG | CAG | TAT | GGT | AGG | AGC | TGT | 2255 |
| Phe | Met | Ala | Pro | Glu | Val | Leu | Arg | Gly | Gln | Gln | Tyr | Gly | Arg | Ser | Cys |      |
| 575 |     |     |     | 580 |     |     |     |     | 585 |     |     |     |     |     | 590 |      |
| GAT | GTA | TGG | AGT | GTT | GGC | TGC | GCC | ATT | ATA | GAA | ATG | GCT | TGT | GCA | AAA | 2303 |
| Asp | Val | Trp | Ser | Val | Gly | Cys | Ala | Ile | Ile | Glu | Met | Ala | Cys | Ala | Lys |      |
|     |     |     |     | 595 |     |     |     |     | 600 |     |     |     |     | 605 |     |      |
| CCA | CCT | TGG | AAT | GCA | GAA | AAA | CAC | TCC | AAT | CAT | CTC | GCC | TTG | ATA | TTT | 2351 |
| Pro | Pro | Trp | Asn | Ala | Glu | Lys | His | Ser | Asn | His | Leu | Ala | Leu | Ile | Phe |      |
|     |     |     |     | 610 |     |     |     |     | 615 |     |     |     |     | 620 |     |      |
| AAG | ATT | GCT | AGC | GCA | ACT | ACT | GCA | CCG | TCC | ATC | CCG | TCA | CAC | CTG | TCC | 2399 |
| Lys | Ile | Ala | Ser | Ala | Thr | Thr | Ala | Pro | Ser | Ile | Pro | Ser | His | Leu | Ser |      |
|     |     |     | 625 |     |     |     |     | 630 |     |     |     |     | 635 |     |     |      |
| CCG | GGT | CTG | CGC | GAC | GTG | GCC | GTG | CGC | TGC | TTA | GAA | CTT | CAG | CCT | CAG | 2447 |
| Pro | Gly | Leu | Arg | Asp | Val | Ala | Val | Arg | Cys | Leu | Glu | Leu | Gln | Pro | Gln |      |
|     | 640 |     |     |     |     |     | 645 |     |     |     |     | 650 |     |     |     |      |
| GAC | CGG | CCT | CCG | TCC | AGA | GAG | CTG | CTG | AAA | CAT | CCG | GTC | TTC | CGT | ACC | 2495 |
| Asp | Arg | Pro | Pro | Ser | Arg | Glu | Leu | Leu | Lys | His | Pro | Val | Phe | Arg | Thr |      |
| 655 |     |     |     |     | 660 |     |     |     |     | 665 |     |     |     |     | 670 |      |
| ACG | TGG | TAGTTAATTG | TTCAGATCAG | CTCTAATGGA | GACAGGATAT | CGAACCGGGA |   |   |   |   |   |   |   |   |   | 2551 |
| Thr | Trp |   |   |   |   |   |   |   |   |   |   |   |   |   |   |      |

```
GAGAGAAAAG AGAACTTGTG GGCGACCATG CCGCTAACCG CAGCCCTCAC GCCACTGAAC    2611
AGCCAGAAAC GGGGCCAGCG GGAACCGTA  CCTAAGCATG TGATTGACAA ATCATGACCT    2671
GTACCTAAGC TCGATATGCA GACATCTACA GCTCGTGCAG GAACTGCACA CCGTGCCTTT    2731
CACAGGACTG GCTCTGGGGG ACCAGGAAGG CGATGGAGTT TGCATGACTA AGAACAGAA     2791
GCATAAATTT ATTTTTGGAG CACTTTTTCA GCTAATCAGT ATTACCATGT ACATCAACAT    2851
GCCCGCCACA TTTCAAACTC AGACTGTCCC AGATGTCAAG ATCCACTGTG TTTGAGTTTG    2911
TTTGCAGTTC CCTCAGCTTG CTGGTAATTG TGGTGTTTTG TTTTCGATGC AAATGTGATG    2971
TAATATTCTT ATTTTCTTTG GATCAAAGCT GGACTGAAAA TTGTACTGTG TAATTATTTT    3031
TGTGTTTTTA ATGTTATTTG GTACTCGAAT TGTAAATAAC GTCTACTGCT GTTTATTCCA    3091
GTTTCTACTA CCTCAGGTGT CCTATAGATT TTTCTTCTAC CAAAGTTCAC TCTCAGAATG    3151
AAATTCTACG TGCTGTGTGA CTATGACTCC TAAGACTTCC AGGGCTTAAG GGCTAACTCC    3211
TATTAGCACC TTACTATGTA AGCAAATGCT ACAAAAAAAA AAAAAAAA                 3260
```

( 2 ) INFORMATION FOR SEQ ID NO:2:

( i ) SEQUENCE CHARACTERISTICS:
        ( A ) LENGTH: 672 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Val | Thr | Ala | Val | Pro | Ala | Val | Phe | Ser | Lys | Leu | Val | Thr | Met | Leu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Asn | Ala | Ser | Gly | Ser | Thr | His | Phe | Thr | Arg | Met | Arg | Arg | Arg | Leu | Met |
|     |     |     | 20  |     |     |     |     | 25  |     |     |     |     | 30  |     |     |
| Ala | Ile | Ala | Asp | Glu | Val | Glu | Ile | Ala | Glu | Val | Ile | Gln | Leu | Gly | Val |

-continued

|  |  |  |  |  | 35 |  |  |  |  | 40 |  |  |  |  | 45 |  |  |  |
|---|---|---|---|---|---|---|---|---|---|---|---|---|---|---|---|---|---|---|
| Glu | Asp | Thr | Val | Asp | Gly | His | Gln | Asp | Ser | Leu | Gln | Ala | Val | Ala | Pro |
|  |  | 50 |  |  |  |  | 55 |  |  |  |  | 60 |  |  |  |
| Thr | Ser | Cys | Leu | Glu | Asn | Ser | Ser | Leu | Glu | His | Thr | Val | His | Arg | Glu |
| 65 |  |  |  |  | 70 |  |  |  |  | 75 |  |  |  |  | 80 |
| Lys | Thr | Gly | Lys | Gly | Leu | Ser | Ala | Thr | Arg | Leu | Ser | Ala | Ser | Ser | Glu |
|  |  |  |  | 85 |  |  |  |  | 90 |  |  |  |  | 95 |  |
| Asp | Ile | Ser | Asp | Arg | Leu | Ala | Gly | Val | Ser | Val | Gly | Leu | Pro | Ser | Ser |
|  |  |  | 100 |  |  |  |  | 105 |  |  |  |  | 110 |  |  |
| Thr | Thr | Thr | Glu | Gln | Pro | Lys | Pro | Ala | Val | Gln | Thr | Lys | Gly | Arg | Pro |
|  |  |  | 115 |  |  |  |  | 120 |  |  |  |  | 125 |  |  |
| His | Ser | Gln | Cys | Leu | Asn | Ser | Ser | Pro | Leu | Ser | His | Ala | Gln | Leu | Met |
|  |  | 130 |  |  |  |  | 135 |  |  |  |  | 140 |  |  |  |
| Phe | Pro | Ala | Pro | Ser | Ala | Pro | Cys | Ser | Ser | Ala | Pro | Ser | Val | Pro | Asp |
| 145 |  |  |  |  | 150 |  |  |  |  | 155 |  |  |  |  | 160 |
| Ile | Ser | Lys | His | Arg | Pro | Gln | Ala | Phe | Val | Pro | Cys | Lys | Ile | Pro | Ser |
|  |  |  |  | 165 |  |  |  |  | 170 |  |  |  |  | 175 |  |
| Ala | Ser | Pro | Gln | Thr | Gln | Arg | Lys | Phe | Ser | Leu | Gln | Phe | Gln | Arg | Asn |
|  |  |  | 180 |  |  |  |  | 185 |  |  |  |  | 190 |  |  |
| Cys | Ser | Glu | His | Arg | Asp | Ser | Asp | Gln | Leu | Ser | Pro | Val | Phe | Thr | Gln |
|  |  | 195 |  |  |  |  | 200 |  |  |  |  | 205 |  |  |  |
| Ser | Arg | Pro | Pro | Pro | Ser | Ser | Asn | Ile | His | Arg | Pro | Lys | Pro | Ser | Arg |
|  | 210 |  |  |  |  | 215 |  |  |  |  | 220 |  |  |  |  |
| Pro | Val | Pro | Gly | Ser | Thr | Ser | Lys | Leu | Gly | Asp | Ala | Thr | Lys | Ser | Ser |
| 225 |  |  |  |  | 230 |  |  |  |  | 235 |  |  |  |  | 240 |
| Met | Thr | Leu | Asp | Leu | Gly | Ser | Ala | Ser | Arg | Cys | Asp | Asp | Ser | Phe | Gly |
|  |  |  | 245 |  |  |  |  | 250 |  |  |  |  | 255 |  |  |
| Gly | Gly | Gly | Asn | Ser | Gly | Asn | Ala | Val | Ile | Pro | Ser | Asp | Glu | Thr | Val |
|  |  |  | 260 |  |  |  |  | 265 |  |  |  |  | 270 |  |  |
| Phe | Thr | Pro | Val | Glu | Asp | Lys | Cys | Arg | Leu | Asp | Val | Asn | Thr | Glu | Leu |
|  |  | 275 |  |  |  |  | 280 |  |  |  |  | 285 |  |  |  |
| Asn | Ser | Ser | Ile | Glu | Asp | Leu | Leu | Glu | Ala | Ser | Met | Pro | Ser | Ser | Asp |
|  | 290 |  |  |  |  | 295 |  |  |  |  | 300 |  |  |  |  |
| Thr | Thr | Val | Thr | Phe | Lys | Ser | Glu | Val | Ala | Val | Leu | Ser | Pro | Glu | Lys |
| 305 |  |  |  |  | 310 |  |  |  |  | 315 |  |  |  |  | 320 |
| Ala | Glu | Asn | Asp | Asp | Thr | Tyr | Lys | Asp | Asp | Val | Asn | His | Asn | Gln | Lys |
|  |  |  | 325 |  |  |  |  | 330 |  |  |  |  | 335 |  |  |
| Cys | Lys | Glu | Lys | Met | Glu | Ala | Glu | Glu | Glu | Ala | Leu | Ala | Ile | Ala |
|  |  |  | 340 |  |  |  |  | 345 |  |  |  |  | 350 |  |  |
| Met | Ala | Met | Ser | Ala | Ser | Gln | Asp | Ala | Leu | Pro | Ile | Val | Pro | Gln | Leu |
|  |  | 355 |  |  |  |  | 360 |  |  |  |  | 365 |  |  |  |
| Gln | Val | Glu | Asn | Gly | Glu | Asp | Ile | Ile | Ile | Ile | Gln | Gln | Asp | Thr | Pro |
|  | 370 |  |  |  |  | 375 |  |  |  |  | 380 |  |  |  |  |
| Glu | Thr | Leu | Pro | Gly | His | Thr | Lys | Ala | Lys | Gln | Pro | Tyr | Arg | Glu | Asp |
| 385 |  |  |  |  | 390 |  |  |  |  | 395 |  |  |  |  | 400 |
| Ala | Glu | Trp | Leu | Lys | Gly | Gln | Gln | Ile | Gly | Leu | Gly | Ala | Phe | Ser | Ser |
|  |  |  |  | 405 |  |  |  |  | 410 |  |  |  |  | 415 |  |
| Cys | Tyr | Gln | Ala | Gln | Asp | Val | Gly | Thr | Gly | Thr | Leu | Met | Ala | Val | Lys |
|  |  |  | 420 |  |  |  |  | 425 |  |  |  |  | 430 |  |  |
| Gln | Val | Thr | Tyr | Val | Arg | Asn | Thr | Ser | Ser | Glu | Gln | Glu | Glu | Val | Val |
|  |  | 435 |  |  |  |  | 440 |  |  |  |  | 445 |  |  |  |
| Glu | Ala | Leu | Arg | Glu | Glu | Ile | Arg | Met | Met | Gly | His | Leu | Asn | His | Pro |
|  | 450 |  |  |  |  | 455 |  |  |  |  | 460 |  |  |  |  |

|   |   |   |   |   |   |   |   |   |   |   |   |   |   |   |   |
|---|---|---|---|---|---|---|---|---|---|---|---|---|---|---|---|
| Asn | Ile | Ile | Arg | Met | Leu | Gly | Ala | Thr | Cys | Glu | Lys | Ser | Asn | Tyr | Asn |
| 465 |   |   |   | 470 |   |   |   |   | 475 |   |   |   |   |   | 480 |
| Leu | Phe | Ile | Glu | Trp | Met | Ala | Gly | Gly | Ser | Val | Ala | His | Leu | Leu | Ser |
|   |   |   |   | 485 |   |   |   |   | 490 |   |   |   |   | 495 |   |
| Lys | Tyr | Gly | Ala | Phe | Lys | Glu | Ser | Val | Val | Ile | Asn | Tyr | Thr | Glu | Gln |
|   |   |   | 500 |   |   |   |   | 505 |   |   |   |   | 510 |   |   |
| Leu | Leu | Arg | Gly | Leu | Ser | Tyr | Leu | His | Glu | Asn | Gln | Ile | Ile | His | Arg |
|   |   | 515 |   |   |   |   | 520 |   |   |   |   | 525 |   |   |   |
| Asp | Val | Lys | Gly | Ala | Asn | Leu | Leu | Ile | Asp | Ser | Thr | Gly | Gln | Arg | Leu |
|   | 530 |   |   |   |   | 535 |   |   |   |   | 540 |   |   |   |   |
| Arg | Ile | Ala | Asp | Phe | Gly | Ala | Ala | Arg | Leu | Ala | Ser | Lys | Gly | Thr |   |
| 545 |   |   |   |   | 550 |   |   |   | 555 |   |   |   |   | 560 |   |
| Gly | Ala | Gly | Glu | Phe | Gln | Gly | Gln | Leu | Leu | Gly | Thr | Ile | Ala | Phe | Met |
|   |   |   |   | 565 |   |   |   |   | 570 |   |   |   |   | 575 |   |
| Ala | Pro | Glu | Val | Leu | Arg | Gly | Gln | Gln | Tyr | Gly | Arg | Ser | Cys | Asp | Val |
|   |   |   | 580 |   |   |   |   | 585 |   |   |   |   | 590 |   |   |
| Trp | Ser | Val | Gly | Cys | Ala | Ile | Ile | Glu | Met | Ala | Cys | Ala | Lys | Pro | Pro |
|   |   | 595 |   |   |   |   | 600 |   |   |   |   |   | 605 |   |   |
| Trp | Asn | Ala | Glu | Lys | His | Ser | Asn | His | Leu | Ala | Leu | Ile | Phe | Lys | Ile |
|   | 610 |   |   |   |   | 615 |   |   |   |   | 620 |   |   |   |   |
| Ala | Ser | Ala | Thr | Thr | Ala | Pro | Ser | Ile | Pro | Ser | His | Leu | Ser | Pro | Gly |
| 625 |   |   |   |   | 630 |   |   |   |   | 635 |   |   |   |   | 640 |
| Leu | Arg | Asp | Val | Ala | Val | Arg | Cys | Leu | Glu | Leu | Gln | Pro | Gln | Asp | Arg |
|   |   |   |   | 645 |   |   |   |   | 650 |   |   |   |   | 655 |   |
| Pro | Pro | Ser | Arg | Glu | Leu | Leu | Lys | His | Pro | Val | Phe | Arg | Thr | Thr | Trp |
|   |   |   | 660 |   |   |   |   | 665 |   |   |   |   | 670 |   |   |

( 2 ) INFORMATION FOR SEQ ID NO:3:

( i ) SEQUENCE CHARACTERISTICS:
        ( A ) LENGTH: 2503 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 466..2325

( x i ) SEQUENCE DESCRIPTION: SEQ ID NO:3:

```
GGTGGCGGCC  GCTCTAGAAC  TAGTGGATCC  CCCGGGCTGC  AGGAATTCGG  CACGAGGGAC       60

GATCCAGCGG  CAGAGTCGCC  GCTTCCGCTT  CGCTGCTTCT  CCGGTCGGCG  ACGCGGGCCC      120

GGGGCTTCCT  TTTCATCGGC  CAGCTTATT   CCGCGGGCCC  CGGGGCTGCA  GCTACCCAGA      180

AGCGGCGAAG  AGGCCCTGGG  CTGCGCGCCC  GCTGTCCCAT  GTGAAGCAGG  TTGGGCCTGG      240

TCCCCGGCCC  GTGCCCGGTT  GTCTGCGGCC  CTTCAGGCCT  CAGGGACCCC  CGCGAGGCGC      300

TGCTCCTGGG  GGCGCGGTG   ACAGGCCGTG  CGGGGCGGA   GGGGCCAGCT  CGGTGGCCTC      360

CTCTCGGCCC  TCGCGTCCGC  GATCCCGCCC  AGCGGCCGGG  CAATAAAGAA  TGTTGATGGG      420

AGAACCATTT  TCCTAATTTT  CAAATTATTG  AGCTGGTCGC  GCATA ATG GAT GAT          474
                                                  Met Asp Asp
                                                    1

CAG CAA GCT TTG AAT TCA ATC ATG CAA GAT TTG GCT GTC CTT CAT AAG          522
Gln Gln Ala Leu Asn Ser Ile Met Gln Asp Leu Ala Val Leu His Lys
        5                  10                 15

CCA GTC GGC CAG CAT TAT CTT TAC AAG AAA CCA GGA AAG CAA AAC CTT          570
Pro Val Gly Gln His Tyr Leu Tyr Lys Lys Pro Gly Lys Gln Asn Leu
```

-continued

| | | | | | | | | | | | | | | | |
|---|---|---|---|---|---|---|---|---|---|---|---|---|---|---|---|
| | 20 | | | | 25 | | | | 30 | | | | 35 | | |
| CAT | CAC | CAA | AAA | AAC | AGA | ATG | ATG | TTC | GAG | TCA | AAT | TTG | AAC | ATA | GAG | 618 |
| His | His | Gln | Lys | Asn | Arg | Met | Met | Phe | Glu | Ser | Asn | Leu | Asn | Ile | Glu | |
| | | | | 40 | | | | 45 | | | | | 50 | | | |
| GAG | GAA | AAA | AGG | ATC | CTG | CAG | GTT | ACT | AGA | CCA | GTT | AAA | CTA | GAA | GAC | 666 |
| Glu | Glu | Lys | Arg | Ile | Leu | Gln | Val | Thr | Arg | Pro | Val | Lys | Leu | Glu | Asp | |
| | | | 55 | | | | | 60 | | | | 65 | | | | |
| CTG | AGA | TCT | AAG | TCT | AAG | ATC | GCC | TTT | GGG | CAG | TCT | ATG | GAT | CTA | CAC | 714 |
| Leu | Arg | Ser | Lys | Ser | Lys | Ile | Ala | Phe | Gly | Gln | Ser | Met | Asp | Leu | His | |
| | | 70 | | | | 75 | | | | | 80 | | | | | |
| TAT | ACC | AAC | AAT | GAG | TTG | GTA | ATT | CCG | TTA | ACT | ACC | CAA | GAT | GAC | TTG | 762 |
| Tyr | Thr | Asn | Asn | Glu | Leu | Val | Ile | Pro | Leu | Thr | Thr | Gln | Asp | Asp | Leu | |
| | 85 | | | | 90 | | | | | 95 | | | | | | |
| GAC | AAA | GCT | GTG | GAA | CTG | CTG | GAT | CGC | AGT | ATT | CAC | ATG | AAG | AGT | CTC | 810 |
| Asp | Lys | Ala | Val | Glu | Leu | Leu | Asp | Arg | Ser | Ile | His | Met | Lys | Ser | Leu | |
| 100 | | | | | 105 | | | | | 110 | | | | | 115 | |
| AAG | ATA | TTA | CTT | GTA | GTA | AAT | GGG | AGT | ACA | CAG | GCT | ACT | AAT | TTA | GAA | 858 |
| Lys | Ile | Leu | Leu | Val | Val | Asn | Gly | Ser | Thr | Gln | Ala | Thr | Asn | Leu | Glu | |
| | | | | 120 | | | | | 125 | | | | | 130 | | |
| CCA | TCA | CCG | TCA | CCA | GAA | GAT | TTG | AAT | AAT | ACA | CCA | CTT | GGT | GCA | GAG | 906 |
| Pro | Ser | Pro | Ser | Pro | Glu | Asp | Leu | Asn | Asn | Thr | Pro | Leu | Gly | Ala | Glu | |
| | | | 135 | | | | | 140 | | | | | 145 | | | |
| AGG | AAA | AAG | CGG | CTA | TCT | GTA | GTA | GGT | CCC | CCT | AAT | AGG | GAT | AGA | AGT | 954 |
| Arg | Lys | Lys | Arg | Leu | Ser | Val | Val | Gly | Pro | Pro | Asn | Arg | Asp | Arg | Ser | |
| | | 150 | | | | | 155 | | | | | 160 | | | | |
| TCC | CCT | CCT | CCA | GGA | TAC | ATT | CCA | GAC | ATA | CTA | CAC | CAG | ATT | GCC | CGG | 1002 |
| Ser | Pro | Pro | Pro | Gly | Tyr | Ile | Pro | Asp | Ile | Leu | His | Gln | Ile | Ala | Arg | |
| | 165 | | | | | 170 | | | | | 175 | | | | | |
| AAT | GGG | TCA | TTC | ACT | AGC | ATC | AAC | AGT | GAA | GGA | GAG | TTC | ATT | CCA | GAG | 1050 |
| Asn | Gly | Ser | Phe | Thr | Ser | Ile | Asn | Ser | Glu | Gly | Glu | Phe | Ile | Pro | Glu | |
| 180 | | | | | 185 | | | | | 190 | | | | | 195 | |
| AGC | ATG | GAC | CAA | ATG | CTG | GAT | CCA | TTG | TCT | TTA | AGC | AGC | CCT | GAA | AAT | 1098 |
| Ser | Met | Asp | Gln | Met | Leu | Asp | Pro | Leu | Ser | Leu | Ser | Ser | Pro | Glu | Asn | |
| | | | | 200 | | | | | 205 | | | | | 210 | | |
| TCT | GGC | TCA | GGA | AGC | TGT | CCG | TCA | CTT | GAT | AGT | CCT | TTG | GAT | GGA | GAA | 1146 |
| Ser | Gly | Ser | Gly | Ser | Cys | Pro | Ser | Leu | Asp | Ser | Pro | Leu | Asp | Gly | Glu | |
| | | | 215 | | | | | 220 | | | | | 225 | | | |
| AGC | TAC | CCA | AAA | TCA | CGG | ATG | CCT | AGG | GCA | CAG | AGC | TAC | CCA | GAT | AAT | 1194 |
| Ser | Tyr | Pro | Lys | Ser | Arg | Met | Pro | Arg | Ala | Gln | Ser | Tyr | Pro | Asp | Asn | |
| | | 230 | | | | | 235 | | | | | 240 | | | | |
| CAT | CAG | GAG | TTT | ACA | GAC | TAT | GAT | AAC | CCC | ATT | TTT | GAG | AAA | TTT | GGA | 1242 |
| His | Gln | Glu | Phe | Thr | Asp | Tyr | Asp | Asn | Pro | Ile | Phe | Glu | Lys | Phe | Gly | |
| | 245 | | | | | 250 | | | | | 255 | | | | | |
| AAA | GGA | GGA | ACA | TAT | CCA | AGA | AGG | TAC | CAC | GTT | TCC | TAT | CAT | CAC | CAG | 1290 |
| Lys | Gly | Gly | Thr | Tyr | Pro | Arg | Arg | Tyr | His | Val | Ser | Tyr | His | His | Gln | |
| 260 | | | | | 265 | | | | | 270 | | | | | 275 | |
| GAG | TAT | AAT | GAC | GGT | CGG | AAG | ACT | TTT | CCA | AGA | GCT | AGA | AGG | ACC | CAG | 1338 |
| Glu | Tyr | Asn | Asp | Gly | Arg | Lys | Thr | Phe | Pro | Arg | Ala | Arg | Arg | Thr | Gln | |
| | | | 280 | | | | | 285 | | | | | 290 | | | |
| GGC | ACC | AGT | TTC | CGG | TCT | CCT | GTG | AGC | TTC | AGT | CCT | ACT | GAT | CAC | TCC | 1386 |
| Gly | Thr | Ser | Phe | Arg | Ser | Pro | Val | Ser | Phe | Ser | Pro | Thr | Asp | His | Ser | |
| | | | 295 | | | | | 300 | | | | | 305 | | | |
| TTA | AGC | ACT | AGT | AGT | GGA | AGC | AGT | GTC | TTT | ACC | CCA | GAG | TAT | GAC | GAC | 1434 |
| Leu | Ser | Thr | Ser | Ser | Gly | Ser | Ser | Val | Phe | Thr | Pro | Glu | Tyr | Asp | Asp | |
| | | 310 | | | | | 315 | | | | | 320 | | | | |
| AGT | CGA | ATA | AGA | AGA | CGG | GGG | AGT | GAC | ATA | GAC | AAT | CCT | ACT | TTG | ACT | 1482 |
| Ser | Arg | Ile | Arg | Arg | Arg | Gly | Ser | Asp | Ile | Asp | Asn | Pro | Thr | Leu | Thr | |
| | 325 | | | | | 330 | | | | | 335 | | | | | |
| GTC | ACA | GAC | ATC | AGC | CCA | CCC | AGC | CGT | TCA | CCT | CGA | GCT | CCG | ACC | AAC | 1530 |
| Val | Thr | Asp | Ile | Ser | Pro | Pro | Ser | Arg | Ser | Pro | Arg | Ala | Pro | Thr | Asn | |

| | | | | | | | | | | | | | | | |
|---|---|---|---|---|---|---|---|---|---|---|---|---|---|---|---|
|340| | | | |345| | | | |350| | | | |355|

```
TGG AGA CTG GGC AAG CTG CTT GGC CAA GGA GCT TTT GGT AGG GTC TAC    1578
Trp Arg Leu Gly Lys Leu Leu Gly Gln Gly Ala Phe Gly Arg Val Tyr
                360                 365                 370

CTC TGC TAT GAT GTT GAT ACC GGA AGA GAG CTG GCT GTT AAG CAA GTT    1626
Leu Cys Tyr Asp Val Asp Thr Gly Arg Glu Leu Ala Val Lys Gln Val
            375                 380                 385

CAG TTT AAC CCT GAG AGC CCA GAG ACC AGC AAG GAA GTA AAT GCA CTT    1674
Gln Phe Asn Pro Glu Ser Pro Glu Thr Ser Lys Glu Val Asn Ala Leu
        390                 395                 400

GAG TGT GAA ATT CAG TTG TTG AAA AAC TTG TTG CAT GAG CGA ATT GTT    1722
Glu Cys Glu Ile Gln Leu Leu Lys Asn Leu Leu His Glu Arg Ile Val
    405                 410                 415

CAG TAT TAT GGC TGT TTG AGG GAT CCT CAG GAG AAA ACA CTT TCC ATC    1770
Gln Tyr Tyr Gly Cys Leu Arg Asp Pro Gln Glu Lys Thr Leu Ser Ile
420                 425                 430                 435

TTT ATG GAG CTC TCG CCA GGG GGT TCA ATT AAG GAC CAA CTA AAA GCC    1818
Phe Met Glu Leu Ser Pro Gly Gly Ser Ile Lys Asp Gln Leu Lys Ala
                440                 445                 450

TAC GGA GCT CTT ACT GAG AAC GTG ACG AGG AAG TAC ACC CGT CAG ATT    1866
Tyr Gly Ala Leu Thr Glu Asn Val Thr Arg Lys Tyr Thr Arg Gln Ile
            455                 460                 465

CTG GAG GGG GTC CAT TAT TTG CAT AGT AAT ATG ATT GTC CAT AGA GAT    1914
Leu Glu Gly Val His Tyr Leu His Ser Asn Met Ile Val His Arg Asp
        470                 475                 480

ATC AAA GGA GCA AAT ATC TTA AGG GAT TCC ACA GGC AAT ATC AAG TTA    1962
Ile Lys Gly Ala Asn Ile Leu Arg Asp Ser Thr Gly Asn Ile Lys Leu
    485                 490                 495

GGA GAC TTT GGG GCT AGT AAA CGG CTT CAG ACC ATC TGT CTC TCA GGC    2010
Gly Asp Phe Gly Ala Ser Lys Arg Leu Gln Thr Ile Cys Leu Ser Gly
500                 505                 510                 515

ACA GGA ATG AAG TCT GTC ACA GGC ACG CCA TAC TGG ATG AGT CCT GAG    2058
Thr Gly Met Lys Ser Val Thr Gly Thr Pro Tyr Trp Met Ser Pro Glu
                520                 525                 530

GTC ATC AGT GGA GAA GGC TAT GGA AGA AAA GCA GAC ATC TGG AGT GTA    2106
Val Ile Ser Gly Glu Gly Tyr Gly Arg Lys Ala Asp Ile Trp Ser Val
            535                 540                 545

GCA TGT ACT GTG GTA GAA ATG CTA ACT GAA AAG CCA CCT TGG GCT GAA    2154
Ala Cys Thr Val Val Glu Met Leu Thr Glu Lys Pro Pro Trp Ala Glu
        550                 555                 560

TTT GAA GCA ATG GCT GCC ATC TTT AAG ATC GCC ACT CAG CCA ACG AAC    2202
Phe Glu Ala Met Ala Ala Ile Phe Lys Ile Ala Thr Gln Pro Thr Asn
    565                 570                 575

CCA AAG CTG CCA CCT CAT GTC TCA GAC TAT ACT CGG GAC TTC CTC AAA    2250
Pro Lys Leu Pro Pro His Val Ser Asp Tyr Thr Arg Asp Phe Leu Lys
580                 585                 590                 595

CGG ATT TTT GTA GAG GCC AAA CTT CGA CCT TCA GCG GAG GAG CTC TTG    2298
Arg Ile Phe Val Glu Ala Lys Leu Arg Pro Ser Ala Glu Glu Leu Leu
                600                 605                 610

CGG CAC ATG TTT GTG CAT TAT CAC TAGCAGCGGC GGCTTCGGTC CTCCACCAGC   2352
Arg His Met Phe Val His Tyr His
            615                 620

TCCATCCTCG CGGCCACCTT CTCTCTTACT GCACTTTCCT TTTTTATAAA AAAGAGAGAT   2412

GGGGAGAAAA AGACAAGAGG GAAAATATTT CTCTTGATTC TTGGTTAAAT TTGTTTAATA   2472

ATAATAGTAA ACTAAAAAAA AAAAAAAAAA A                                  2503
```

( 2 ) INFORMATION FOR SEQ ID NO:4:

( i ) SEQUENCE CHARACTERISTICS:

( A ) LENGTH: 619 amino acids
( B ) TYPE: amino acid
( D ) TOPOLOGY: linear ( i i ) MOLECULE TYPE: protein ( x i ) SEQUENCE DESCRIPTION: SEQ ID NO:4:

| Met | Asp | Asp | Gln | Gln | Ala | Leu | Asn | Ser | Ile | Met | Gln | Asp | Leu | Ala | Val |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Leu | His | Lys | Pro | Val | Gly | Gln | His | Tyr | Leu | Tyr | Lys | Lys | Pro | Gly | Lys |
|     |     |     | 20  |     |     |     |     | 25  |     |     |     |     | 30  |     |     |
| Gln | Asn | Leu | His | His | Gln | Lys | Asn | Arg | Met | Met | Phe | Glu | Ser | Asn | Leu |
|     |     | 35  |     |     |     |     | 40  |     |     |     |     | 45  |     |     |     |
| Asn | Ile | Glu | Glu | Glu | Lys | Arg | Ile | Leu | Gln | Val | Thr | Arg | Pro | Val | Lys |
|     | 50  |     |     |     |     | 55  |     |     |     |     | 60  |     |     |     |     |
| Leu | Glu | Asp | Leu | Arg | Ser | Lys | Ser | Lys | Ile | Ala | Phe | Gly | Gln | Ser | Met |
| 65  |     |     |     |     | 70  |     |     |     |     | 75  |     |     |     |     | 80  |
| Asp | Leu | His | Tyr | Thr | Asn | Asn | Glu | Leu | Val | Ile | Pro | Leu | Thr | Thr | Gln |
|     |     |     |     | 85  |     |     |     |     | 90  |     |     |     |     | 95  |     |
| Asp | Asp | Leu | Asp | Lys | Ala | Val | Glu | Leu | Leu | Asp | Arg | Ser | Ile | His | Met |
|     |     |     | 100 |     |     |     |     | 105 |     |     |     |     | 110 |     |     |
| Lys | Ser | Leu | Lys | Ile | Leu | Leu | Val | Val | Asn | Gly | Ser | Thr | Gln | Ala | Thr |
|     |     | 115 |     |     |     |     | 120 |     |     |     |     | 125 |     |     |     |
| Asn | Leu | Glu | Pro | Ser | Pro | Ser | Pro | Glu | Asp | Leu | Asn | Asn | Thr | Pro | Leu |
|     | 130 |     |     |     |     | 135 |     |     |     |     | 140 |     |     |     |     |
| Gly | Ala | Glu | Arg | Lys | Lys | Arg | Leu | Ser | Val | Val | Gly | Pro | Pro | Asn | Arg |
| 145 |     |     |     |     | 150 |     |     |     |     | 155 |     |     |     |     | 160 |
| Asp | Arg | Ser | Ser | Pro | Pro | Gly | Tyr | Ile | Pro | Asp | Ile | Leu | His | Gln |
|     |     |     |     | 165 |     |     |     | 170 |     |     |     |     | 175 |     |
| Ile | Ala | Arg | Asn | Gly | Ser | Phe | Thr | Ser | Ile | Asn | Ser | Glu | Gly | Glu | Phe |
|     |     |     | 180 |     |     |     |     | 185 |     |     |     |     | 190 |     |     |
| Ile | Pro | Glu | Ser | Met | Asp | Gln | Met | Leu | Asp | Pro | Leu | Ser | Leu | Ser | Ser |
|     |     | 195 |     |     |     | 200 |     |     |     |     | 205 |     |     |     |     |
| Pro | Glu | Asn | Ser | Gly | Ser | Gly | Ser | Cys | Pro | Ser | Leu | Asp | Ser | Pro | Leu |
|     | 210 |     |     |     |     | 215 |     |     |     |     | 220 |     |     |     |     |
| Asp | Gly | Glu | Ser | Tyr | Pro | Lys | Ser | Arg | Met | Pro | Arg | Ala | Gln | Ser | Tyr |
| 225 |     |     |     |     | 230 |     |     |     |     | 235 |     |     |     |     | 240 |
| Pro | Asp | Asn | His | Gln | Glu | Phe | Thr | Asp | Tyr | Asp | Asn | Pro | Ile | Phe | Glu |
|     |     |     |     | 245 |     |     |     |     | 250 |     |     |     |     | 255 |     |
| Lys | Phe | Gly | Lys | Gly | Gly | Thr | Tyr | Pro | Arg | Arg | Tyr | His | Val | Ser | Tyr |
|     |     |     | 260 |     |     |     |     | 265 |     |     |     |     | 270 |     |     |
| His | His | Gln | Glu | Tyr | Asn | Asp | Gly | Arg | Lys | Thr | Phe | Pro | Arg | Ala | Arg |
|     |     | 275 |     |     |     |     | 280 |     |     |     |     | 285 |     |     |     |
| Arg | Thr | Gln | Gly | Thr | Ser | Phe | Arg | Ser | Pro | Val | Ser | Phe | Ser | Pro | Thr |
|     | 290 |     |     |     |     | 295 |     |     |     |     | 300 |     |     |     |     |
| Asp | His | Ser | Leu | Ser | Thr | Ser | Ser | Gly | Ser | Ser | Val | Phe | Thr | Pro | Glu |
| 305 |     |     |     |     | 310 |     |     |     |     | 315 |     |     |     |     | 320 |
| Tyr | Asp | Asp | Ser | Arg | Ile | Arg | Arg | Arg | Gly | Ser | Asp | Ile | Asp | Asn | Pro |
|     |     |     |     | 325 |     |     |     |     | 330 |     |     |     |     | 335 |     |
| Thr | Leu | Thr | Val | Thr | Asp | Ile | Ser | Pro | Pro | Ser | Arg | Ser | Pro | Arg | Ala |
|     |     |     | 340 |     |     |     |     | 345 |     |     |     |     | 350 |     |     |
| Pro | Thr | Asn | Trp | Arg | Leu | Gly | Lys | Leu | Leu | Gly | Gln | Gly | Ala | Phe | Gly |
|     |     | 355 |     |     |     |     | 360 |     |     |     |     | 365 |     |     |     |
| Arg | Val | Tyr | Leu | Cys | Tyr | Asp | Val | Asp | Thr | Gly | Arg | Glu | Leu | Ala | Val |
|     | 370 |     |     |     |     | 375 |     |     |     |     | 380 |     |     |     |     |

| | | | | | | | | | | | | | | |
|---|---|---|---|---|---|---|---|---|---|---|---|---|---|---|
| Lys | Gln | Val | Gln | Phe | Asn | Pro | Glu | Ser | Pro | Glu | Thr | Ser | Lys | Glu | Val |
| 385 | | | | | 390 | | | | 395 | | | | | | 400 |
| Asn | Ala | Leu | Glu | Cys | Glu | Ile | Gln | Leu | Leu | Lys | Asn | Leu | Leu | His | Glu |
| | | | | 405 | | | | | 410 | | | | | 415 | |
| Arg | Ile | Val | Gln | Tyr | Tyr | Gly | Cys | Leu | Arg | Asp | Pro | Gln | Glu | Lys | Thr |
| | | | 420 | | | | | 425 | | | | | 430 | | |
| Leu | Ser | Ile | Phe | Met | Glu | Leu | Ser | Pro | Gly | Gly | Ser | Ile | Lys | Asp | Gln |
| | | | 435 | | | | | 440 | | | | 445 | | | |
| Leu | Lys | Ala | Tyr | Gly | Ala | Leu | Thr | Glu | Asn | Val | Thr | Arg | Lys | Tyr | Thr |
| | | 450 | | | | 455 | | | | | 460 | | | | |
| Arg | Gln | Ile | Leu | Glu | Gly | Val | His | Tyr | Leu | His | Ser | Asn | Met | Ile | Val |
| 465 | | | | | 470 | | | | | 475 | | | | | 480 |
| His | Arg | Asp | Ile | Lys | Gly | Ala | Asn | Ile | Leu | Arg | Asp | Ser | Thr | Gly | Asn |
| | | | | 485 | | | | | 490 | | | | | 495 | |
| Ile | Lys | Leu | Gly | Asp | Phe | Gly | Ala | Ser | Lys | Arg | Leu | Gln | Thr | Ile | Cys |
| | | | 500 | | | | | 505 | | | | | 510 | | |
| Leu | Ser | Gly | Thr | Gly | Met | Lys | Ser | Val | Thr | Gly | Thr | Pro | Tyr | Trp | Met |
| | | 515 | | | | | 520 | | | | | 525 | | | |
| Ser | Pro | Glu | Val | Ile | Ser | Gly | Glu | Gly | Tyr | Gly | Arg | Lys | Ala | Asp | Ile |
| | 530 | | | | | 535 | | | | | 540 | | | | |
| Trp | Ser | Val | Ala | Cys | Thr | Val | Val | Glu | Met | Leu | Thr | Glu | Lys | Pro | Pro |
| 545 | | | | | 550 | | | | | 555 | | | | | 560 |
| Trp | Ala | Glu | Phe | Glu | Ala | Met | Ala | Ala | Ile | Phe | Lys | Ile | Ala | Thr | Gln |
| | | | | 565 | | | | | 570 | | | | | 575 | |
| Pro | Thr | Asn | Pro | Lys | Leu | Pro | Pro | His | Val | Ser | Asp | Tyr | Thr | Arg | Asp |
| | | | 580 | | | | | 585 | | | | | 590 | | |
| Phe | Leu | Lys | Arg | Ile | Phe | Val | Glu | Ala | Lys | Leu | Arg | Pro | Ser | Ala | Glu |
| | | 595 | | | | | 600 | | | | | 605 | | | |
| Glu | Leu | Leu | Arg | His | Met | Phe | Val | His | Tyr | His | | | | | |
| | 610 | | | | | 615 | | | | | | | | | |

(2) INFORMATION FOR SEQ ID NO:5:

(i) SEQUENCE CHARACTERISTICS:
        (A) LENGTH: 3089 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 400..2280

(xi) SEQUENCE DESCRIPTION: SEQ ID NO:5:

```
AGGGAACAAA AGCTGGAGCT CCACCGCGGT GGCGGCCGCT CTAGAACTAG TGGATCCCCC    60

GGGCTGCAGG AATTCGGCAC GAGGAACAGT GGCCGGTCGG AGCGTCTTCT GGACTTCAGG   120

ACTCGCAGGC GGCCCGGTCG AGTGGCGCCG CCGAGGCCGG GTTGGGCCGA GCCTGGGAGC   180

GCCGGGGATG TAGCGGGCCA ACCTGCTCAT GCCACAGCGC CCGGCCGCGG CCGAGCCGGA   240

GCCTGGGGAG GCGGCGGGGG CCCCGAGCGC AGCCCACGGC CCCCGCGCGG AGCCAGGCCC   300

GCTGCCGTCC CCGCCGCCCG CTCCCCCGGC ATGCAGCCCC GGCTGCGGAG GTGACACTTC   360

TGGGCTGTAG TCGCCACCGC CGCCTCCGCC ATCGCCACC ATG GAT GAA CAA GAG     414
                                             Met Asp Glu Gln Glu
                                              1               5

GCA TTA GAC TCG ATC ATG AAG GAC CTG GTG GCC CTC CAG ATG AGC CGA    462
Ala Leu Asp Ser Ile Met Lys Asp Leu Val Ala Leu Gln Met Ser Arg
```

|  |  |  |  |  |  |  |  |  |  |  |  |  |  |  |  |
|---|---|---|---|---|---|---|---|---|---|---|---|---|---|---|---|
|  |  |  | 10 |  |  |  |  | 15 |  |  |  |  | 20 |  |  |
| CGA | ACC | CGG | TTG | TCT | GGA | TAT | GAG | ACC | ATG | AAG | AAT | AAG | GAC | ACA | GGT | 510 |
| Arg | Thr | Arg | Leu | Ser | Gly | Tyr | Glu | Thr | Met | Lys | Asn | Lys | Asp | Thr | Gly |
|  |  |  | 25 |  |  |  |  | 30 |  |  |  |  | 35 |  |  |
| CAC | CCA | AAC | AGG | CAG | AGT | GAC | GTC | AGA | ATC | AAG | TTT | GAA | CAC | AAT | GGG | 558 |
| His | Pro | Asn | Arg | Gln | Ser | Asp | Val | Arg | Ile | Lys | Phe | Glu | His | Asn | Gly |
|  |  |  | 40 |  |  |  |  | 45 |  |  |  |  | 50 |  |  |
| GAG | AGA | CGA | ATT | ATA | GCA | TTC | AGC | CGG | CCT | GTG | AGA | TAC | GAA | GAT | GTG | 606 |
| Glu | Arg | Arg | Ile | Ile | Ala | Phe | Ser | Arg | Pro | Val | Arg | Tyr | Glu | Asp | Val |
|  |  | 55 |  |  |  |  | 60 |  |  |  |  | 65 |  |  |  |
| GAG | CAC | AAG | GTG | ACA | ACA | GTC | TTT | GGG | CAG | CCT | CTT | GAT | TTG | CAT | TAT | 654 |
| Glu | His | Lys | Val | Thr | Thr | Val | Phe | Gly | Gln | Pro | Leu | Asp | Leu | His | Tyr |
|  | 70 |  |  |  |  | 75 |  |  |  |  | 80 |  |  |  | 85 |
| ATG | AAT | AAT | GAG | CTC | TCC | ATC | CTG | TTG | AAA | AAC | CAA | GAT | GAT | CTC | GAT | 702 |
| Met | Asn | Asn | Glu | Leu | Ser | Ile | Leu | Leu | Lys | Asn | Gln | Asp | Asp | Leu | Asp |
|  |  |  |  | 90 |  |  |  |  | 95 |  |  |  |  | 100 |  |
| AAA | GCC | ATT | GAC | ATT | TTG | GAT | AGA | AGC | TCA | AGT | ATG | AAA | AGC | CTT | AGG | 750 |
| Lys | Ala | Ile | Asp | Ile | Leu | Asp | Arg | Ser | Ser | Ser | Met | Lys | Ser | Leu | Arg |
|  |  |  |  | 105 |  |  |  |  | 110 |  |  |  |  | 115 |  |
| ATA | CTA | CTG | TTA | TCC | CAA | GAC | AGA | AAC | CAT | ACT | AGT | TCC | TCT | CCC | CAC | 798 |
| Ile | Leu | Leu | Leu | Ser | Gln | Asp | Arg | Asn | His | Thr | Ser | Ser | Ser | Pro | His |
|  |  | 120 |  |  |  |  | 125 |  |  |  |  | 130 |  |  |  |
| TCT | GGA | GTG | TCC | AGG | CAG | GTT | CGG | ATC | AAG | CCT | TCC | CAG | TCT | GCA | GGG | 846 |
| Ser | Gly | Val | Ser | Arg | Gln | Val | Arg | Ile | Lys | Pro | Ser | Gln | Ser | Ala | Gly |
|  | 135 |  |  |  |  | 140 |  |  |  |  | 145 |  |  |  |  |
| GAT | ATA | AAT | ACC | ATC | TAC | CAA | GCT | CCT | GAG | CCC | AGA | AGC | AGG | CAC | CTG | 894 |
| Asp | Ile | Asn | Thr | Ile | Tyr | Gln | Ala | Pro | Glu | Pro | Arg | Ser | Arg | His | Leu |
| 150 |  |  |  |  | 155 |  |  |  |  | 160 |  |  |  |  | 165 |
| TCT | GTC | AGC | TCC | CAG | AAC | CCT | GGC | CGA | AGC | TCT | CCT | CCC | CCG | GGA | TAT | 942 |
| Ser | Val | Ser | Ser | Gln | Asn | Pro | Gly | Arg | Ser | Ser | Pro | Pro | Pro | Gly | Tyr |
|  |  |  |  | 170 |  |  |  |  | 175 |  |  |  |  | 180 |  |
| GTA | CCT | GAG | CGA | CAA | CAG | CAC | ATT | GCC | CGG | CAA | GGA | TCC | TAT | ACG | AGC | 990 |
| Val | Pro | Glu | Arg | Gln | Gln | His | Ile | Ala | Arg | Gln | Gly | Ser | Tyr | Thr | Ser |
|  |  |  | 185 |  |  |  |  | 190 |  |  |  |  | 195 |  |  |
| ATC | AAC | AGC | GAA | GGT | GAA | TTC | ATC | CCA | GAG | ACC | AGC | GAA | CAG | TGT | ATG | 1038 |
| Ile | Asn | Ser | Glu | Gly | Glu | Phe | Ile | Pro | Glu | Thr | Ser | Glu | Gln | Cys | Met |
|  |  | 200 |  |  |  |  | 205 |  |  |  |  | 210 |  |  |  |
| CTA | GAT | CCC | CTC | AGC | AGT | GCC | GAA | AAT | TCC | TTG | TCA | GGA | AGC | TGC | CAA | 1086 |
| Leu | Asp | Pro | Leu | Ser | Ser | Ala | Glu | Asn | Ser | Leu | Ser | Gly | Ser | Cys | Gln |
|  | 215 |  |  |  |  | 220 |  |  |  |  | 225 |  |  |  |  |
| TCC | TTG | GAC | AGG | TCA | GCA | GAC | AGC | CCA | TCC | TTC | AGG | AAA | TCA | CAA | ATG | 1134 |
| Ser | Leu | Asp | Arg | Ser | Ala | Asp | Ser | Pro | Ser | Phe | Arg | Lys | Ser | Gln | Met |
| 230 |  |  |  |  | 235 |  |  |  |  | 240 |  |  |  |  | 245 |
| TCC | CGA | GCC | CGG | AGC | TTC | CCA | GAC | AAC | AGA | AAG | GAA | TGC | TCA | GAT | CGG | 1182 |
| Ser | Arg | Ala | Arg | Ser | Phe | Pro | Asp | Asn | Arg | Lys | Glu | Cys | Ser | Asp | Arg |
|  |  |  |  | 250 |  |  |  |  | 255 |  |  |  |  | 260 |  |
| GAG | ACC | CAG | CTC | TAT | GAT | AAA | GGT | GTC | AAA | GGT | GGA | ACC | TAT | CCC | AGG | 1230 |
| Glu | Thr | Gln | Leu | Tyr | Asp | Lys | Gly | Val | Lys | Gly | Gly | Thr | Tyr | Pro | Arg |
|  |  |  | 265 |  |  |  |  | 270 |  |  |  |  | 275 |  |  |
| CGC | TAC | CAT | GTG | TCT | GTG | CAT | CAC | AAA | GAC | TAC | AAT | GAT | GGC | AGA | AGA | 1278 |
| Arg | Tyr | His | Val | Ser | Val | His | His | Lys | Asp | Tyr | Asn | Asp | Gly | Arg | Arg |
|  |  | 280 |  |  |  |  | 285 |  |  |  |  | 290 |  |  |  |
| ACA | TTT | CCC | CGA | ATA | CGA | CGG | CAT | CAA | GGC | AAC | CTA | TTC | ACT | CTG | GTG | 1326 |
| Thr | Phe | Pro | Arg | Ile | Arg | Arg | His | Gln | Gly | Asn | Leu | Phe | Thr | Leu | Val |
|  | 295 |  |  |  |  | 300 |  |  |  |  | 305 |  |  |  |  |
| CCC | TCA | AGT | CGC | TCC | TTG | AGC | ACA | AAT | GGC | GAG | AAC | ATG | GGT | GTA | GCT | 1374 |
| Pro | Ser | Ser | Arg | Ser | Leu | Ser | Thr | Asn | Gly | Glu | Asn | Met | Gly | Val | Ala |
| 310 |  |  |  |  | 315 |  |  |  |  | 320 |  |  |  |  | 325 |
| GTG | CAA | TAC | CTG | GAC | CCC | CGT | GGG | CGC | CTA | CGG | AGT | GCA | GAC | AGT | GAG | 1422 |
| Val | Gln | Tyr | Leu | Asp | Pro | Arg | Gly | Arg | Leu | Arg | Ser | Ala | Asp | Ser | Glu |

```
            330                           335                          340
AAT GCC CTC ACT GTG CAG GAA AGG AAT GTG CCA ACC AAA TCT CCT AGT              1470
Asn Ala Leu Thr Val Gln Glu Arg Asn Val Pro Thr Lys Ser Pro Ser
            345                           350                      355

GCT CCC ATC AAT TGG CGT CGG GGG AAG CTC CTG GGT CAA GGT GCC TTC              1518
Ala Pro Ile Asn Trp Arg Arg Gly Lys Leu Leu Gly Gln Gly Ala Phe
                    360                           365              370

GGC AGG GTC TAC TTG TGC TAT GAT GTG GAC ACA GGA CGT GAA CTT GCT              1566
Gly Arg Val Tyr Leu Cys Tyr Asp Val Asp Thr Gly Arg Glu Leu Ala
        375                           380                      385

TCT AAG CAG GTC CAG TTT GAC CCA GAT AGT CCT GAG ACA AGC AAG GAG              1614
Ser Lys Gln Val Gln Phe Asp Pro Asp Ser Pro Glu Thr Ser Lys Glu
390                          395                      400                   405

GTG AGT GCT CTG GAG TGT GAG ATC CAG TTG CTG AAG AAC CTG CAG CAT              1662
Val Ser Ala Leu Glu Cys Glu Ile Gln Leu Leu Lys Asn Leu Gln His
                        410                      415                  420

GAG CGC ATT GTG CAG TAC TAC GGC TGC CTG CGG GAC CGT GCT GAG AAG              1710
Glu Arg Ile Val Gln Tyr Tyr Gly Cys Leu Arg Asp Arg Ala Glu Lys
                425                          430                      435

ATC CTC ACC ATC TTT ATG GAG TAT ATG CCA GGG GGC TCT GTA AAA GAC              1758
Ile Leu Thr Ile Phe Met Glu Tyr Met Pro Gly Gly Ser Val Lys Asp
            440                          445                      450

CAG TTG AAG GCC TAC GGA GCT CTG ACA GAG AGT GTG ACC CGC AAG TAC              1806
Gln Leu Lys Ala Tyr Gly Ala Leu Thr Glu Ser Val Thr Arg Lys Tyr
    455                          460                      465

ACC CGG CAG ATT CTG GAG GGC ATG TCA TAC CTG CAC AGC AAC ATG ATT              1854
Thr Arg Gln Ile Leu Glu Gly Met Ser Tyr Leu His Ser Asn Met Ile
470                      475                      480                  485

GTG CAT CGG GAC ATC AAG GGA GCC AAT ATC CTC CGA GAC TCA GCT GGG              1902
Val His Arg Asp Ile Lys Gly Ala Asn Ile Leu Arg Asp Ser Ala Gly
                        490                      495                  500

AAT GTG AAG CTT GGG GAT TTT GGG GCC AGC AAA CGC CTA CAG ACC ATC              1950
Asn Val Lys Leu Gly Asp Phe Gly Ala Ser Lys Arg Leu Gln Thr Ile
                    505                      510                  515

TGC ATG TCA GGG ACA GGC ATT CGC TCT GTC ACT GGC ACA CCC TAC TGG              1998
Cys Met Ser Gly Thr Gly Ile Arg Ser Val Thr Gly Thr Pro Tyr Trp
            520                      525                  530

ATG AGT CCT GAA GTC ATC AGT GGC GAG GGC TAT GGA AGA AAG GCA GAC              2046
Met Ser Pro Glu Val Ile Ser Gly Glu Gly Tyr Gly Arg Lys Ala Asp
535                      540                  545

GTG TGG AGC CTG GGC TGT ACT GTG GTG GAA ATG CTG ACA GAG AAA CCA              2094
Val Trp Ser Leu Gly Cys Thr Val Val Glu Met Leu Thr Glu Lys Pro
550                      555                  560                      565

CCT TGG GCA GAG TAT GAA GCT ATG GCT GCC ATT TTC AAG ATT GCC ACC              2142
Pro Trp Ala Glu Tyr Glu Ala Met Ala Ala Ile Phe Lys Ile Ala Thr
                    570                  575                      580

CAG CCT ACC AAT CCT CAG CTG CCC TCT CAC ATC TCA GAA CAC GGC AGG              2190
Gln Pro Thr Asn Pro Gln Leu Pro Ser His Ile Ser Glu His Gly Arg
                585                  590                      595

GAC TTC CTG AGG CGC ATA TTT GTG GAA GCT CGT CAG AGA CCC TCA GCT              2238
Asp Phe Leu Arg Arg Ile Phe Val Glu Ala Arg Gln Arg Pro Ser Ala
            600                  605                      610

GAG GAG CTG CTC ACA CAC CAC TTT GCA CAG CTA GTG TAC TGAGCTCTCA               2287
Glu Glu Leu Leu Thr His His Phe Ala Gln Leu Val Tyr
615                  620                      625

AGGCTATCAG GCTGCCAGCT GCCACCTGCT GAGCAGGCAA GGGGCTGCTG TCAGGCTCAG           2347

TGAAGTTGCT GCTTCTTCCA GGCAAGGCTA TGACCAGTGG AGCATCGGTC CAGCCATTGT           2407

TTGTCTGTGC CCCATCTGCC ACTGGGACTC AAAGCCAGGA TGGGATAGCT CTGGCATCAA           2467
```

-continued

| | | | | | |
|---|---|---|---|---|---|
| GACTGGGAGC | TCCAGCCTGT | AAGACCCAAG | AGCTTTAGCA | CCTTAAGCTC | AGTATGGCGG | 2527 |
| GAAGGGCTGG | AAACAGTATG | CAAGACTGCC | ATGGGTCCTG | CCTACCCTCA | GATGTGTCCT | 2587 |
| AACACTGCAG | ACAGCACTGA | AGTCAAGAGG | GACTGGGGCA | CAGGAGGTCC | TCAAGGGTAT | 2647 |
| GAATAGTGTT | ACTTCATTCA | GAGTGTTACT | TTGTTTCTCT | CCCAATGTTT | GGAGACCACC | 2707 |
| AGCCTGTCTC | TGGGCTGCAA | GCCTGAGGTA | AAGCCCAGCA | TCCCCCAGCC | AACAGAAGGT | 2767 |
| AGAGGTTTGG | GCTACCCCAC | TATAGCTTCC | AGGTATTCGG | TGTCAGTCCT | GTCTTACCAA | 2827 |
| AGATGAATGA | AGCAAATGTT | ACACTGCCTT | ATTCTGGGAA | GGAGGAGCTA | CTCGGATAAG | 2887 |
| CAGGGCCTGA | GAGATGGAGC | TGCCTCCAGA | AACTGGGGAG | ACCCAGTCTT | GTCAATGCAA | 2947 |
| TTGTCTCTGT | TTTACAAGTT | GGAGTCACTC | TTATGCTGTT | CCCAGTTTTA | AAACTGGAGA | 3007 |
| CTTTGCCCTC | TGAGCTCTGG | AGACCCATGT | GGGCTTAGGC | TTGGACTGGA | TGGAAGAGCT | 3067 |
| GATGGCCTCT | GCCCCTGGCC | TG | | | | 3089 |

(2) INFORMATION FOR SEQ ID NO:6:

(i) SEQUENCE CHARACTERISTICS:
(A) LENGTH: 626 amino acids
(B) TYPE: amino acid
(D) TOPOLOGY: linear (ii) MOLECULE TYPE: protein (xi) SEQUENCE DESCRIPTION: SEQ ID NO:6:

| Met | Asp | Glu | Gln | Glu | Ala | Leu | Asp | Ser | Ile | Met | Lys | Asp | Leu | Val | Ala |
|---|---|---|---|---|---|---|---|---|---|---|---|---|---|---|---|
| 1 | | | | 5 | | | | | 10 | | | | | 15 | |

| Leu | Gln | Met | Ser | Arg | Arg | Thr | Arg | Leu | Ser | Gly | Tyr | Glu | Thr | Met | Lys |
|---|---|---|---|---|---|---|---|---|---|---|---|---|---|---|---|
| | | | 20 | | | | 25 | | | | | 30 | | | |

| Asn | Lys | Asp | Thr | Gly | His | Pro | Asn | Arg | Gln | Ser | Asp | Val | Arg | Ile | Lys |
|---|---|---|---|---|---|---|---|---|---|---|---|---|---|---|---|
| | | 35 | | | | | 40 | | | | 45 | | | | |

| Phe | Glu | His | Asn | Gly | Glu | Arg | Arg | Ile | Ile | Ala | Phe | Ser | Arg | Pro | Val |
|---|---|---|---|---|---|---|---|---|---|---|---|---|---|---|---|
| | 50 | | | | | 55 | | | | | 60 | | | | |

| Arg | Tyr | Glu | Asp | Val | Glu | His | Lys | Val | Thr | Thr | Val | Phe | Gly | Gln | Pro |
|---|---|---|---|---|---|---|---|---|---|---|---|---|---|---|---|
| 65 | | | | | 70 | | | | 75 | | | | | 80 | |

| Leu | Asp | Leu | His | Tyr | Met | Asn | Asn | Glu | Leu | Ser | Ile | Leu | Leu | Lys | Asn |
|---|---|---|---|---|---|---|---|---|---|---|---|---|---|---|---|
| | | | | 85 | | | | | 90 | | | | | 95 | |

| Gln | Asp | Asp | Leu | Asp | Lys | Ala | Ile | Asp | Ile | Leu | Asp | Arg | Ser | Ser | Ser |
|---|---|---|---|---|---|---|---|---|---|---|---|---|---|---|---|
| | | | 100 | | | | 105 | | | | 110 | | | | |

| Met | Lys | Ser | Leu | Arg | Ile | Leu | Leu | Leu | Ser | Gln | Asp | Arg | Asn | His | Thr |
|---|---|---|---|---|---|---|---|---|---|---|---|---|---|---|---|
| | | 115 | | | | | 120 | | | | 125 | | | | |

| Ser | Ser | Ser | Pro | His | Ser | Gly | Val | Ser | Arg | Gln | Val | Arg | Ile | Lys | Pro |
|---|---|---|---|---|---|---|---|---|---|---|---|---|---|---|---|
| | 130 | | | | | 135 | | | | | 140 | | | | |

| Ser | Gln | Ser | Ala | Gly | Asp | Ile | Asn | Thr | Ile | Tyr | Gln | Ala | Pro | Glu | Pro |
|---|---|---|---|---|---|---|---|---|---|---|---|---|---|---|---|
| 145 | | | | | 150 | | | | 155 | | | | | 160 | |

| Arg | Ser | Arg | His | Leu | Ser | Val | Ser | Ser | Gln | Asn | Pro | Gly | Arg | Ser | Ser |
|---|---|---|---|---|---|---|---|---|---|---|---|---|---|---|---|
| | | | | 165 | | | | | 170 | | | | | 175 | |

| Pro | Pro | Pro | Gly | Tyr | Val | Pro | Glu | Arg | Gln | Gln | His | Ile | Ala | Arg | Gln |
|---|---|---|---|---|---|---|---|---|---|---|---|---|---|---|---|
| | | | 180 | | | | 185 | | | | | 190 | | | |

| Gly | Ser | Tyr | Thr | Ser | Ile | Asn | Ser | Glu | Gly | Glu | Phe | Ile | Pro | Glu | Thr |
|---|---|---|---|---|---|---|---|---|---|---|---|---|---|---|---|
| | | 195 | | | | | 200 | | | | 205 | | | | |

| Ser | Glu | Gln | Cys | Met | Leu | Asp | Pro | Leu | Ser | Ser | Ala | Glu | Asn | Ser | Leu |
|---|---|---|---|---|---|---|---|---|---|---|---|---|---|---|---|
| | 210 | | | | | 215 | | | | | 220 | | | | |

| Ser | Gly | Ser | Cys | Gln | Ser | Leu | Asp | Arg | Ser | Ala | Asp | Ser | Pro | Ser | Phe |
|---|---|---|---|---|---|---|---|---|---|---|---|---|---|---|---|
| 225 | | | | | 230 | | | | 235 | | | | | 240 | |

| Arg | Lys | Ser | Gln | Met | Ser | Arg | Ala | Arg | Ser | Phe | Pro | Asp | Asn | Arg | Lys |

|     |     |     |     | 245 |     |     |     | 250 |     |     |     | 255 |     |
| --- | --- | --- | --- | --- | --- | --- | --- | --- | --- | --- | --- | --- | --- |
| Glu | Cys | Ser | Asp | Arg | Glu | Thr | Gln | Leu | Tyr | Asp | Lys | Gly | Val | Lys | Gly |
|     |     |     | 260 |     |     |     | 265 |     |     |     | 270 |     |     |
| Gly | Thr | Tyr | Pro | Arg | Arg | Tyr | His | Val | Ser | Val | His | His | Lys | Asp | Tyr |
|     |     | 275 |     |     |     | 280 |     |     |     | 285 |     |     |     |
| Asn | Asp | Gly | Arg | Arg | Thr | Phe | Pro | Arg | Ile | Arg | Arg | His | Gln | Gly | Asn |
|     | 290 |     |     |     | 295 |     |     |     | 300 |     |     |     |
| Leu | Phe | Thr | Leu | Val | Pro | Ser | Ser | Arg | Ser | Leu | Ser | Thr | Asn | Gly | Glu |
| 305 |     |     |     |     | 310 |     |     |     | 315 |     |     |     | 320 |
| Asn | Met | Gly | Val | Ala | Val | Gln | Tyr | Leu | Asp | Pro | Arg | Gly | Arg | Leu | Arg |
|     |     |     |     | 325 |     |     |     | 330 |     |     |     | 335 |     |
| Ser | Ala | Asp | Ser | Glu | Asn | Ala | Leu | Thr | Val | Gln | Glu | Arg | Asn | Val | Pro |
|     |     |     | 340 |     |     |     | 345 |     |     |     | 350 |     |     |
| Thr | Lys | Ser | Pro | Ser | Ala | Pro | Ile | Asn | Trp | Arg | Arg | Gly | Lys | Leu | Leu |
|     |     | 355 |     |     |     | 360 |     |     |     | 365 |     |     |     |
| Gly | Gln | Gly | Ala | Phe | Gly | Arg | Val | Tyr | Leu | Cys | Tyr | Asp | Val | Asp | Thr |
|     | 370 |     |     |     | 375 |     |     |     | 380 |     |     |     |
| Gly | Arg | Glu | Leu | Ala | Ser | Lys | Gln | Val | Gln | Phe | Asp | Pro | Asp | Ser | Pro |
| 385 |     |     |     | 390 |     |     |     | 395 |     |     |     | 400 |
| Glu | Thr | Ser | Lys | Glu | Val | Ser | Ala | Leu | Glu | Cys | Glu | Ile | Gln | Leu | Leu |
|     |     |     | 405 |     |     |     | 410 |     |     |     | 415 |     |
| Lys | Asn | Leu | Gln | His | Glu | Arg | Ile | Val | Gln | Tyr | Tyr | Gly | Cys | Leu | Arg |
|     |     |     | 420 |     |     |     | 425 |     |     |     | 430 |     |
| Asp | Arg | Ala | Glu | Lys | Ile | Leu | Thr | Ile | Phe | Met | Glu | Tyr | Met | Pro | Gly |
|     |     | 435 |     |     |     | 440 |     |     |     | 445 |     |     |
| Gly | Ser | Val | Lys | Asp | Gln | Leu | Lys | Ala | Tyr | Gly | Ala | Leu | Thr | Glu | Ser |
|     | 450 |     |     |     | 455 |     |     |     | 460 |     |     |     |
| Val | Thr | Arg | Lys | Tyr | Thr | Arg | Gln | Ile | Leu | Glu | Gly | Met | Ser | Tyr | Leu |
| 465 |     |     |     | 470 |     |     |     | 475 |     |     |     | 480 |
| His | Ser | Asn | Met | Ile | Val | His | Arg | Asp | Ile | Lys | Gly | Ala | Asn | Ile | Leu |
|     |     |     | 485 |     |     |     | 490 |     |     |     | 495 |     |
| Arg | Asp | Ser | Ala | Gly | Asn | Val | Lys | Leu | Gly | Asp | Phe | Gly | Ala | Ser | Lys |
|     |     |     | 500 |     |     |     | 505 |     |     |     | 510 |     |
| Arg | Leu | Gln | Thr | Ile | Cys | Met | Ser | Gly | Thr | Gly | Ile | Arg | Ser | Val | Thr |
|     |     | 515 |     |     |     | 520 |     |     |     | 525 |     |     |
| Gly | Thr | Pro | Tyr | Trp | Met | Ser | Pro | Glu | Val | Ile | Ser | Gly | Glu | Gly | Tyr |
|     | 530 |     |     |     | 535 |     |     |     | 540 |     |     |     |
| Gly | Arg | Lys | Ala | Asp | Val | Trp | Ser | Leu | Gly | Cys | Thr | Val | Val | Glu | Met |
| 545 |     |     |     | 550 |     |     |     | 555 |     |     |     | 560 |
| Leu | Thr | Glu | Lys | Pro | Pro | Trp | Ala | Glu | Tyr | Glu | Ala | Met | Ala | Ala | Ile |
|     |     |     | 565 |     |     |     | 570 |     |     |     | 575 |     |
| Phe | Lys | Ile | Ala | Thr | Gln | Pro | Thr | Asn | Pro | Gln | Leu | Pro | Ser | His | Ile |
|     |     | 580 |     |     |     | 585 |     |     |     | 590 |     |     |
| Ser | Glu | His | Gly | Arg | Asp | Phe | Leu | Arg | Arg | Ile | Phe | Val | Glu | Ala | Arg |
|     |     | 595 |     |     |     | 600 |     |     |     | 605 |     |     |
| Gln | Arg | Pro | Ser | Ala | Glu | Glu | Leu | Leu | Thr | His | His | Phe | Ala | Gln | Leu |
|     | 610 |     |     |     | 615 |     |     |     | 620 |     |     |     |
| Val | Tyr |
| 625 |     |

( 2 ) INFORMATION FOR SEQ ID NO:7:

( i ) SEQUENCE CHARACTERISTICS:
( A ) LENGTH: 3913 base pairs
( B ) TYPE: nucleic acid -continued (C) STRANDEDNESS: double
(D) TOPOLOGY: linear ( i i ) MOLECULE TYPE: cDNA ( i x ) FEATURE:
  (A) NAME/KEY: CDS
  (B) LOCATION: 747..3417
  (A) NAME/KEY: N = G,A,C or T
  (B) LOCATION: 1094
  (A) NAME/KEY: Xaa = Any amino acid
  (B) LOCATION: 116

( x i ) SEQUENCE DESCRIPTION: SEQ ID NO:7:

```
AATTCGGCAC GAGAACCTAT CAGACATTGG CTGGCCAGTG TTTGAAATCC CCTCCCCTCG      60

GCCGTCCAAG GGCTACGAGC CAGAGGACGA GGTCGAGGAC ACGGAGGTTG AGCTGAGGGA     120

GCTGGAGAGC GGGACGGAGG AGAGTGACGA GGAGCCAACC CCCAGTCCGA GGGTGCCAGA     180

GCTCAGGCTG TCCACAGACA CCATCTTGGA CAGTCGCTCC CAGGGCTGCG TCTCCAGGAA     240

GCTGGAGAGG CTCGAGTCAG AGGAAGATTC CATAGGCTGG GGGACAGCGG ACTGTGGCCC     300

TGAAGCCAGC AGGCATTGTT TGACTTCTAT CTATAGACCA TTCGTGGACA AGCACTGAA      360

GCAAATGGGG CTAAGAAAGT TAATTTTACG ACTTCATAAG CTTATGAATG GGTCCTTGCA     420

AAGAGCTCGT GTAGCTCTGG TGAAGGACGA CCGTCAGTGG AGTTCTCTGA CTTTCCAGGT     480

CCCATGTGGG GCTCGGATTA TGTGCAGTTG TCGGGAACAC CTCCTTCCTC AGAGCAGAAG     540

TGTAGCGCTG TGTCCTGGGA AGAACTGAGA GCCATGGACC TGCCTTCCTT TGAGCCCGCC     600

TTCCTGGTGC TCTGTCGGGT CCTGCTGAAC GTGATCCACG AGTGCCTGAA GCTGCGGCTG     660

GAACAGAGGC TGCCGGGGAG CCTTCCCTCT TGAGTATCAA ACAGCTAGTG CGAGAGTGTA     720
```

| AAGAGGTCCT | AAAGGGCGGG | CTCCTG | ATG<br>Met<br>1 | AAG<br>Lys | CAG<br>Gln | TAT<br>Tyr | TAC<br>Tyr | CAG<br>Gln | TTC<br>Phe | ATG<br>Met | CTG<br>Leu<br>5 | 773 |
|---|---|---|---|---|---|---|---|---|---|---|---|---|
| CAG<br>Gln | GAG<br>Glu<br>10 | GTC<br>Val | CTG<br>Leu | GGC<br>Gly | GGA<br>Gly<br>15 | CTG<br>Leu | GAG<br>Glu | AAG<br>Lys | ACC<br>Thr | GAC<br>Asp<br>20 | TGC<br>Cys | AAC<br>Asn | ATG<br>Met | GAT<br>Asp | GCC<br>Ala<br>25 | 821 |
| TTT<br>Phe | GAG<br>Glu | GAG<br>Glu | GAC<br>Asp | CTG<br>Leu<br>30 | CAG<br>Gln | AAG<br>Lys | ATG<br>Met | CTG<br>Leu | ATG<br>Met<br>35 | GTG<br>Val | TAT<br>Tyr | TTT<br>Phe | GAT<br>Asp | TAC<br>Tyr<br>40 | ATG<br>Met | 869 |
| AGA<br>Arg | AGC<br>Ser | TGG<br>Trp | ATC<br>Ile<br>45 | CAA<br>Gln | ATG<br>Met | CTA<br>Leu | CAG<br>Gln | CAG<br>Gln<br>50 | TTA<br>Leu | CCT<br>Pro | CAG<br>Gln | GCT<br>Ala | TCC<br>Ser<br>55 | CAT<br>His | AGC<br>Ser | 917 |
| TTA<br>Leu | AAA<br>Lys | AAC<br>Asn<br>60 | CTG<br>Leu | CTA<br>Leu | GAA<br>Glu | GAG<br>Glu | GAA<br>Glu<br>65 | TGG<br>Trp | AAT<br>Asn | TTC<br>Phe | ACC<br>Thr | AAA<br>Lys<br>70 | GAA<br>Glu | ATA<br>Ile | ACC<br>Thr | 965 |
| CAT<br>His | TAT<br>Tyr<br>75 | ATC<br>Ile | CGT<br>Arg | GGC<br>Gly | GGA<br>Gly | GAA<br>Glu<br>80 | GCG<br>Ala | CAG<br>Gln | GCT<br>Ala | GGA<br>Gly | AAG<br>Lys<br>85 | CTT<br>Leu | TTC<br>Phe | TGT<br>Cys | GAC<br>Asp | 1013 |
| ATC<br>Ile<br>90 | GCA<br>Ala | GGG<br>Gly | ATG<br>Met | CTG<br>Leu | CTG<br>Leu<br>95 | AAA<br>Lys | TCC<br>Ser | ACA<br>Thr | GGG<br>Gly | AGC<br>Ser<br>100 | TTT<br>Phe | CTG<br>Leu | GAA<br>Glu | TCC<br>Ser | GGC<br>Gly<br>105 | 1061 |
| CTG<br>Leu | CAG<br>Gln | GAG<br>Glu | AGC<br>Ser<br>110 | TGT<br>Cys | GCT<br>Ala | GAG<br>Glu | CTG<br>Leu | TGG<br>Trp<br>115 | ACC<br>Thr | AGN<br>Xaa | GCC<br>Ala | GAC<br>Asp | GAC<br>Asp<br>120 | AAC<br>Asn | GGT<br>Gly | 1109 |
| GCT<br>Ala | GCC<br>Ala | GAC<br>Asp<br>125 | GAG<br>Glu | CTA<br>Leu | AGG<br>Arg | AGA<br>Arg | TCT<br>Ser<br>130 | GTC<br>Val | ATC<br>Ile | GAG<br>Glu | ATC<br>Ile | AGC<br>Ser<br>135 | CGA<br>Arg | GCA<br>Ala | CTC<br>Leu | 1157 |
| AAG<br>Lys | GAG<br>Glu<br>140 | CTC<br>Leu | TTC<br>Phe | CAC<br>His | GAA<br>Glu | GCC<br>Ala<br>145 | AGG<br>Arg | GAA<br>Glu | AGA<br>Arg | GCC<br>Ala | TCC<br>Ser<br>150 | AAG<br>Lys | GCC<br>Ala | CTG<br>Leu | GGC<br>Gly | 1205 |
| TTT<br>Phe | GCT<br>Ala | AAA<br>Lys | ATG<br>Met | CTG<br>Leu | AGG<br>Arg | AAG<br>Lys | GAC<br>Asp | CTA<br>Leu | GAA<br>Glu | ATA<br>Ile | GCA<br>Ala | GCA<br>Ala | GAG<br>Glu | TTC<br>Phe | GTG<br>Val | 1253 |

```
              Phe   Ala   Lys   Met   Leu   Arg   Lys   Asp   Leu   Glu   Ile   Ala   Ala   Glu   Phe   Val
                    155                     160                     165

CTA   TCT   GCA   TCA   GCC   CGA   GAG   CTC   CTG   GAC   GCT   CTG   AAA   GCA   AAG   CAG                1301
Leu   Ser   Ala   Ser   Ala   Arg   Glu   Leu   Leu   Asp   Ala   Leu   Lys   Ala   Lys   Gln
170                     175                     180                     185

TAT   GTT   AAG   GTA   CAG   ATT   CCC   GGG   TTA   GAG   AAT   TTG   CAC   GTG   TTT   GTC                1349
Tyr   Val   Lys   Val   Gln   Ile   Pro   Gly   Leu   Glu   Asn   Leu   His   Val   Phe   Val
                        190                     195                     200

CCC   GAC   AGC   CTC   GCT   GAG   GAG   AAG   AAA   ATT   ATT   TTG   CAG   CTA   CTC   AAT                1397
Pro   Asp   Ser   Leu   Ala   Glu   Glu   Lys   Lys   Ile   Ile   Leu   Gln   Leu   Leu   Asn
                  205                     210                     215

GCT   GCC   ACA   GGA   AAG   GAC   TGC   TCA   AAG   GAT   CCA   GAC   GAC   GTC   TTC   ATG                1445
Ala   Ala   Thr   Gly   Lys   Asp   Cys   Ser   Lys   Asp   Pro   Asp   Asp   Val   Phe   Met
            220                     225                     230

GAT   GCC   TTC   CTG   CTC   CTG   ACC   AAG   CAT   GGG   GAC   CGA   GCC   CGT   GAC   TCA                1493
Asp   Ala   Phe   Leu   Leu   Leu   Thr   Lys   His   Gly   Asp   Arg   Ala   Arg   Asp   Ser
      235                     240                     245

GAA   GAT   GGC   TGG   GGC   ACA   TGG   GAA   GCT   CGG   GCT   GTC   AAA   ATT   GTG   CCT                1541
Glu   Asp   Gly   Trp   Gly   Thr   Trp   Glu   Ala   Arg   Ala   Val   Lys   Ile   Val   Pro
250                     255                     260                     265

CAG   GTG   GAG   ACT   GTG   GAC   ACC   CTG   AGA   AGC   ATG   CAG   GTG   GAC   AAC   CTT                1589
Gln   Val   Glu   Thr   Val   Asp   Thr   Leu   Arg   Ser   Met   Gln   Val   Asp   Asn   Leu
                        270                     275                     280

CTG   CTG   GTT   GTC   ATG   GAG   TCT   GCT   CAC   CTC   GTA   CTT   CAG   AGA   AAA   GCC                1637
Leu   Leu   Val   Val   Met   Glu   Ser   Ala   His   Leu   Val   Leu   Gln   Arg   Lys   Ala
                  285                     290                     295

TTC   CAG   CAG   TCC   ATT   GAG   GGG   CTG   ATG   ACT   GTA   CGC   CAT   GAG   CAG   ACA                1685
Phe   Gln   Gln   Ser   Ile   Glu   Gly   Leu   Met   Thr   Val   Arg   His   Glu   Gln   Thr
            300                     305                     310

TCT   AGC   CAG   CCC   ATC   ATC   GCC   AAA   GGT   TTG   CAG   CAG   CTC   AAG   AAC   GAT                1733
Ser   Ser   Gln   Pro   Ile   Ile   Ala   Lys   Gly   Leu   Gln   Gln   Leu   Lys   Asn   Asp
      315                     320                     325

GCA   CTT   GAG   CTA   TGC   AAC   AGA   ATC   AGC   GAT   GCC   ATC   GAC   CGT   GTG   GAC                1781
Ala   Leu   Glu   Leu   Cys   Asn   Arg   Ile   Ser   Asp   Ala   Ile   Asp   Arg   Val   Asp
330                     335                     340                     345

CAC   ATG   TTC   ACC   CTG   GAG   TTC   GAT   GCT   GAG   GTC   GAG   GAG   TCT   GAG   TCG                1829
His   Met   Phe   Thr   Leu   Glu   Phe   Asp   Ala   Glu   Val   Glu   Glu   Ser   Glu   Ser
                        350                     355                     360

GCC   ACG   CTG   CAG   CAG   TAC   TAC   CGA   GAA   GCC   ATG   ATT   CAG   GGC   TAC   AAC                1877
Ala   Thr   Leu   Gln   Gln   Tyr   Tyr   Arg   Glu   Ala   Met   Ile   Gln   Gly   Tyr   Asn
                  365                     370                     375

TTT   GGG   TTT   GAG   TAT   CAT   AAA   GAA   GTT   GTT   CGT   TTG   ATG   TCT   GGG   GAA                1925
Phe   Gly   Phe   Glu   Tyr   His   Lys   Glu   Val   Val   Arg   Leu   Met   Ser   Gly   Glu
            380                     385                     390

TTC   AGG   CAG   AAG   ATA   GGA   GAC   AAA   TAT   ATA   ACG   TTC   GCC   CAG   AAG   TGG                1973
Phe   Arg   Gln   Lys   Ile   Gly   Asp   Lys   Tyr   Ile   Thr   Phe   Ala   Gln   Lys   Trp
      395                     400                     405

ATG   AAT   TAC   GTG   CTG   ACC   AAA   TGC   GAG   AGC   GGC   AGA   GGC   ACA   AGA   CCC                2021
Met   Asn   Tyr   Val   Leu   Thr   Lys   Cys   Glu   Ser   Gly   Arg   Gly   Thr   Arg   Pro
410                     415                     420                     425

AGA   TGG   GCC   ACC   CAA   GGA   TTT   GAT   TTC   CTA   CAA   GCC   ATT   GAA   CCT   GCC                2069
Arg   Trp   Ala   Thr   Gln   Gly   Phe   Asp   Phe   Leu   Gln   Ala   Ile   Glu   Pro   Ala
                        430                     435                     440

TTT   ATT   TCA   GCT   TTA   CCA   GAA   GAT   GAC   TTC   TTG   AGT   TTG   CAA   GCC   CTG                2117
Phe   Ile   Ser   Ala   Leu   Pro   Glu   Asp   Asp   Phe   Leu   Ser   Leu   Gln   Ala   Leu
                  445                     450                     455

ATG   AAT   GAG   TGC   ATC   GGG   CAC   GTC   ATA   GGA   AAG   CCA   CAC   AGC   CCT   GTC                2165
Met   Asn   Glu   Cys   Ile   Gly   His   Val   Ile   Gly   Lys   Pro   His   Ser   Pro   Val
            460                     465                     470

ACA   GCT   ATC   CAT   CGG   AAC   AGC   CCC   CGC   CCT   GTG   AAG   GTG   CCC   CGA   TGC                2213
```

|     |     |     |     |     |     |     |     |     |     |     |     |     |     |     |      |
|-----|-----|-----|-----|-----|-----|-----|-----|-----|-----|-----|-----|-----|-----|-----|------|
| Thr | Ala | Ile | His | Arg | Asn | Ser | Pro | Arg | Pro | Val | Lys | Val | Pro | Arg | Cys  |
| 475 |     |     |     |     | 480 |     |     |     |     | 485 |     |     |     |     |      |
| CAC | AGT | GAC | CCT | CCT | AAC | CCT | CAC | CTC | ATC | ATC | CCG | ACT | CCA | GAG | GGA  | 2261 |
| His | Ser | Asp | Pro | Pro | Asn | Pro | His | Leu | Ile | Ile | Pro | Thr | Pro | Glu | Gly  |
| 490 |     |     |     |     | 495 |     |     |     | 500 |     |     |     |     |     | 505  |
| TTC | AGG | GGT | TCC | AGT | GTC | CCT | GAA | AAC | GAC | CGC | TTG | GCC | TCC | ATA | GCT  | 2309 |
| Phe | Arg | Gly | Ser | Ser | Val | Pro | Glu | Asn | Asp | Arg | Leu | Ala | Ser | Ile | Ala  |
|     |     |     |     | 510 |     |     |     |     | 515 |     |     |     |     | 520 |      |
| GCA | GAA | CTG | CAG | TTC | AGG | TCT | CTG | AGT | CGG | CAC | TCA | AGC | CCC | ACG | GAA  | 2357 |
| Ala | Glu | Leu | Gln | Phe | Arg | Ser | Leu | Ser | Arg | His | Ser | Ser | Pro | Thr | Glu  |
|     |     |     | 525 |     |     |     |     | 530 |     |     |     |     | 535 |     |      |
| GAG | CGA | GAC | GAG | CCA | GCG | TAT | CCT | CGG | AGT | GAC | TCA | AGT | GGA | TCA | ACT  | 2405 |
| Glu | Arg | Asp | Glu | Pro | Ala | Tyr | Pro | Arg | Ser | Asp | Ser | Ser | Gly | Ser | Thr  |
|     | 540 |     |     |     |     | 545 |     |     |     |     | 550 |     |     |     |      |
| CGG | AGA | AGC | TGG | GAA | CTT | CGA | ACA | CTC | ATC | AGC | CAG | ACC | AAA | GAC | TCG  | 2453 |
| Arg | Arg | Ser | Trp | Glu | Leu | Arg | Thr | Leu | Ile | Ser | Gln | Thr | Lys | Asp | Ser  |
| 555 |     |     |     |     |     | 560 |     |     |     |     | 565 |     |     |     |      |
| GCC | TCT | AAG | CAG | GGG | CCC | ATA | GAA | GCT | ATC | CAG | AAG | TCA | GTC | CGA | CTG  | 2501 |
| Ala | Ser | Lys | Gln | Gly | Pro | Ile | Glu | Ala | Ile | Gln | Lys | Ser | Val | Arg | Leu  |
| 570 |     |     |     |     | 575 |     |     |     |     | 580 |     |     |     |     | 585  |
| TTT | GAA | GAG | AGG | AGG | TAT | CGA | GAG | ATG | AGG | AGA | AAG | AAT | ATC | ATC | GGC  | 2549 |
| Phe | Glu | Glu | Arg | Arg | Tyr | Arg | Glu | Met | Arg | Arg | Lys | Asn | Ile | Ile | Gly  |
|     |     |     |     | 590 |     |     |     |     | 595 |     |     |     |     |     | 600  |
| CAA | GTG | TGC | GAT | ACC | CCT | AAG | TCC | TAT | GAT | AAC | GTC | ATG | CAT | GTT | GGA  | 2597 |
| Gln | Val | Cys | Asp | Thr | Pro | Lys | Ser | Tyr | Asp | Asn | Val | Met | His | Val | Gly  |
|     |     |     | 605 |     |     |     |     | 610 |     |     |     |     | 615 |     |      |
| CTG | AGG | AAG | GTG | ACA | TTT | AAG | TGG | CAA | AGA | GGA | AAC | AAA | ATT | GGA | GAA  | 2645 |
| Leu | Arg | Lys | Val | Thr | Phe | Lys | Trp | Gln | Arg | Gly | Asn | Lys | Ile | Gly | Glu  |
|     |     | 620 |     |     |     |     | 625 |     |     |     |     | 630 |     |     |      |
| GGA | CAG | TAT | GGA | AAA | GTA | TAC | ACC | TGC | ATC | AGT | GTT | GAC | ACA | GGG | GAG  | 2693 |
| Gly | Gln | Tyr | Gly | Lys | Val | Tyr | Thr | Cys | Ile | Ser | Val | Asp | Thr | Gly | Glu  |
|     | 635 |     |     |     |     | 640 |     |     |     |     | 645 |     |     |     |      |
| CTG | ATG | GCC | ATG | AAG | GAG | ATT | CGA | TTT | CAG | CCT | AAC | GAC | CAC | AAG | ACT  | 2741 |
| Leu | Met | Ala | Met | Lys | Glu | Ile | Arg | Phe | Gln | Pro | Asn | Asp | His | Lys | Thr  |
| 650 |     |     |     | 655 |     |     |     |     | 660 |     |     |     |     | 665 |      |
| ATC | AAG | GAG | ACT | GCA | GAC | GAG | TTG | AAA | ATA | TTT | GAA | GGC | ATC | AAG | CAC  | 2789 |
| Ile | Lys | Glu | Thr | Ala | Asp | Glu | Leu | Lys | Ile | Phe | Glu | Gly | Ile | Lys | His  |
|     |     |     |     | 670 |     |     |     | 675 |     |     |     |     |     | 680 |      |
| CCC | AAC | CTG | GTC | CGG | TAT | TTT | GGC | GTG | GAG | CTT | CAC | AGG | GAA | GAG | ATG  | 2837 |
| Pro | Asn | Leu | Val | Arg | Tyr | Phe | Gly | Val | Glu | Leu | His | Arg | Glu | Glu | Met  |
|     |     |     | 685 |     |     |     |     | 690 |     |     |     |     | 695 |     |      |
| TAC | ATC | TTC | ATG | GAG | TAC | TGT | GAT | GAG | GGT | ACA | CTA | GAG | GAG | GTG | TCA  | 2885 |
| Tyr | Ile | Phe | Met | Glu | Tyr | Cys | Asp | Glu | Gly | Thr | Leu | Glu | Glu | Val | Ser  |
|     |     | 700 |     |     |     |     | 705 |     |     |     |     | 710 |     |     |      |
| CGA | CTG | GGC | CTG | CAG | GAG | CAC | GTC | ATC | AGG | TTA | TAT | ACC | AAG | CAG | ATC  | 2933 |
| Arg | Leu | Gly | Leu | Gln | Glu | His | Val | Ile | Arg | Leu | Tyr | Thr | Lys | Gln | Ile  |
| 715 |     |     |     |     | 720 |     |     |     |     | 725 |     |     |     |     |      |
| ACT | GTC | GCC | ATC | AAC | GTC | CTC | CAT | GAG | CAC | GGC | ATC | GTT | CAC | CGA | GAC  | 2981 |
| Thr | Val | Ala | Ile | Asn | Val | Leu | His | Glu | His | Gly | Ile | Val | His | Arg | Asp  |
| 730 |     |     |     |     | 735 |     |     |     |     | 740 |     |     |     |     | 745  |
| ATC | AAA | GGT | GCC | AAT | ATC | TTC | CTT | ACG | TCA | TCT | GGA | CTA | ATC | AAG | CTG  | 3029 |
| Ile | Lys | Gly | Ala | Asn | Ile | Phe | Leu | Thr | Ser | Ser | Gly | Leu | Ile | Lys | Leu  |
|     |     |     |     | 750 |     |     |     |     | 755 |     |     |     |     | 760 |      |
| GGA | GAT | TTT | GGA | TGC | TCT | GTA | AAA | CTT | AAA | AAC | AAC | GCC | CAG | ACC | ATG  | 3077 |
| Gly | Asp | Phe | Gly | Cys | Ser | Val | Lys | Leu | Lys | Asn | Asn | Ala | Gln | Thr | Met  |
|     |     |     | 765 |     |     |     |     | 770 |     |     |     |     | 775 |     |      |
| CCC | GGA | GAG | GTG | AAC | AGC | ACC | CTA | GGG | ACA | GCA | GCT | TAC | ATG | GCC | CCT  | 3125 |
| Pro | Gly | Glu | Val | Asn | Ser | Thr | Leu | Gly | Thr | Ala | Ala | Tyr | Met | Ala | Pro  |
|     | 780 |     |     |     |     | 785 |     |     |     |     | 790 |     |     |     |      |
| GAA | GTT | ATT | ACC | CGA | GCC | AAA | GGA | GAA | GGC | CAC | GGA | CGT | GCG | GCA | GAT  | 3173 |

-continued

| | | | | | | | | | | | | | | | | |
|---|---|---|---|---|---|---|---|---|---|---|---|---|---|---|---|---|
|Glu|Val|Ile|Thr|Arg|Ala|Lys|Gly|Glu|Gly|His|Gly|Arg|Ala|Ala|Asp| |
| |795| | | |800| | | |805| | | | | | | |

| | | | | | | | | | | | | | | | | |
|---|---|---|---|---|---|---|---|---|---|---|---|---|---|---|---|---|
|ATC|TGG|AGT|CTG|GGG|TGC|GTC|GTC|ATA|GAG|ATG|GTG|ACT|GGC|AAG|CGG|3221|
|Ile|Trp|Ser|Leu|Gly|Cys|Val|Val|Ile|Glu|Met|Val|Thr|Gly|Lys|Arg| |
|810| | | | |815| | | | |820| | | | |825| |

| | | | | | | | | | | | | | | | | |
|---|---|---|---|---|---|---|---|---|---|---|---|---|---|---|---|---|
|CCT|TGG|CAT|GAG|TAT|GAA|CAC|AAC|TTT|CAG|ATT|ATG|TAC|AAG|GTG|GGG|3269|
|Pro|Trp|His|Glu|Tyr|Glu|His|Asn|Phe|Gln|Ile|Met|Tyr|Lys|Val|Gly| |
| | | | |830| | | | |835| | | | |840| | |

| | | | | | | | | | | | | | | | | |
|---|---|---|---|---|---|---|---|---|---|---|---|---|---|---|---|---|
|ATG|GGA|CAC|AAG|CCA|CCA|ATC|CCG|GAA|AGG|CTA|AGC|CCT|GAA|GGA|AAG|3317|
|Met|Gly|His|Lys|Pro|Pro|Ile|Pro|Glu|Arg|Leu|Ser|Pro|Glu|Gly|Lys| |
| | | |845| | | | |850| | | | |855| | | |

| | | | | | | | | | | | | | | | | |
|---|---|---|---|---|---|---|---|---|---|---|---|---|---|---|---|---|
|GCC|TTT|CTC|TCG|CAC|TGC|CTG|GAA|AGT|GAC|CCG|AAG|ATA|CGG|TGG|ACA|3365|
|Ala|Phe|Leu|Ser|His|Cys|Leu|Glu|Ser|Asp|Pro|Lys|Ile|Arg|Trp|Thr| |
| | | | |860| | | | |865| | | | |870| | |

| | | | | | | | | | | | | | | | | |
|---|---|---|---|---|---|---|---|---|---|---|---|---|---|---|---|---|
|GCC|AGC|CAG|CTC|CTC|GAC|CAC|GCT|TTT|GTC|AAG|GTT|TGC|ACA|GAT|GAA|3413|
|Ala|Ser|Gln|Leu|Leu|Asp|His|Ala|Phe|Val|Lys|Val|Cys|Thr|Asp|Glu| |
| |875| | | | |880| | | | |885| | | | | |

| | | |
|---|---|---|
|GAG|T GAAGTGAACC AGTCCGTGGC CTAGTAGTGT GTGGACAGAA TCCCGTGATC|3467|
|Glu| | |
|890| | |

ACTACTGTAT GTAATATTTA CATAAAGACT GCAGCGCAGG CGGCCTTCCT AACCTCCCAG    3527

GACTGAAGAC TACAGGGGTG ACAAGCCTCA CTTCTGCTGC TCCTGTCGCC TGCTGAGTGA    3587

CAGTGCTGAG GTTAAAGGAG CCGCACGTTA AGTGCCATTA CTACTGTACA CGGCCACCGC    3647

CTCTGTCCCC TCCGACCCTC TCGTGACTGA GAACCAACCG TGTCATCAGC ACAGTGTTTT    3707

TGAGCTCCTG GGGTTCAGAA GAACATGTAG TGTTCCGGG TGTCCGGGAC GTTTATTTCA     3767

ACCTCCTGGT CGTTGGCTCT GACTGTGGAG CCTCCTTGTT CGAAAGCTGC AGGTTTGTTA    3827

TGCAAAGGCT CGTAAGTGAA GCTGAAGAAA AGGTTCTTTT TCAATAAATG GTTTATTTTA    3887

GGAAAGCGAA AAAAAAAAAA AAAAAA                                        3913

( 2 ) INFORMATION FOR SEQ ID NO:8:

( i ) SEQUENCE CHARACTERISTICS:
  ( A ) LENGTH: 890 amino acids
  ( B ) TYPE: amino acid
  ( D ) TOPOLOGY: linear ( i i ) MOLECULE TYPE: protein ( i x ) FEATURE:
  ( A ) NAME/KEY: Xaa = Any amino acid
  ( B ) LOCATION: 116

( x i ) SEQUENCE DESCRIPTION: SEQ ID NO:8:

| | | | | | | | | | | | | | | |
|---|---|---|---|---|---|---|---|---|---|---|---|---|---|---|
|Met|Lys|Gln|Tyr|Tyr|Gln|Phe|Met|Leu|Gln|Glu|Val|Leu|Gly|Gly|Leu|
|1| | | |5| | | | |10| | | | |15| |

| | | | | | | | | | | | | | | |
|---|---|---|---|---|---|---|---|---|---|---|---|---|---|---|
|Glu|Lys|Thr|Asp|Cys|Asn|Met|Asp|Ala|Phe|Glu|Glu|Asp|Leu|Gln|Lys|
| | | |20| | | | |25| | | | |30| | |

| | | | | | | | | | | | | | | |
|---|---|---|---|---|---|---|---|---|---|---|---|---|---|---|
|Met|Leu|Met|Val|Tyr|Phe|Asp|Tyr|Met|Arg|Ser|Trp|Ile|Gln|Met|Leu|
| | |35| | | | |40| | | | |45| | | |

| | | | | | | | | | | | | | | |
|---|---|---|---|---|---|---|---|---|---|---|---|---|---|---|
|Gln|Gln|Leu|Pro|Gln|Ala|Ser|His|Ser|Leu|Lys|Asn|Leu|Leu|Glu|Glu|
| |50| | | | |55| | | | |60| | | | |

| | | | | | | | | | | | | | | |
|---|---|---|---|---|---|---|---|---|---|---|---|---|---|---|
|Glu|Trp|Asn|Phe|Thr|Lys|Glu|Ile|Thr|His|Tyr|Ile|Arg|Gly|Gly|Glu|
|65| | | | |70| | | | |75| | | | |80|

| | | | | | | | | | | | | | | |
|---|---|---|---|---|---|---|---|---|---|---|---|---|---|---|
|Ala|Gln|Ala|Gly|Lys|Leu|Phe|Cys|Asp|Ile|Ala|Gly|Met|Leu|Leu|Lys|
| | | | |85| | | | |90| | | | |95| |

| | | | | | | | | | | | | |
|---|---|---|---|---|---|---|---|---|---|---|---|---|
|Ser|Thr|Gly|Ser|Phe|Leu|Glu|Ser|Gly|Leu|Gln|Glu|Ser|Cys|Ala|Glu|
| | | | |100| | | | |105| | | | |110| |

```
Leu Trp Thr Xaa Ala Asp Asp Asn Gly Ala Ala Asp Glu Leu Arg Arg
        115             120                 125

Ser Val Ile Glu Ile Ser Arg Ala Leu Lys Glu Leu Phe His Glu Ala
    130             135             140

Arg Glu Arg Ala Ser Lys Ala Leu Gly Phe Ala Lys Met Leu Arg Lys
145             150             155                 160

Asp Leu Glu Ile Ala Ala Glu Phe Val Leu Ser Ala Ser Ala Arg Glu
                165             170             175

Leu Leu Asp Ala Leu Lys Ala Lys Gln Tyr Val Lys Val Gln Ile Pro
            180             185             190

Gly Leu Glu Asn Leu His Val Phe Val Pro Asp Ser Leu Ala Glu Glu
        195             200             205

Lys Lys Ile Ile Leu Gln Leu Leu Asn Ala Ala Thr Gly Lys Asp Cys
210             215             220

Ser Lys Asp Pro Asp Asp Val Phe Met Asp Ala Phe Leu Leu Leu Thr
225             230             235             240

Lys His Gly Asp Arg Ala Arg Asp Ser Glu Asp Gly Trp Gly Thr Trp
            245             250             255

Glu Ala Arg Ala Val Lys Ile Val Pro Gln Val Glu Thr Val Asp Thr
            260             265             270

Leu Arg Ser Met Gln Val Asp Asn Leu Leu Leu Val Val Met Glu Ser
        275             280             285

Ala His Leu Val Leu Gln Arg Lys Ala Phe Gln Gln Ser Ile Glu Gly
    290             295             300

Leu Met Thr Val Arg His Glu Gln Thr Ser Ser Gln Pro Ile Ile Ala
305             310             315             320

Lys Gly Leu Gln Gln Leu Lys Asn Asp Ala Leu Glu Leu Cys Asn Arg
            325             330             335

Ile Ser Asp Ala Ile Asp Arg Val Asp His Met Phe Thr Leu Glu Phe
            340             345             350

Asp Ala Glu Val Glu Glu Ser Glu Ser Ala Thr Leu Gln Gln Tyr Tyr
        355             360             365

Arg Glu Ala Met Ile Gln Gly Tyr Asn Phe Gly Phe Glu Tyr His Lys
    370             375             380

Glu Val Val Arg Leu Met Ser Gly Glu Phe Arg Gln Lys Ile Gly Asp
385             390             395             400

Lys Tyr Ile Thr Phe Ala Gln Lys Trp Met Asn Tyr Val Leu Thr Lys
            405             410             415

Cys Glu Ser Gly Arg Gly Thr Arg Pro Arg Trp Ala Thr Gln Gly Phe
            420             425             430

Asp Phe Leu Gln Ala Ile Glu Pro Ala Phe Ile Ser Ala Leu Pro Glu
        435             440             445

Asp Asp Phe Leu Ser Leu Gln Ala Leu Met Asn Glu Cys Ile Gly His
    450             455             460

Val Ile Gly Lys Pro His Ser Pro Val Thr Ala Ile His Arg Asn Ser
465             470             475             480

Pro Arg Pro Val Lys Val Pro Arg Cys His Ser Asp Pro Pro Asn Pro
            485             490             495

His Leu Ile Ile Pro Thr Pro Glu Gly Phe Arg Gly Ser Ser Val Pro
            500             505             510

Glu Asn Asp Arg Leu Ala Ser Ile Ala Ala Glu Leu Gln Phe Arg Ser
    515             520             525

Leu Ser Arg His Ser Ser Pro Thr Glu Glu Arg Asp Glu Pro Ala Tyr
530             535             540
```

| | | | | | | | | | | | | | | |
|---|---|---|---|---|---|---|---|---|---|---|---|---|---|---|
| Pro 545 | Arg | Ser | Asp | Ser | Ser 550 | Gly | Ser | Thr | Arg 555 | Arg | Ser | Trp | Glu | Leu | Arg 560 |
| Thr | Leu | Ile | Ser | Gln 565 | Thr | Lys | Asp | Ser | Ala 570 | Ser | Lys | Gln | Gly | Pro 575 | Ile |
| Glu | Ala | Ile | Gln 580 | Lys | Ser | Val | Arg | Leu 585 | Phe | Glu | Glu | Arg | Arg 590 | Tyr | Arg |
| Glu | Met | Arg 595 | Arg | Lys | Asn | Ile | Ile 600 | Gly | Gln | Val | Cys | Asp 605 | Thr | Pro | Lys |
| Ser | Tyr 610 | Asp | Asn | Val | Met | His 615 | Val | Gly | Leu | Arg | Lys 620 | Val | Thr | Phe | Lys |
| Trp 625 | Gln | Arg | Gly | Asn | Lys 630 | Ile | Gly | Glu | Gly | Gln 635 | Tyr | Gly | Lys | Val | Tyr 640 |
| Thr | Cys | Ile | Ser | Val 645 | Asp | Thr | Gly | Glu | Leu 650 | Met | Ala | Met | Lys | Glu 655 | Ile |
| Arg | Phe | Gln | Pro 660 | Asn | Asp | His | Lys | Thr 665 | Ile | Lys | Glu | Thr | Ala 670 | Asp | Glu |
| Leu | Lys | Ile 675 | Phe | Glu | Gly | Ile | Lys 680 | His | Pro | Asn | Leu | Val 685 | Arg | Tyr | Phe |
| Gly | Val 690 | Glu | Leu | His | Arg | Glu 695 | Glu | Met | Tyr | Ile | Phe 700 | Met | Glu | Tyr | Cys |
| Asp 705 | Glu | Gly | Thr | Leu | Glu 710 | Glu | Val | Ser | Arg | Leu 715 | Gly | Leu | Gln | Glu | His 720 |
| Val | Ile | Arg | Leu | Tyr 725 | Thr | Lys | Gln | Ile | Thr 730 | Val | Ala | Ile | Asn | Val 735 | Leu |
| His | Glu | His | Gly 740 | Ile | Val | His | Arg | Asp 745 | Ile | Lys | Gly | Ala | Asn 750 | Ile | Phe |
| Leu | Thr | Ser 755 | Ser | Gly | Leu | Ile | Lys 760 | Leu | Gly | Asp | Phe | Gly 765 | Cys | Ser | Val |
| Lys 770 | Leu | Lys | Asn | Asn | Ala 775 | Gln | Thr | Met | Pro | Gly 780 | Glu | Val | Asn | Ser | Thr |
| Leu 785 | Gly | Thr | Ala | Ala | Tyr 790 | Met | Ala | Pro | Glu | Val 795 | Ile | Thr | Arg | Ala | Lys 800 |
| Gly | Glu | Gly | His | Gly 805 | Arg | Ala | Ala | Asp | Ile 810 | Trp | Ser | Leu | Gly | Cys 815 | Val |
| Val | Ile | Glu | Met 820 | Val | Thr | Gly | Lys | Arg 825 | Pro | Trp | His | Glu 830 | Tyr | Glu | His |
| Asn | Phe | Gln 835 | Ile | Met | Tyr | Lys | Val 840 | Gly | Met | Gly | His | Lys 845 | Pro | Pro | Ile |
| Pro 850 | Glu | Arg | Leu | Ser | Pro 855 | Glu | Gly | Lys | Ala | Phe 860 | Leu | Ser | His | Cys | Leu |
| Glu 865 | Ser | Asp | Pro | Lys | Ile 870 | Arg | Trp | Thr | Ala | Ser 875 | Gln | Leu | Leu | Asp | His 880 |
| Ala | Phe | Val | Lys | Val 885 | Cys | Thr | Asp | Glu | Glu 890 | | | | | | |

( 2 ) INFORMATION FOR SEQ ID NO:9:

( i ) SEQUENCE CHARACTERISTICS:
        ( A ) LENGTH: 4592 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS (B) LOCATION: 355..4095

(xi) SEQUENCE DESCRIPTION: SEQ ID NO:9:

```
AAGAAGAAGG ACAGGGAGCA GAGGGGACAA GAAAACACGG CTGCTTTCTG GTTCAACCGA         60

TCGAACGAAC TGATCTGGTT AGAACTGCAG GCCTGGCACG CGGGCCGCAC CATCAATGAC        120

CAGGACCTCT TTCTCTACAC AGCCCGCCAG GCCATCCCAG ACATCATCAA TGAGATCCTC        180

ACCTTCAAAG TTAACTACGG GAGCATTGCC TTCTCCAGCA ATGGAGCCGG TTTCAACGGG        240

CCCTTGGTAG AAGGCCAGTG CAGAACCCCT CAGGAGACAA ACCGTGTGGG CTGCTCATCG        300

TACCACGAGC ACCTCCAGCG CCAGAGGGTC TCGTTTGAGC AGGTGAAGCG GATA ATG         357
                                                            Met
                                                             1
```

| GAG CTG CTG GAG TAC ATG GAG GCA CTT TAC CCA TCC TTG CAG GCT CTG | 405 |
|---|---|
| Glu Leu Leu Glu Tyr Met Glu Ala Leu Tyr Pro Ser Leu Gln Ala Leu | |
| 5 10 15 | |

| CAG AAG GAC TAT GAA CGG TAC GCC GCC AAG GAC TTT GAG GAC AGA GTG | 453 |
|---|---|
| Gln Lys Asp Tyr Glu Arg Tyr Ala Ala Lys Asp Phe Glu Asp Arg Val | |
| 20 25 30 | |

| CAG GCG CTC TGC CTG TGG CTC AAC ATC ACG AAA GAT CTA AAT CAG AAG | 501 |
|---|---|
| Gln Ala Leu Cys Leu Trp Leu Asn Ile Thr Lys Asp Leu Asn Gln Lys | |
| 35 40 45 | |

| CTG CGG ATC ATG GGC ACC GTG CTG GGC ATC AAG TTC CTA TCA GAC ATT | 549 |
|---|---|
| Leu Arg Ile Met Gly Thr Val Leu Gly Ile Lys Phe Leu Ser Asp Ile | |
| 50 55 60 65 | |

| GGC TGG CCA GTG AAA GAA ATC CCC TCC CCT CGG CCG TCC AAG GGC TAC | 597 |
|---|---|
| Gly Trp Pro Val Lys Glu Ile Pro Ser Pro Arg Pro Ser Lys Gly Tyr | |
| 70 75 80 | |

| GAG CCA GAG GAC GAG GTC GAG GAC ACG GAG GTT GAG CTG AGG GAG CTG | 645 |
|---|---|
| Glu Pro Glu Asp Glu Val Glu Asp Thr Glu Val Glu Leu Arg Glu Leu | |
| 85 90 95 | |

| GAG AGC GGG ACG GAG GAG AGT GAC GAG GAG CCA ACC CCC AGT CCG AGG | 693 |
|---|---|
| Glu Ser Gly Thr Glu Glu Ser Asp Glu Glu Pro Thr Pro Ser Pro Arg | |
| 100 105 110 | |

| GTG CCA GAG CTC AGG CTG TCC ACA GAC ACC ATC TTG GAC AGT CGC TCC | 741 |
|---|---|
| Val Pro Glu Leu Arg Leu Ser Thr Asp Thr Ile Leu Asp Ser Arg Ser | |
| 115 120 125 | |

| CAG GGC TGC GTC TCC AGG AAG CTG GAG AGG CTC GAG TCA GAG GAA GAT | 789 |
|---|---|
| Gln Gly Cys Val Ser Arg Lys Leu Glu Arg Leu Glu Ser Glu Glu Asp | |
| 130 135 140 145 | |

| TCC ATA GGC TGG GGG ACA GCG GAC TGT GGC CCT GAA GCC AGC AGG CAT | 837 |
|---|---|
| Ser Ile Gly Trp Gly Thr Ala Asp Cys Gly Pro Glu Ala Ser Arg His | |
| 150 155 160 | |

| TGT TTG ACT TCT ATG TAT AGA CCA TTC GTG GAC AAA GCA CTG AAG CAA | 885 |
|---|---|
| Cys Leu Thr Ser Met Tyr Arg Pro Phe Val Asp Lys Ala Leu Lys Gln | |
| 165 170 175 | |

| ATG GGG CTA AGA AAG TTA ATT TTA CGA CTT CAT AAG CTT ATG AAT GGG | 933 |
|---|---|
| Met Gly Leu Arg Lys Leu Ile Leu Arg Leu His Lys Leu Met Asn Gly | |
| 180 185 190 | |

| TCC TTG CAA AGA GCT CGT GTA GCT CTG GTG AAG GAC GAC CGT CCA GTG | 981 |
|---|---|
| Ser Leu Gln Arg Ala Arg Val Ala Leu Val Lys Asp Asp Arg Pro Val | |
| 195 200 205 | |

| GAG TTC TCT GAC TTT CCA GGT CCC ATG TGG GGC TCG GAT TAT GTG CAG | 1029 |
|---|---|
| Glu Phe Ser Asp Phe Pro Gly Pro Met Trp Gly Ser Asp Tyr Val Gln | |
| 210 215 220 225 | |

| TTG TCG GGA ACA CCT CCT TCC TCA GAG CAG AAG TGT AGC GCT GTG TCC | 1077 |
|---|---|
| Leu Ser Gly Thr Pro Pro Ser Ser Glu Gln Lys Cys Ser Ala Val Ser | |
| 230 235 240 | |

| TGG GAA GAA CTG AGA GCC ATG GAC CTG CCT TCC TTT GAG CCC GCC TTC | 1125 |
|---|---|
| Trp Glu Glu Leu Arg Ala Met Asp Leu Pro Ser Phe Glu Pro Ala Phe | |

```
                  245                         250                         255
CTG GTG CTC TGT CGG GTC CTG CTG AAC GTG ATC CAC GAG TGC CTG AAG                    1173
Leu Val Leu Cys Arg Val Leu Leu Asn Val Ile His Glu Cys Leu Lys
        260                         265                         270

CTG CGG CTG GAA CAG AGG CCT GCC GGG GAG CCT TCC CTC TTG AGT ATC                    1221
Leu Arg Leu Glu Gln Arg Pro Ala Gly Glu Pro Ser Leu Leu Ser Ile
275                         280                         285

AAA CAG CTA GTG CGA GAG TGT AAA GAG GTC CTA AAG GGC GGG CTC CTG                    1269
Lys Gln Leu Val Arg Glu Cys Lys Glu Val Leu Lys Gly Gly Leu Leu
290                         295                         300                 305

ATG AAG CAG TAT TAC CAG TTC ATG CTG CAG GAG GTC CTG GGC GGA CTG                    1317
Met Lys Gln Tyr Tyr Gln Phe Met Leu Gln Glu Val Leu Gly Gly Leu
                310                         315                         320

GAG AAG ACC GAC TGC AAC ATG GAT GCC TTT GAG GAG GAC CTG CAG AAG                    1365
Glu Lys Thr Asp Cys Asn Met Asp Ala Phe Glu Glu Asp Leu Gln Lys
            325                         330                         335

ATG CTG ATG GTG TAT TTT GAT TAC ATG AGA AGC TGG ATC CAA ATG CTA                    1413
Met Leu Met Val Tyr Phe Asp Tyr Met Arg Ser Trp Ile Gln Met Leu
            340                         345                         350

CAG CAG TTA CCT CAG GCT TCC CAT AGC TTA AAA AAC CTG CTA GAA GAG                    1461
Gln Gln Leu Pro Gln Ala Ser His Ser Leu Lys Asn Leu Leu Glu Glu
        355                         360                         365

GAA TGG AAT TTC ACC AAA GAA ATA ACC CAT TAT ATC CGT GGC GGA GAA                    1509
Glu Trp Asn Phe Thr Lys Glu Ile Thr His Tyr Ile Arg Gly Gly Glu
370                         375                         380                 385

GCG CAG GCT GGA AAG CTT TTC TGT GAC ATC GCA GGG ATG CTG CTG AAA                    1557
Ala Gln Ala Gly Lys Leu Phe Cys Asp Ile Ala Gly Met Leu Leu Lys
                390                         395                         400

TCC ACA GGG AGC TTT CTG GAA TCC GGC CTG CAG GAG AGC TGT GCT GAG                    1605
Ser Thr Gly Ser Phe Leu Glu Ser Gly Leu Gln Glu Ser Cys Ala Glu
            405                         410                         415

CTG TGG ACC AGC GCC GAC GAC AAC GGT GCT GCC GAC GAG CTA AGG AGA                    1653
Leu Trp Thr Ser Ala Asp Asp Asn Gly Ala Ala Asp Glu Leu Arg Arg
            420                         425                         430

TCT GTC ATC GAG ATC AGC CGA GCA CTC AAG GAG CTC TTC CAC GAA GCC                    1701
Ser Val Ile Glu Ile Ser Arg Ala Leu Lys Glu Leu Phe His Glu Ala
        435                         440                         445

AGG GAA AGA GCC TCC AAG GCC CTG GGC TTT GCT AAA ATG CTG AGG AAG                    1749
Arg Glu Arg Ala Ser Lys Ala Leu Gly Phe Ala Lys Met Leu Arg Lys
450                         455                         460                 465

GAC CTA GAA ATA GCA GCA GAG TTC GTG CTA TCT GCA TCA GCC CGA GAG                    1797
Asp Leu Glu Ile Ala Ala Glu Phe Val Leu Ser Ala Ser Ala Arg Glu
                470                         475                         480

CTC CTG GAC GCT CTG AAA GCA AAG CAG TAT GTT AAG GTA CAG ATT CCC                    1845
Leu Leu Asp Ala Leu Lys Ala Lys Gln Tyr Val Lys Val Gln Ile Pro
            485                         490                         495

GGG TTA GAG AAT TTG CAC GTG TTT GTC CCC GAC AGC CTC GCT GAG GAG                    1893
Gly Leu Glu Asn Leu His Val Phe Val Pro Asp Ser Leu Ala Glu Glu
            500                         505                         510

AAG AAA ATT ATT TTG CAG CTA CTC AAT GCT GCC ACA GGA AAG GAC TGC                    1941
Lys Lys Ile Ile Leu Gln Leu Leu Asn Ala Ala Thr Gly Lys Asp Cys
        515                         520                         525

TCA AAG GAT CCA GAC GAC GTC TTC ATG GAT GCC TTC CTG CTC CTG ACC                    1989
Ser Lys Asp Pro Asp Asp Val Phe Met Asp Ala Phe Leu Leu Leu Thr
530                         535                         540                 545

AAG CAT GGG GAC CGA GCC CGT GAC TCA GAA GAT GGC TGG GGC ACA TGG                    2037
Lys His Gly Asp Arg Ala Arg Asp Ser Glu Asp Gly Trp Gly Thr Trp
                550                         555                         560

GAA GCT CGG GCT GTC AAA ATT GTG CCT CAG GTG GAG ACT GTG GAC ACC                    2085
Glu Ala Arg Ala Val Lys Ile Val Pro Gln Val Glu Thr Val Asp Thr
```

|  |  |  |  |  |  |  |  |  |  |  |  |  |  |  |  |
|---|---|---|---|---|---|---|---|---|---|---|---|---|---|---|---|
| | | | | 565 | | | | | 570 | | | | | 575 | |
| CTG | AGA | AGC | ATG | CAG | GTG | GAC | AAC | CTT | CTG | CTG | GTT | GTC | ATG | GAG | TCT | 2133
| Leu | Arg | Ser | Met | Gln | Val | Asp | Asn | Leu | Leu | Leu | Val | Val | Met | Glu | Ser |
| | | 580 | | | | | 585 | | | | | 590 | | | |
| GCT | CAC | CTC | GTA | CTT | CAG | AGA | AAA | GCC | TTC | CAG | CAG | TCC | ATT | GAG | GGG | 2181
| Ala | His | Leu | Val | Leu | Gln | Arg | Lys | Ala | Phe | Gln | Gln | Ser | Ile | Glu | Gly |
| | 595 | | | | | 600 | | | | | 605 | | | | |
| CTG | ATG | ACT | GTA | CGC | CAT | GAG | CAG | ACA | TCT | AGC | CAG | CCC | ATC | ATC | GCC | 2229
| Leu | Met | Thr | Val | Arg | His | Glu | Gln | Thr | Ser | Ser | Gln | Pro | Ile | Ile | Ala |
| 610 | | | | | 615 | | | | | 620 | | | | | 625 |
| AAA | GGT | TTG | CAG | CAG | CTC | AAG | AAC | GAT | GCA | CTT | GAG | CTA | TGC | AAC | AGA | 2277
| Lys | Gly | Leu | Gln | Gln | Leu | Lys | Asn | Asp | Ala | Leu | Glu | Leu | Cys | Asn | Arg |
| | | | | 630 | | | | | 635 | | | | | 640 | |
| ATC | AGC | GAT | GCC | ATC | GAC | CGT | GTG | GAC | CAC | ATG | TTC | ACC | CTG | GAG | TTC | 2325
| Ile | Ser | Asp | Ala | Ile | Asp | Arg | Val | Asp | His | Met | Phe | Thr | Leu | Glu | Phe |
| | | | 645 | | | | | 650 | | | | | 655 | | |
| GAT | GCT | GAG | GTC | GAG | GAG | TCT | GAG | TCG | GCC | ACG | CTG | CAG | CAG | TAC | TAC | 2373
| Asp | Ala | Glu | Val | Glu | Glu | Ser | Glu | Ser | Ala | Thr | Leu | Gln | Gln | Tyr | Tyr |
| | | 660 | | | | | 665 | | | | | 670 | | | |
| CGA | GAA | GCC | ATG | ATT | CAG | GGC | TAC | AAC | TTT | GGG | TTT | GAG | TAT | CAT | AAA | 2421
| Arg | Glu | Ala | Met | Ile | Gln | Gly | Tyr | Asn | Phe | Gly | Phe | Glu | Tyr | His | Lys |
| | 675 | | | | | 680 | | | | | 685 | | | | |
| GAA | GTT | GTT | CGT | TTG | ATG | TCT | GGG | GAA | TTC | AGG | CAG | AAG | ATA | GGA | GAC | 2469
| Glu | Val | Val | Arg | Leu | Met | Ser | Gly | Glu | Phe | Arg | Gln | Lys | Ile | Gly | Asp |
| 690 | | | | | 695 | | | | | 700 | | | | | 705 |
| AAA | TAT | ATA | AGC | TTC | GCC | CAG | AAG | TGG | ATG | AAT | TAC | GTG | CTG | ACC | AAA | 2517
| Lys | Tyr | Ile | Ser | Phe | Ala | Gln | Lys | Trp | Met | Asn | Tyr | Val | Leu | Thr | Lys |
| | | | | 710 | | | | | 715 | | | | | 720 | |
| TGC | GAG | AGC | GGC | AGA | GGC | ACA | AGA | CCC | AGA | TGG | GCC | ACC | CAA | GGA | TTT | 2565
| Cys | Glu | Ser | Gly | Arg | Gly | Thr | Arg | Pro | Arg | Trp | Ala | Thr | Gln | Gly | Phe |
| | | 725 | | | | | 730 | | | | | 735 | | | |
| GAT | TTC | CTA | CAA | GCC | ATT | GAA | CCT | GCC | TTT | ATT | TCA | GCT | TTA | CCA | GAA | 2613
| Asp | Phe | Leu | Gln | Ala | Ile | Glu | Pro | Ala | Phe | Ile | Ser | Ala | Leu | Pro | Glu |
| | | 740 | | | | | 745 | | | | | 750 | | | |
| GAT | GAC | TTC | TTG | AGT | TTG | CAA | GCC | CTG | ATG | AAT | GAG | TGC | ATC | GGG | CAC | 2661
| Asp | Asp | Phe | Leu | Ser | Leu | Gln | Ala | Leu | Met | Asn | Glu | Cys | Ile | Gly | His |
| 755 | | | | | 760 | | | | | 765 | | | | | |
| GTC | ATA | GGA | AAG | CCA | CAC | AGC | CCT | GTC | ACA | GCT | ATC | CAT | CGG | AAC | AGC | 2709
| Val | Ile | Gly | Lys | Pro | His | Ser | Pro | Val | Thr | Ala | Ile | His | Arg | Asn | Ser |
| 770 | | | | | 775 | | | | | 780 | | | | | 785 |
| CCC | CGC | CCT | GTG | AAG | GTG | CCC | CGA | TGC | CAC | AGT | GAC | CCT | CCT | AAC | CCT | 2757
| Pro | Arg | Pro | Val | Lys | Val | Pro | Arg | Cys | His | Ser | Asp | Pro | Pro | Asn | Pro |
| | | | | 790 | | | | | 795 | | | | | 800 | |
| CAC | CTC | ATC | ATC | CCG | ACT | CCA | GAG | GGA | TTC | AGC | ACC | CGG | AGC | GTG | CCT | 2805
| His | Leu | Ile | Ile | Pro | Thr | Pro | Glu | Gly | Phe | Ser | Thr | Arg | Ser | Val | Pro |
| | | | 805 | | | | | 810 | | | | | 815 | | |
| TCC | GAC | GCT | CGG | ACC | CAT | GGC | AAC | TCT | GTT | GCT | GCT | GCT | GCT | GCT | GTT | 2853
| Ser | Asp | Ala | Arg | Thr | His | Gly | Asn | Ser | Val | Ala | Ala | Ala | Ala | Ala | Val |
| | | 820 | | | | | 825 | | | | | 830 | | | |
| CGT | GCC | GCC | GCC | ACC | ACT | GCT | GCT | GGC | CGC | CCT | GGC | CCA | GGT | GGT | GGT | 2901
| Arg | Ala | Ala | Ala | Thr | Thr | Ala | Ala | Gly | Arg | Pro | Gly | Pro | Gly | Gly | Gly |
| | 835 | | | | | 840 | | | | | 845 | | | | |
| GAC | TCT | GTG | CCA | GCC | AAA | CCT | GTC | AAC | ACT | GCC | CCT | GAT | ACC | AGG | GGT | 2949
| Asp | Ser | Val | Pro | Ala | Lys | Pro | Val | Asn | Thr | Ala | Pro | Asp | Thr | Arg | Gly |
| 850 | | | | | 855 | | | | | 860 | | | | | 865 |
| TCC | AGT | GTC | CCT | GAA | AAC | GAC | CGC | TTG | GCC | TCC | ATA | GCT | GCA | GAA | CTG | 2997
| Ser | Ser | Val | Pro | Glu | Asn | Asp | Arg | Leu | Ala | Ser | Ile | Ala | Ala | Glu | Leu |
| | | | | 870 | | | | | 875 | | | | | 880 | |
| CAG | TTC | AGG | TCT | CTG | AGT | CGG | CAC | TCA | AGC | CCC | ACG | GAA | GAG | CGA | GAC | 3045
| Gln | Phe | Arg | Ser | Leu | Ser | Arg | His | Ser | Ser | Pro | Thr | Glu | Glu | Arg | Asp |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     | 885 |     |     |     |     | 890 |     |     |     |     | 895 |     |     |      |
| GAG | CCA | GCG | TAT | CCT | CGG | AGT | GAC | TCA | AGT | GGA | TCA | ACT | CGG | AGA | AGC | 3093 |
| Glu | Pro | Ala | Tyr | Pro | Arg | Ser | Asp | Ser | Ser | Gly | Ser | Thr | Arg | Arg | Ser |      |
|     |     | 900 |     |     |     |     |     | 905 |     |     |     |     | 910 |     |     |      |
| TGG | GAA | CTT | CGA | ACA | CTC | ATC | AGC | CAG | ACC | AAA | GAC | TCG | GCC | TCT | AAG | 3141 |
| Trp | Glu | Leu | Arg | Thr | Leu | Ile | Ser | Gln | Thr | Lys | Asp | Ser | Ala | Ser | Lys |      |
|     | 915 |     |     |     |     |     | 920 |     |     |     |     | 925 |     |     |     |      |
| CAG | GGG | CCC | ATA | GAA | GCT | ATC | CAG | AAG | TCA | GTC | CGA | CTG | TTT | GAA | GAG | 3189 |
| Gln | Gly | Pro | Ile | Glu | Ala | Ile | Gln | Lys | Ser | Val | Arg | Leu | Phe | Glu | Glu |      |
| 930 |     |     |     |     | 935 |     |     |     |     | 940 |     |     |     |     | 945 |      |
| AGG | AGG | TAT | CGA | GAG | ATG | AGG | AGA | AAG | AAT | ATC | ATC | GGC | CAA | GTG | TGC | 3237 |
| Arg | Arg | Tyr | Arg | Glu | Met | Arg | Arg | Lys | Asn | Ile | Ile | Gly | Gln | Val | Cys |      |
|     |     |     |     |     | 950 |     |     |     |     | 955 |     |     |     |     | 960 |      |
| GAT | ACC | CCT | AAG | TCC | TAT | GAT | AAC | GTC | ATG | CAT | GTT | GGA | CTG | AGG | AAG | 3285 |
| Asp | Thr | Pro | Lys | Ser | Tyr | Asp | Asn | Val | Met | His | Val | Gly | Leu | Arg | Lys |      |
|     |     | 965 |     |     |     |     | 970 |     |     |     |     | 975 |     |     |     |      |
| GTG | ACA | TTT | AAG | TGG | CAA | AGA | GGA | AAC | AAA | ATT | GGA | GAA | GGA | CAG | TAT | 3333 |
| Val | Thr | Phe | Lys | Trp | Gln | Arg | Gly | Asn | Lys | Ile | Gly | Glu | Gly | Gln | Tyr |      |
|     | 980 |     |     |     |     |     | 985 |     |     |     |     | 990 |     |     |     |      |
| GGA | AAA | GTA | TAC | ACC | TGC | ATC | AGT | GTT | GAC | ACA | GGG | GAG | CTG | ATG | GCC | 3381 |
| Gly | Lys | Val | Tyr | Thr | Cys | Ile | Ser | Val | Asp | Thr | Gly | Glu | Leu | Met | Ala |      |
| 995 |     |     |     |     | 1000|     |     |     |     | 1005|     |     |     |     |     |      |
| ATG | AAG | GAG | ATT | CGA | TTT | CAG | CCT | AAC | GAC | CAC | AAG | ACT | ATC | AAG | GAG | 3429 |
| Met | Lys | Glu | Ile | Arg | Phe | Gln | Pro | Asn | Asp | His | Lys | Thr | Ile | Lys | Glu |      |
| 1010|     |     |     |     | 1015|     |     |     |     | 1020|     |     |     |     | 1025|      |
| ACT | GCA | GAC | GAG | TTG | AAA | ATA | TTT | GAA | GGC | ATC | AAG | CAC | CCC | AAC | CTG | 3477 |
| Thr | Ala | Asp | Glu | Leu | Lys | Ile | Phe | Glu | Gly | Ile | Lys | His | Pro | Asn | Leu |      |
|     |     |     |     | 1030|     |     |     |     | 1035|     |     |     |     | 1040|     |      |
| GTC | CGG | TAT | TTT | GGC | GTG | GAG | CTT | CAC | AGG | GAA | GAG | ATG | TAC | ATC | TTC | 3525 |
| Val | Arg | Tyr | Phe | Gly | Val | Glu | Leu | His | Arg | Glu | Glu | Met | Tyr | Ile | Phe |      |
|     |     |     | 1045|     |     |     |     | 1050|     |     |     |     | 1055|     |     |      |
| ATG | GAG | TAC | TGT | GAT | GAG | GGT | ACA | CTA | GAG | GAG | GTG | TCA | CGA | CTG | GGC | 3573 |
| Met | Glu | Tyr | Cys | Asp | Glu | Gly | Thr | Leu | Glu | Glu | Val | Ser | Arg | Leu | Gly |      |
|     |     | 1060|     |     |     |     | 1065|     |     |     |     | 1070|     |     |     |      |
| CTG | CAG | GAG | CAC | GTC | ATC | AGG | TTA | TAT | ACC | AAG | CAG | ATC | ACT | GTC | GCC | 3621 |
| Leu | Gln | Glu | His | Val | Ile | Arg | Leu | Tyr | Thr | Lys | Gln | Ile | Thr | Val | Ala |      |
|     | 1075|     |     |     |     | 1080|     |     |     |     | 1085|     |     |     |     |      |
| ATC | AAC | GTC | CTC | CAT | GAG | CAC | GGC | ATC | GTT | CAC | CGA | GAC | ATC | AAA | GGT | 3669 |
| Ile | Asn | Val | Leu | His | Glu | His | Gly | Ile | Val | His | Arg | Asp | Ile | Lys | Gly |      |
| 1090|     |     |     |     | 1095|     |     |     |     | 1100|     |     |     |     | 1105|      |
| GCC | AAT | ATC | TTC | CTT | ACG | TCA | TCT | GGA | CTA | ATC | AAG | CTG | GGA | GAT | TTT | 3717 |
| Ala | Asn | Ile | Phe | Leu | Thr | Ser | Ser | Gly | Leu | Ile | Lys | Leu | Gly | Asp | Phe |      |
|     |     |     |     | 1110|     |     |     |     | 1115|     |     |     |     | 1120|     |      |
| GGA | TGC | TCT | GTA | AAA | CTT | AAA | AAC | AAC | GCC | CAG | ACC | ATG | CCC | GGA | GAG | 3765 |
| Gly | Cys | Ser | Val | Lys | Leu | Lys | Asn | Asn | Ala | Gln | Thr | Met | Pro | Gly | Glu |      |
|     |     |     | 1125|     |     |     |     | 1130|     |     |     |     | 1135|     |     |      |
| GTG | AAC | AGC | ACC | CTA | GGG | ACA | GCA | GCT | TAC | ATG | GCC | CCT | GAA | GTT | ATT | 3813 |
| Val | Asn | Ser | Thr | Leu | Gly | Thr | Ala | Ala | Tyr | Met | Ala | Pro | Glu | Val | Ile |      |
|     |     | 1140|     |     |     |     | 1145|     |     |     |     | 1150|     |     |     |      |
| ACC | CGA | GCC | AAA | GGA | GAA | GGC | CAC | GGA | CGT | GCG | GCA | GAT | ATC | TGG | AGT | 3861 |
| Thr | Arg | Ala | Lys | Gly | Glu | Gly | His | Gly | Arg | Ala | Ala | Asp | Ile | Trp | Ser |      |
|     | 1155|     |     |     |     | 1160|     |     |     |     | 1165|     |     |     |     |      |
| CTG | GGG | TGC | GTC | GTC | ATA | GAG | ATG | GTG | ACT | GGC | AAG | CGG | CCT | TGG | CAT | 3909 |
| Leu | Gly | Cys | Val | Val | Ile | Glu | Met | Val | Thr | Gly | Lys | Arg | Pro | Trp | His |      |
| 1170|     |     |     |     | 1175|     |     |     |     | 1180|     |     |     |     | 1185|      |
| GAG | TAT | GAA | CAC | AAC | TTT | CAG | ATT | ATG | TAC | AAG | GTG | GGG | ATG | GGA | CAC | 3957 |
| Glu | Tyr | Glu | His | Asn | Phe | Gln | Ile | Met | Tyr | Lys | Val | Gly | Met | Gly | His |      |
|     |     |     |     | 1190|     |     |     |     | 1195|     |     |     |     | 1200|     |      |
| AAG | CCA | CCA | ATC | CCG | GAA | AGG | CTA | AGC | CCT | GAA | GGA | AAG | GCC | TTT | CTC | 4005 |
| Lys | Pro | Pro | Ile | Pro | Glu | Arg | Leu | Ser | Pro | Glu | Gly | Lys | Ala | Phe | Leu |      |

|  |  |  |  |  |  |  |  |  |  |  |  |  |  |  |
|---|---|---|---|---|---|---|---|---|---|---|---|---|---|---|
| TCG | CAC | TGC | CTG | GAA | AGT | GAC | CCG | AAG | ATA | CGG | TGG | ACA | GCC | AGC | CAG |
| Ser | His | Cys | Leu | Glu | Ser | Asp | Pro | Lys | Ile | Arg | Trp | Thr | Ala | Ser | Gln |
|  | 1220 |  |  |  | 1225 |  |  |  | 1230 |  |

4053

|  |  |  |  |  |  |  |  |  |  |  |  |  |
|---|---|---|---|---|---|---|---|---|---|---|---|---|
| CTC | CTC | GAC | CAC | GCT | TTT | GTC | AAG | GTT | TGC | ACA | GAT | GAA | GAG |
| Leu | Leu | Asp | His | Ala | Phe | Val | Lys | Val | Cys | Thr | Asp | Glu | Glu |
|  | 1235 |  |  |  | 1240 |  |  |  | 1245 |

4095

```
TGAAGTGAAC CAGTCCGTGG CCTAGTAGTG TGTGGACAGA ATCCCGTGAT CACTACTGTA    4155
TGTAATATTT ACATAAAGAC TGCAGCGCAG GCGGCCTTCC TAACCTCCCA GGACTGAAGA    4215
CTACAGGGGT GACAAGCCTC ACTTCTGCTG CTCCTGTCGC CTGCTGAGTG ACAGTGCTGA    4275
GGTTAAAGGA GCCGCACGTT AAGTGCCATT ACTACTGTAC ACGGCCACCG CCTCTGTCCC    4335
CTCCGACCCT CTCGTGACTG AGAACCAACC GTGTCATCAG CACAGTGTTT TTGAGCTCCT    4395
GGGGTTCAGA AGAACATGTA GTGTTCCCGG GTGTCCGGGA CGTTTATTTC AACCTCCTGG    4455
TCGTTGGCTC TGACTGTGGA GCCTCCTTGT TCGAAAGCTG CAGGTTTGTT ATGCAAAGGC    4515
TCGTAAGTGA AGCTGAAGAA AAGGTTCTTT TTCAATAAAT GGTTTATTTT AGGAAAGCGA    4575
AAAAAAAAAA AAAAAA                                                   4592
```

( 2 ) INFORMATION FOR SEQ ID NO:10:

( i ) SEQUENCE CHARACTERISTICS:
        ( A ) LENGTH: 1247 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

| Met | Glu | Leu | Leu | Glu | Tyr | Met | Glu | Ala | Leu | Tyr | Pro | Ser | Leu | Gln | Ala |
|---|---|---|---|---|---|---|---|---|---|---|---|---|---|---|---|
| 1 |  |  |  | 5 |  |  |  |  | 10 |  |  |  |  | 15 |  |
| Leu | Gln | Lys | Asp | Tyr | Glu | Arg | Tyr | Ala | Ala | Lys | Asp | Phe | Glu | Asp | Arg |
|  |  |  | 20 |  |  |  |  | 25 |  |  |  |  | 30 |  |  |
| Val | Gln | Ala | Leu | Cys | Leu | Trp | Leu | Asn | Ile | Thr | Lys | Asp | Leu | Asn | Gln |
|  |  | 35 |  |  |  |  | 40 |  |  |  |  | 45 |  |  |  |
| Lys | Leu | Arg | Ile | Met | Gly | Thr | Val | Leu | Gly | Ile | Lys | Phe | Leu | Ser | Asp |
|  | 50 |  |  |  |  | 55 |  |  |  |  | 60 |  |  |  |  |
| Ile | Gly | Trp | Pro | Val | Lys | Glu | Ile | Pro | Ser | Pro | Arg | Pro | Ser | Lys | Gly |
| 65 |  |  |  |  | 70 |  |  |  |  | 75 |  |  |  |  | 80 |
| Tyr | Glu | Pro | Glu | Asp | Glu | Val | Glu | Asp | Thr | Glu | Val | Glu | Leu | Arg | Glu |
|  |  |  |  | 85 |  |  |  |  | 90 |  |  |  |  | 95 |  |
| Leu | Glu | Ser | Gly | Thr | Glu | Glu | Ser | Asp | Glu | Glu | Pro | Thr | Pro | Ser | Pro |
|  |  |  | 100 |  |  |  |  | 105 |  |  |  |  | 110 |  |  |
| Arg | Val | Pro | Glu | Leu | Arg | Leu | Ser | Thr | Asp | Thr | Ile | Leu | Asp | Ser | Arg |
|  |  | 115 |  |  |  |  | 120 |  |  |  |  | 125 |  |  |  |
| Ser | Gln | Gly | Cys | Val | Ser | Arg | Lys | Leu | Glu | Arg | Leu | Glu | Ser | Glu | Glu |
|  | 130 |  |  |  |  | 135 |  |  |  |  | 140 |  |  |  |  |
| Asp | Ser | Ile | Gly | Trp | Gly | Thr | Ala | Asp | Cys | Gly | Pro | Glu | Ala | Ser | Arg |
| 145 |  |  |  |  | 150 |  |  |  |  | 155 |  |  |  |  | 160 |
| His | Cys | Leu | Thr | Ser | Met | Tyr | Arg | Pro | Phe | Val | Asp | Lys | Ala | Leu | Lys |
|  |  |  |  | 165 |  |  |  |  | 170 |  |  |  |  | 175 |  |
| Gln | Met | Gly | Leu | Arg | Lys | Leu | Ile | Leu | Arg | Leu | His | Lys | Leu | Met | Asn |
|  |  |  | 180 |  |  |  |  | 185 |  |  |  |  | 190 |  |  |
| Gly | Ser | Leu | Gln | Arg | Ala | Arg | Val | Ala | Leu | Val | Lys | Asp | Asp | Arg | Pro |
|  |  | 195 |  |  |  |  | 200 |  |  |  |  | 205 |  |  |  |
| Val | Glu | Phe | Ser | Asp | Phe | Pro | Gly | Pro | Met | Trp | Gly | Ser | Asp | Tyr | Val |

-continued

|     |     |     |     |     | 210 |     |     |     | 215 |     |     |     | 220 |     |
|-----|-----|-----|-----|-----|-----|-----|-----|-----|-----|-----|-----|-----|-----|-----|
| Gln | Leu | Ser | Gly | Thr | Pro | Pro | Ser | Ser | Glu | Gln | Lys | Cys | Ser | Ala | Val |
| 225 |     |     |     |     | 230 |     |     |     | 235 |     |     |     |     | 240 |
| Ser | Trp | Glu | Glu | Leu | Arg | Ala | Met | Asp | Leu | Pro | Ser | Phe | Glu | Pro | Ala |
|     |     |     |     | 245 |     |     |     | 250 |     |     |     | 255 |     |     |
| Phe | Leu | Val | Leu | Cys | Arg | Val | Leu | Leu | Asn | Val | Ile | His | Glu | Cys | Leu |
|     |     |     | 260 |     |     |     | 265 |     |     |     |     | 270 |     |     |
| Lys | Leu | Arg | Leu | Glu | Gln | Arg | Pro | Ala | Gly | Glu | Pro | Ser | Leu | Leu | Ser |
|     |     | 275 |     |     |     | 280 |     |     |     |     | 285 |     |     |     |
| Ile | Lys | Gln | Leu | Val | Arg | Glu | Cys | Lys | Glu | Val | Leu | Lys | Gly | Gly | Leu |
|     | 290 |     |     |     | 295 |     |     |     | 300 |     |     |     |     |     |
| Leu | Met | Lys | Gln | Tyr | Tyr | Gln | Phe | Met | Leu | Gln | Val | Leu | Gly | Gly |
| 305 |     |     |     | 310 |     |     |     | 315 |     |     |     |     | 320 |
| Leu | Glu | Lys | Thr | Asp | Cys | Asn | Met | Asp | Ala | Phe | Glu | Glu | Asp | Leu | Gln |
|     |     |     | 325 |     |     |     | 330 |     |     |     |     | 335 |     |
| Lys | Met | Leu | Met | Val | Tyr | Phe | Asp | Tyr | Met | Arg | Ser | Trp | Ile | Gln | Met |
|     |     |     | 340 |     |     |     | 345 |     |     |     |     | 350 |     |
| Leu | Gln | Gln | Leu | Pro | Gln | Ala | Ser | His | Ser | Leu | Lys | Asn | Leu | Leu | Glu |
|     |     | 355 |     |     |     | 360 |     |     |     | 365 |     |     |     |
| Glu | Glu | Trp | Asn | Phe | Thr | Lys | Glu | Ile | Thr | His | Tyr | Ile | Arg | Gly | Gly |
|     | 370 |     |     |     | 375 |     |     |     | 380 |     |     |     |     |
| Glu | Ala | Gln | Ala | Gly | Lys | Leu | Phe | Cys | Asp | Ile | Ala | Gly | Met | Leu | Leu |
| 385 |     |     |     | 390 |     |     |     | 395 |     |     |     |     | 400 |
| Lys | Ser | Thr | Gly | Ser | Phe | Leu | Glu | Ser | Gly | Leu | Gln | Glu | Ser | Cys | Ala |
|     |     |     | 405 |     |     |     | 410 |     |     |     |     | 415 |
| Glu | Leu | Trp | Thr | Ser | Ala | Asp | Asp | Asn | Gly | Ala | Ala | Asp | Glu | Leu | Arg |
|     |     | 420 |     |     |     | 425 |     |     |     | 430 |     |     |
| Arg | Ser | Val | Ile | Glu | Ile | Ser | Arg | Ala | Leu | Lys | Glu | Leu | Phe | His | Glu |
|     | 435 |     |     |     | 440 |     |     |     | 445 |     |     |     |
| Ala | Arg | Glu | Arg | Ala | Ser | Lys | Ala | Leu | Gly | Phe | Ala | Lys | Met | Leu | Arg |
| 450 |     |     |     | 455 |     |     |     | 460 |     |     |     |     |
| Lys | Asp | Leu | Glu | Ile | Ala | Ala | Glu | Phe | Val | Leu | Ser | Ala | Ser | Ala | Arg |
| 465 |     |     |     | 470 |     |     |     | 475 |     |     |     | 480 |
| Glu | Leu | Leu | Asp | Ala | Leu | Lys | Ala | Lys | Gln | Tyr | Val | Lys | Val | Gln | Ile |
|     |     |     | 485 |     |     |     | 490 |     |     |     | 495 |
| Pro | Gly | Leu | Glu | Asn | Leu | His | Val | Phe | Val | Pro | Asp | Ser | Leu | Ala | Glu |
|     |     |     | 500 |     |     |     | 505 |     |     |     | 510 |
| Glu | Lys | Lys | Ile | Ile | Leu | Gln | Leu | Leu | Asn | Ala | Ala | Thr | Gly | Lys | Asp |
|     | 515 |     |     |     | 520 |     |     |     | 525 |     |     |     |
| Cys | Ser | Lys | Asp | Pro | Asp | Asp | Val | Phe | Met | Asp | Ala | Phe | Leu | Leu | Leu |
| 530 |     |     |     | 535 |     |     |     | 540 |     |     |     |
| Thr | Lys | His | Gly | Asp | Arg | Ala | Arg | Asp | Ser | Glu | Asp | Gly | Trp | Gly | Thr |
| 545 |     |     |     | 550 |     |     |     | 555 |     |     |     | 560 |
| Trp | Glu | Ala | Arg | Ala | Val | Lys | Ile | Val | Pro | Gln | Val | Glu | Thr | Val | Asp |
|     |     |     | 565 |     |     |     | 570 |     |     |     | 575 |
| Thr | Leu | Arg | Ser | Met | Gln | Val | Asp | Asn | Leu | Leu | Leu | Val | Val | Met | Glu |
|     |     |     | 580 |     |     |     | 585 |     |     |     | 590 |
| Ser | Ala | His | Leu | Val | Leu | Gln | Arg | Lys | Ala | Phe | Gln | Gln | Ser | Ile | Glu |
|     |     | 595 |     |     |     | 600 |     |     |     | 605 |     |     |
| Gly | Leu | Met | Thr | Val | Arg | His | Glu | Gln | Thr | Ser | Ser | Gln | Pro | Ile | Ile |
|     | 610 |     |     |     | 615 |     |     |     | 620 |     |     |     |
| Ala | Lys | Gly | Leu | Gln | Gln | Leu | Lys | Asn | Asp | Ala | Leu | Glu | Leu | Cys | Asn |
| 625 |     |     |     | 630 |     |     |     | 635 |     |     |     | 640 |

```
Arg  Ile  Ser  Asp  Ala  Ile  Asp  Arg  Val  Asp  His  Met  Phe  Thr  Leu  Glu
              645                 650                      655

Phe  Asp  Ala  Glu  Val  Glu  Glu  Ser  Glu  Ser  Ala  Thr  Leu  Gln  Gln  Tyr
              660                 665                      670

Tyr  Arg  Glu  Ala  Met  Ile  Gln  Gly  Tyr  Asn  Phe  Gly  Phe  Glu  Tyr  His
         675                 680                      685

Lys  Glu  Val  Val  Arg  Leu  Met  Ser  Gly  Glu  Phe  Arg  Gln  Lys  Ile  Gly
    690                      695                 700

Asp  Lys  Tyr  Ile  Ser  Phe  Ala  Gln  Lys  Trp  Met  Asn  Tyr  Val  Leu  Thr
705                      710                 715                          720

Lys  Cys  Glu  Ser  Gly  Arg  Gly  Thr  Arg  Pro  Arg  Trp  Ala  Thr  Gln  Gly
              725                 730                      735

Phe  Asp  Phe  Leu  Gln  Ala  Ile  Glu  Pro  Ala  Phe  Ile  Ser  Ala  Leu  Pro
              740                 745                      750

Glu  Asp  Asp  Phe  Leu  Ser  Leu  Gln  Ala  Leu  Met  Asn  Glu  Cys  Ile  Gly
         755                 760                      765

His  Val  Ile  Gly  Lys  Pro  His  Ser  Pro  Val  Thr  Ala  Ile  His  Arg  Asn
    770                      775                 780

Ser  Pro  Arg  Pro  Val  Lys  Val  Pro  Arg  Cys  His  Ser  Asp  Pro  Pro  Asn
785                      790                 795                          800

Pro  His  Leu  Ile  Ile  Pro  Thr  Pro  Glu  Gly  Phe  Ser  Thr  Arg  Ser  Val
              805                 810                      815

Pro  Ser  Asp  Ala  Arg  Thr  His  Gly  Asn  Ser  Val  Ala  Ala  Ala  Ala  Ala
              820                 825                      830

Val  Arg  Ala  Ala  Ala  Thr  Thr  Ala  Ala  Gly  Arg  Pro  Gly  Pro  Gly  Gly
              835                 840                      845

Gly  Asp  Ser  Val  Pro  Ala  Lys  Pro  Val  Asn  Thr  Ala  Pro  Asp  Thr  Arg
850                      855                 860

Gly  Ser  Ser  Val  Pro  Glu  Asn  Asp  Arg  Leu  Ala  Ser  Ile  Ala  Ala  Glu
865                      870                 875                          880

Leu  Gln  Phe  Arg  Ser  Leu  Ser  Arg  His  Ser  Ser  Pro  Thr  Glu  Glu  Arg
              885                 890                      895

Asp  Glu  Pro  Ala  Tyr  Pro  Arg  Ser  Asp  Ser  Ser  Gly  Ser  Thr  Arg  Arg
              900                 905                      910

Ser  Trp  Glu  Leu  Arg  Thr  Leu  Ile  Ser  Gln  Thr  Lys  Asp  Ser  Ala  Ser
         915                 920                      925

Lys  Gln  Gly  Pro  Ile  Glu  Ala  Ile  Gln  Lys  Ser  Val  Arg  Leu  Phe  Glu
    930                      935                 940

Glu  Arg  Arg  Tyr  Arg  Glu  Met  Arg  Arg  Lys  Asn  Ile  Ile  Gly  Gln  Val
945                      950                 955                          960

Cys  Asp  Thr  Pro  Lys  Ser  Tyr  Asp  Asn  Val  Met  His  Val  Gly  Leu  Arg
              965                 970                      975

Lys  Val  Thr  Phe  Lys  Trp  Gln  Arg  Gly  Asn  Lys  Ile  Gly  Glu  Gly  Gln
              980                 985                      990

Tyr  Gly  Lys  Val  Tyr  Thr  Cys  Ile  Ser  Val  Asp  Thr  Gly  Glu  Leu  Met
         995                 1000                     1005

Ala  Met  Lys  Glu  Ile  Arg  Phe  Gln  Pro  Asn  Asp  His  Lys  Thr  Ile  Lys
    1010                      1015                1020

Glu  Thr  Ala  Asp  Glu  Leu  Lys  Ile  Phe  Glu  Gly  Ile  Lys  His  Pro  Asn
1025                      1030                1035                         1040

Leu  Val  Arg  Tyr  Phe  Gly  Val  Glu  Leu  His  Arg  Glu  Glu  Met  Tyr  Ile
              1045                1050                     1055

Phe  Met  Glu  Tyr  Cys  Asp  Glu  Gly  Thr  Leu  Glu  Glu  Val  Ser  Arg  Leu
              1060                1065                     1070
```

```
Gly  Leu  Gln  Glu  His  Val  Ile  Arg  Leu  Tyr  Thr  Lys  Gln  Ile  Thr  Val
          1075                    1080                    1085

Ala  Ile  Asn  Val  Leu  His  Glu  His  Gly  Ile  Val  His  Arg  Asp  Ile  Lys
          1090                    1095                    1100

Gly  Ala  Asn  Ile  Phe  Leu  Thr  Ser  Ser  Gly  Leu  Ile  Lys  Leu  Gly  Asp
1105                    1110                    1115                    1120

Phe  Gly  Cys  Ser  Val  Lys  Leu  Lys  Asn  Asn  Ala  Gln  Thr  Met  Pro  Gly
                    1125                    1130                    1135

Glu  Val  Asn  Ser  Thr  Leu  Gly  Thr  Ala  Ala  Tyr  Met  Ala  Pro  Glu  Val
          1140                    1145                    1150

Ile  Thr  Arg  Ala  Lys  Gly  Glu  Gly  His  Gly  Arg  Ala  Ala  Asp  Ile  Trp
          1155                    1160                    1165

Ser  Leu  Gly  Cys  Val  Val  Ile  Glu  Met  Val  Thr  Gly  Lys  Arg  Pro  Trp
          1170                    1175                    1180

His  Glu  Tyr  Glu  His  Asn  Phe  Gln  Ile  Met  Tyr  Lys  Val  Gly  Met  Gly
1185                    1190                    1195                    1200

His  Lys  Pro  Pro  Ile  Pro  Glu  Arg  Leu  Ser  Pro  Glu  Gly  Lys  Ala  Phe
                    1205                    1210                    1215

Leu  Ser  His  Cys  Leu  Glu  Ser  Asp  Pro  Lys  Ile  Arg  Trp  Thr  Ala  Ser
                    1220                    1225                    1230

Gln  Leu  Leu  Asp  His  Ala  Phe  Val  Lys  Val  Cys  Thr  Asp  Glu  Glu
          1235                    1240                    1245
```

( 2 ) INFORMATION FOR SEQ ID NO:11:

( i ) SEQUENCE CHARACTERISTICS:
      ( A ) LENGTH: 2503 base pairs
      ( B ) TYPE: nucleic acid
      ( C ) STRANDEDNESS: double
      ( D ) TOPOLOGY: linear ( i i ) MOLECULE TYPE: cDNA ( i x ) FEATURE:
      ( A ) NAME/KEY: CDS
      ( B ) LOCATION: 466..2325

( x i ) SEQUENCE DESCRIPTION: SEQ ID NO:11:

```
GGTGGCGGCC  GCTCTAGAAC  TAGTGGATCC  CCCGGGCTGC  AGGAATTCGG  CACGAGGGAC     60

GATCCAGCGG  CAGAGTCGCC  GCTTCCGCTT  CGCTGCTTCT  CCGGTCGGCG  ACGCGGGCCC    120

GGGGCTTCCT  TTTCATCGGC  CCAGCTTATT  CCGCGGGCCC  CGGGGCTGCA  GCTACCCAGA    180

AGCGGCGAAG  AGGCCCTGGG  CTGCGCGCCC  GCTGTCCCAT  GTGAAGCAGG  TTGGGCCTGG    240

TCCCCGGCCC  GTGCCCGGTT  GTCTGCGGCC  CTTCAGGCCT  CAGGGACCCC  CGCGAGGCGC    300

TGCTCCTGGG  GGGCGCGGTG  ACAGGCCGTG  CGGGGGCGGA  GGGGCCAGCT  CGGTGGCCTC    360

CTCTCGGCCC  TCGCGTCCGC  GATCCCGCCC  AGCGGCCGGG  CAATAAAGAA  TGTTGATGGG    420

AGAACCATTT  TCCTAATTTT  CAAATTATTG  AGCTGGTCGC  GCATA  ATG GAT GAT        474
                                                      Met Asp Asp
                                                       1

CAG CAA GCT TTG AAT TCA ATC ATG CAA GAT TTG GCT GTC CTT CAT AAG         522
Gln Gln Ala Leu Asn Ser Ile Met Gln Asp Leu Ala Val Leu His Lys
     5               10                  15

GCC AGT CGG CCA GCA TTA TCT TTA CAA GAA ACC AGG AAA GCA AAA CCT         570
Ala Ser Arg Pro Ala Leu Ser Leu Gln Glu Thr Arg Lys Ala Lys Pro
 20              25                  30                  35

TCA TCA CCA AAA AAA CAG AAT GAT GTT CGA GTC AAA TTT GAA CAT AGA         618
Ser Ser Pro Lys Lys Gln Asn Asp Val Arg Val Lys Phe Glu His Arg
         40                  45                  50
```

```
GGA GAA AAA AGG ATC CTG CAG GTT ACT AGA CCA GTT AAA CTA GAA GAC        666
Gly Glu Lys Arg Ile Leu Gln Val Thr Arg Pro Val Lys Leu Glu Asp
            55                  60                  65

CTG AGA TCT AAG TCT AAG ATC GCC TTT GGG CAG TCT ATG GAT CTA CAC        714
Leu Arg Ser Lys Ser Lys Ile Ala Phe Gly Gln Ser Met Asp Leu His
            70                  75                  80

TAT ACC AAC AAT GAG TTG GTA ATT CCG TTA ACT ACC CAA GAT GAC TTG        762
Tyr Thr Asn Asn Glu Leu Val Ile Pro Leu Thr Thr Gln Asp Asp Leu
        85                  90                  95

GAC AAA GCT GTG GAA CTG CTG GAT CGC AGT ATT CAC ATG AAG AGT CTC        810
Asp Lys Ala Val Glu Leu Leu Asp Arg Ser Ile His Met Lys Ser Leu
100                 105                 110                 115

AAG ATA TTA CTT GTA GTA AAT GGG AGT ACA CAG GCT ACT AAT TTA GAA        858
Lys Ile Leu Leu Val Val Asn Gly Ser Thr Gln Ala Thr Asn Leu Glu
                    120                 125                 130

CCA TCA CCG TCA CCA GAA GAT TTG AAT AAT ACA CCA CTT GGT GCA GAG        906
Pro Ser Pro Ser Pro Glu Asp Leu Asn Asn Thr Pro Leu Gly Ala Glu
                135                 140                 145

AGG AAA AAG CGG CTA TCT GTA GTA GGT CCC CCT AAT AGG GAT AGA AGT        954
Arg Lys Lys Arg Leu Ser Val Val Gly Pro Pro Asn Arg Asp Arg Ser
        150                 155                 160

TCC CCT CCT CCA GGA TAC ATT CCA GAC ATA CTA CAC CAG ATT GCC CGG       1002
Ser Pro Pro Pro Gly Tyr Ile Pro Asp Ile Leu His Gln Ile Ala Arg
165                 170                 175

AAT GGG TCA TTC ACT AGC ATC AAC AGT GAA GGA GAG TTC ATT CCA GAG       1050
Asn Gly Ser Phe Thr Ser Ile Asn Ser Glu Gly Glu Phe Ile Pro Glu
180                 185                 190                 195

AGC ATG GAC CAA ATG CTG GAT CCA TTG TCT TTA AGC AGC CCT GAA AAT       1098
Ser Met Asp Gln Met Leu Asp Pro Leu Ser Leu Ser Ser Pro Glu Asn
                200                 205                 210

TCT GGC TCA GGA AGC TGT CCG TCA CTT GAT AGT CCT TTG GAT GGA GAA       1146
Ser Gly Ser Gly Ser Cys Pro Ser Leu Asp Ser Pro Leu Asp Gly Glu
        215                 220                 225

AGC TAC CCA AAA TCA CGG ATG CCT AGG GCA CAG AGC TAC CCA GAT AAT       1194
Ser Tyr Pro Lys Ser Arg Met Pro Arg Ala Gln Ser Tyr Pro Asp Asn
            230                 235                 240

CAT CAG GAG TTT ACA GAC TAT GAT AAC CCC ATT TTT GAG AAA TTT GGA       1242
His Gln Glu Phe Thr Asp Tyr Asp Asn Pro Ile Phe Glu Lys Phe Gly
        245                 250                 255

AAA GGA GGA ACA TAT CCA AGA AGG TAC CAC GTT TCC TAT CAT CAC CAG       1290
Lys Gly Gly Thr Tyr Pro Arg Arg Tyr His Val Ser Tyr His His Gln
260                 265                 270                 275

GAG TAT AAT GAC GGT CGG AAG ACT TTT CCA AGA GCT AGA AGG ACC CAG       1338
Glu Tyr Asn Asp Gly Arg Lys Thr Phe Pro Arg Ala Arg Arg Thr Gln
                280                 285                 290

GGC ACC AGT TTC CGG TCT CCT GTG AGC TTC AGT CCT ACT GAT CAC TCC       1386
Gly Thr Ser Phe Arg Ser Pro Val Ser Phe Ser Pro Thr Asp His Ser
        295                 300                 305

TTA AGC ACT AGT AGT GGA AGC AGT GTC TTT ACC CCA GAG TAT GAC GAC       1434
Leu Ser Thr Ser Ser Gly Ser Ser Val Phe Thr Pro Glu Tyr Asp Asp
            310                 315                 320

AGT CGA ATA AGA AGA CGG GGG AGT GAC ATA GAC AAT CCT ACT TTG ACT       1482
Ser Arg Ile Arg Arg Arg Gly Ser Asp Ile Asp Asn Pro Thr Leu Thr
        325                 330                 335

GTC ACA GAC ATC AGC CCA CCC AGC CGT TCA CCT CGA GCT CCG ACC AAC       1530
Val Thr Asp Ile Ser Pro Pro Ser Arg Ser Pro Arg Ala Pro Thr Asn
340                 345                 350                 355

TGG AGA CTG GGC AAG CTG CTT GGC CAA GGA GCT TTT GGT AGG GTC TAC       1578
Trp Arg Leu Gly Lys Leu Leu Gly Gln Gly Ala Phe Gly Arg Val Tyr
                360                 365                 370
```

| | | | | | | | | | | | | | | | | |
|---|---|---|---|---|---|---|---|---|---|---|---|---|---|---|---|---|
| CTC | TGC | TAT | GAT | GTT | GAT | ACC | GGA | AGA | GAG | CTG | GCT | GTT | AAG | CAA | GTT | 1626 |
| Leu | Cys | Tyr | Asp | Val | Asp | Thr | Gly | Arg | Glu | Leu | Ala | Val | Lys | Gln | Val | |
| | | 375 | | | | 380 | | | | | 385 | | | | | |
| CAG | TTT | AAC | CCT | GAG | AGC | CCA | GAG | ACC | AGC | AAG | GAA | GTA | AAT | GCA | CTT | 1674 |
| Gln | Phe | Asn | Pro | Glu | Ser | Pro | Glu | Thr | Ser | Lys | Glu | Val | Asn | Ala | Leu | |
| | | 390 | | | | | 395 | | | | | 400 | | | | |
| GAG | TGT | GAA | ATT | CAG | TTG | TTG | AAA | AAC | TTG | TTG | CAT | GAG | CGA | ATT | GTT | 1722 |
| Glu | Cys | Glu | Ile | Gln | Leu | Leu | Lys | Asn | Leu | Leu | His | Glu | Arg | Ile | Val | |
| | 405 | | | | | 410 | | | | | 415 | | | | | |
| CAG | TAT | TAT | GGC | TGT | TTG | AGG | GAT | CCT | CAG | GAG | AAA | ACA | CTT | TCC | ATC | 1770 |
| Gln | Tyr | Tyr | Gly | Cys | Leu | Arg | Asp | Pro | Gln | Glu | Lys | Thr | Leu | Ser | Ile | |
| 420 | | | | | 425 | | | | 430 | | | | | | 435 | |
| TTT | ATG | GAG | TAT | ATG | CCA | GGG | GGT | TCA | ATT | AAG | GAC | CAA | CTA | AAA | GCC | 1818 |
| Phe | Met | Glu | Tyr | Met | Pro | Gly | Gly | Ser | Ile | Lys | Asp | Gln | Leu | Lys | Ala | |
| | | | | 440 | | | | | 445 | | | | | 450 | | |
| TAC | GGA | GCT | CTT | ACT | GAG | AAC | GTG | ACG | AGG | AAG | TAC | ACC | CGT | CAG | ATT | 1866 |
| Tyr | Gly | Ala | Leu | Thr | Glu | Asn | Val | Thr | Arg | Lys | Tyr | Thr | Arg | Gln | Ile | |
| | | | 455 | | | | | 460 | | | | | 465 | | | |
| CTG | GAG | GGG | GTC | CAT | TAT | TTG | CAT | AGT | AAT | ATG | ATT | GTC | CAT | AGA | GAT | 1914 |
| Leu | Glu | Gly | Val | His | Tyr | Leu | His | Ser | Asn | Met | Ile | Val | His | Arg | Asp | |
| | | 470 | | | | | 475 | | | | | 480 | | | | |
| ATC | AAA | GGA | GCA | AAT | ATC | TTA | AGG | GAT | TCC | ACA | GGC | AAT | ATC | AAG | TTA | 1962 |
| Ile | Lys | Gly | Ala | Asn | Ile | Leu | Arg | Asp | Ser | Thr | Gly | Asn | Ile | Lys | Leu | |
| | 485 | | | | | 490 | | | | | 495 | | | | | |
| GGA | GAC | TTT | GGG | GCT | AGT | AAA | CGG | CTT | CAG | ACC | ATC | TGT | CTC | TCA | GGC | 2010 |
| Gly | Asp | Phe | Gly | Ala | Ser | Lys | Arg | Leu | Gln | Thr | Ile | Cys | Leu | Ser | Gly | |
| 500 | | | | | 505 | | | | | 510 | | | | | 515 | |
| ACA | GGA | ATG | AAG | TCT | GTC | ACA | GGC | ACG | CCA | TAC | TGG | ATG | AGT | CCT | GAG | 2058 |
| Thr | Gly | Met | Lys | Ser | Val | Thr | Gly | Thr | Pro | Tyr | Trp | Met | Ser | Pro | Glu | |
| | | | | 520 | | | | | 525 | | | | | 530 | | |
| GTC | ATC | AGT | GGA | GAA | GGC | TAT | GGA | AGA | AAA | GCA | GAC | ATC | TGG | AGT | GTA | 2106 |
| Val | Ile | Ser | Gly | Glu | Gly | Tyr | Gly | Arg | Lys | Ala | Asp | Ile | Trp | Ser | Val | |
| | | | 535 | | | | | 540 | | | | | 545 | | | |
| GCA | TGT | ACT | GTG | GTA | GAA | ATG | CTA | ACT | GAA | AAG | CCA | CCT | TGG | GCT | GAA | 2154 |
| Ala | Cys | Thr | Val | Val | Glu | Met | Leu | Thr | Glu | Lys | Pro | Pro | Trp | Ala | Glu | |
| | | 550 | | | | | 555 | | | | | 560 | | | | |
| TTT | GAA | GCA | ATG | GCT | GCC | ATC | TTT | AAG | ATC | GCC | ACT | CAG | CCA | ACG | AAC | 2202 |
| Phe | Glu | Ala | Met | Ala | Ala | Ile | Phe | Lys | Ile | Ala | Thr | Gln | Pro | Thr | Asn | |
| | 565 | | | | | 570 | | | | | 575 | | | | | |
| CCA | AAG | CTG | CCA | CCT | CAT | GTC | TCA | GAC | TAT | ACT | CGG | GAC | TTC | CTC | AAA | 2250 |
| Pro | Lys | Leu | Pro | Pro | His | Val | Ser | Asp | Tyr | Thr | Arg | Asp | Phe | Leu | Lys | |
| 580 | | | | | 585 | | | | | 590 | | | | | 595 | |
| CGG | ATT | TTT | GTA | GAG | GCC | AAA | CTT | CGA | CCT | TCA | GCG | GAG | GAG | CTC | TTG | 2298 |
| Arg | Ile | Phe | Val | Glu | Ala | Lys | Leu | Arg | Pro | Ser | Ala | Glu | Glu | Leu | Leu | |
| | | | | 600 | | | | | 605 | | | | | 610 | | |
| CGG | CAC | ATG | TTT | GTG | CAT | TAT | CAC | TAGCAGCGGC | GGCTTCGGTC | CTCCACCAGC | | | | | | 2352 |
| Arg | His | Met | Phe | Val | His | Tyr | His | | | | | | | | | |
| | | | 615 | | | | | 620 | | | | | | | | |

TCCATCCTCG CGGCCACCTT CTCTCTTACT GCACTTTCCT TTTTTATAAA AAAGAGAGAT 2412

GGGGAGAAAA AGACAAGAGG GAAAATATTT CTCTTGATTC TTGGTTAAAT TTGTTTAATA 2472

ATAATAGTAA ACTAAAAAAA AAAAAAAAAA A 2503

( 2 ) INFORMATION FOR SEQ ID NO:12:

( i ) SEQUENCE CHARACTERISTICS:
        ( A ) LENGTH: 619 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

| | | | | | | | | | | | | | | |
|---|---|---|---|---|---|---|---|---|---|---|---|---|---|---|
| Met<br>1 | Asp | Asp | Gln | Gln<br>5 | Ala | Leu | Asn | Ser | Ile<br>10 | Met | Gln | Asp | Leu | Ala<br>15 | Val |
| Leu | His | Lys | Ala<br>20 | Ser | Arg | Pro | Ala | Leu<br>25 | Ser | Leu | Gln | Glu | Thr<br>30 | Arg | Lys |
| Ala | Lys | Pro<br>35 | Ser | Ser | Pro | Lys | Lys<br>40 | Gln | Asn | Asp | Val | Arg<br>45 | Val | Lys | Phe |
| Glu | His<br>50 | Arg | Gly | Glu | Lys | Arg<br>55 | Ile | Leu | Gln | Val | Thr<br>60 | Arg | Pro | Val | Lys |
| Leu<br>65 | Glu | Asp | Leu | Arg | Ser<br>70 | Lys | Ser | Lys | Ile | Ala<br>75 | Phe | Gly | Gln | Ser | Met<br>80 |
| Asp | Leu | His | Tyr | Thr<br>85 | Asn | Asn | Glu | Leu | Val<br>90 | Ile | Pro | Leu | Thr | Thr<br>95 | Gln |
| Asp | Asp | Leu | Asp<br>100 | Lys | Ala | Val | Glu | Leu<br>105 | Leu | Asp | Arg | Ser | Ile<br>110 | His | Met |
| Lys | Ser | Leu<br>115 | Lys | Ile | Leu | Leu | Val<br>120 | Val | Asn | Gly | Ser | Thr<br>125 | Gln | Ala | Thr |
| Asn | Leu<br>130 | Glu | Pro | Ser | Pro | Ser<br>135 | Pro | Glu | Asp | Leu | Asn<br>140 | Asn | Thr | Pro | Leu |
| Gly<br>145 | Ala | Glu | Arg | Lys | Lys<br>150 | Arg | Leu | Ser | Val | Val<br>155 | Gly | Pro | Pro | Asn | Arg<br>160 |
| Asp | Arg | Ser | Ser | Pro<br>165 | Pro | Pro | Gly | Tyr | Ile<br>170 | Pro | Asp | Ile | Leu | His<br>175 | Gln |
| Ile | Ala | Arg | Asn<br>180 | Gly | Ser | Phe | Thr | Ser<br>185 | Ile | Asn | Ser | Glu | Gly<br>190 | Glu | Phe |
| Ile | Pro | Glu<br>195 | Ser | Met | Asp | Gln | Met<br>200 | Leu | Asp | Pro | Leu | Ser<br>205 | Leu | Ser | Ser |
| Pro | Glu<br>210 | Asn | Ser | Gly | Ser | Gly<br>215 | Ser | Cys | Pro | Ser | Leu<br>220 | Asp | Ser | Pro | Leu |
| Asp<br>225 | Gly | Glu | Ser | Tyr | Pro<br>230 | Lys | Ser | Arg | Met | Pro<br>235 | Arg | Ala | Gln | Ser | Tyr<br>240 |
| Pro | Asp | Asn | His | Gln<br>245 | Glu | Phe | Thr | Asp | Tyr<br>250 | Asp | Asn | Pro | Ile | Phe<br>255 | Glu |
| Lys | Phe | Gly | Lys<br>260 | Gly | Gly | Thr | Tyr | Pro<br>265 | Arg | Arg | Tyr | His | Val<br>270 | Ser | Tyr |
| His | His | Gln<br>275 | Glu | Tyr | Asn | Asp | Gly<br>280 | Arg | Lys | Thr | Phe | Pro<br>285 | Arg | Ala | Arg |
| Arg | Thr<br>290 | Gln | Gly | Thr | Ser | Phe<br>295 | Arg | Ser | Pro | Val | Ser<br>300 | Phe | Ser | Pro | Thr |
| Asp<br>305 | His | Ser | Leu | Ser | Thr<br>310 | Ser | Ser | Gly | Ser | Ser<br>315 | Val | Phe | Thr | Pro | Glu<br>320 |
| Tyr | Asp | Asp | Ser | Arg<br>325 | Ile | Arg | Arg | Gly<br>330 | Ser | Asp | Ile | Asp | Asn<br>335 | Pro |
| Thr | Leu | Thr | Val<br>340 | Thr | Asp | Ile | Ser | Pro<br>345 | Pro | Ser | Arg | Ser | Pro<br>350 | Arg | Ala |
| Pro | Thr | Asn<br>355 | Trp | Arg | Leu | Gly | Lys<br>360 | Leu | Leu | Gly | Gln | Gly<br>365 | Ala | Phe | Gly |
| Arg | Val<br>370 | Tyr | Leu | Cys | Tyr | Asp<br>375 | Val | Asp | Thr | Gly | Arg<br>380 | Glu | Leu | Ala | Val |
| Lys<br>385 | Gln | Val | Gln | Phe | Asn<br>390 | Pro | Glu | Ser | Pro | Glu<br>395 | Thr | Ser | Lys | Glu | Val<br>400 |
| Asn | Ala | Leu | Glu | Cys<br>405 | Glu | Ile | Gln | Leu | Leu<br>410 | Lys | Asn | Leu | Leu | His<br>415 | Glu |

| | | | | | | | | | | | | | | |
|---|---|---|---|---|---|---|---|---|---|---|---|---|---|---|
| Arg | Ile | Val | Gln 420 | Tyr | Tyr | Gly | Cys | Leu 425 | Arg | Asp | Pro | Gln | Glu 430 | Lys | Thr |
| Leu | Ser | Ile 435 | Phe | Met | Glu | Tyr | Met 440 | Pro | Gly | Gly | Ser | Ile 445 | Lys | Asp | Gln |
| Leu | Lys 450 | Ala | Tyr | Gly | Ala | Leu 455 | Thr | Glu | Asn | Val | Thr 460 | Arg | Lys | Tyr | Thr |
| Arg 465 | Gln | Ile | Leu | Glu | Gly 470 | Val | His | Tyr | Leu | His 475 | Ser | Asn | Met | Ile | Val 480 |
| His | Arg | Asp | Ile | Lys 485 | Gly | Ala | Asn | Ile | Leu 490 | Arg | Asp | Ser | Thr | Gly 495 | Asn |
| Ile | Lys | Leu | Gly 500 | Asp | Phe | Gly | Ala | Ser 505 | Lys | Arg | Leu | Gln | Thr 510 | Ile | Cys |
| Leu | Ser | Gly 515 | Thr | Gly | Met | Lys | Ser 520 | Val | Thr | Gly | Thr | Pro 525 | Tyr | Trp | Met |
| Ser | Pro 530 | Glu | Val | Ile | Ser | Gly 535 | Glu | Gly | Tyr | Gly | Arg 540 | Lys | Ala | Asp | Ile |
| Trp 545 | Ser | Val | Ala | Cys | Thr 550 | Val | Val | Glu | Met | Leu 555 | Thr | Glu | Lys | Pro | Pro 560 |
| Trp | Ala | Glu | Phe | Glu 565 | Ala | Met | Ala | Ala | Ile 570 | Phe | Lys | Ile | Ala | Thr 575 | Gln |
| Pro | Thr | Asn | Pro 580 | Lys | Leu | Pro | Pro | His 585 | Val | Ser | Asp | Tyr | Thr 590 | Arg | Asp |
| Phe | Leu | Lys 595 | Arg | Ile | Phe | Val | Glu 600 | Ala | Lys | Leu | Arg | Pro 605 | Ser | Ala | Glu |
| Glu | Leu 610 | Leu | Arg | His | Met | Phe 615 | Val | His | Tyr | His | | | | | |

MITOGEN ERK KINASE KINASE (MEKK) ASSAY

CROSS-REFERENCE TO RELATED APPLICATIONS

The present application is a continuation-in-part application of U.S. patent application Ser. No. 08/440,421, entitled "Method and Product for Regulating Cell Responsiveness to External Signals", filed May 12, 1995, which is a continuation-in-part of U.S. patent application Ser. No. 08/354,516 entitled "Method and Product for Regulating Cell Responsiveness to External Signals", now abandoned filed Feb. 21, 1995, which is a divisional application of U.S. patent application Ser. No. 08/049,254, filed Apr. 15, 1993, now U.S. Pat. No. 5,405,941 entitled "MEKK Protein, Capable of Phosphorylating MEK", issued Apr. 11, 1995. The present application is also a continuation-in-part of U.S. patent application Ser. No. 08/323,460 entitled "Method and Product for Regulating Cell Responsiveness to External Signals", filed Oct. 14, 1994; PCT Application No. PCT/US94/11690 entitled "Method and Product for Regulating Cell Responsiveness to External Signals", filed Oct. 14, 1994; published as WO95/28421 Oct. 26, 1995 and PCT Application No. PCT/US94/04178 for "Method and Product for Regulating Cell Responsiveness to External Signals", filed Apr. 15, 1994, published as WO94/24159 Oct. 27, 1994, all of which are continuation-in-part applications of U.S. patent application Ser. No. 08/049,254, now U.S. Pat. No. 5,405,941. The above-referenced patents and patent applications are incorporated herein by this reference in their entirety.

This invention was made in part with government support under USPHS Grant DK37871, USPHS Grant GM30324 and AI21768, both awarded by the National Institutes of Health. The government has certain rights to this invention.

FIELD OF THE INVENTION

This invention relates to isolated nucleic acid molecules encoding MEKK proteins, substantially pure MEKK proteins, and products and methods for regulating signal transduction in a cell.

BACKGROUND OF THE INVENTION

Mitogen-activated protein kinase (MAPKs) (also called extracellular signal-regulated kinases or ERKs) are rapidly activated in response to ligand binding by both growth factor receptors that are tyrosine kinases (such as the epidermal growth factor (EGF) receptor) and receptors that are coupled to heterotrimeric guanine nucleotide binding proteins (G proteins) such as the thrombin receptor. The MAPKs appear to integrate multiple intracellular signals transmitted by various second messengers. MAPKs phosphorylate and regulate the activity of enzymes and transcription factors including the EGF receptor, Rsk 90, phospholipase $A_2$, c-Myc, c-Jun and Elk-1/TCF. Although the rapid activation of MAPKs by receptors that are tyrosine kinases is dependent on Ras, G protein-mediated activation of MAPK appears to occur through pathways dependent and independent of Ras.

Complementation analysis of the pheromone-induced signaling pathway in yeast has defined a protein kinase system that controls the activity of Spk1 and Fus3-Kss1, the *Schizosaccharomyces pombe* and *Saccharomyces cerevisiae* homologs of MAPK (see for example, B. R. Cairns et al., *Genes and Dev.* 6, 1305 (1992); B. J. Stevenson et al., *Genes and Dev.* 6, 1293 (1992); S. A. Nadin-Davis et al., *EMBO J.* 7, 985 (1988); Y. Wang et al., *Mol. Cell. Biol.* 11, 3554 (1991). In *S. cerevisiae*, the protein kinase Ste7 is the upstream regulator of Fus3-Kss1 activity; the protein kinase Ste11 regulates Ste7. The S. pombe gene products Byr1 and Byr2 are homologous to Ste7 and Ste11, respectively. The MEK (MAPK Kinase or ERK Kinase) or MKK (MAP Kinase kinase) enzymes are similar in sequence to Ste7 and Byr1. The MEKs phosphorylate MAPKs on both tyrosine and threonine residues which results in activation of MAPK. The mammalian serine-threonine protein kinase Raf phosphorylates and activates MEK, which leads to activation of MAPK. Raf is activated in response to growth factor receptor tyrosine kinase activity and therefore Raf may activate MAPK in response to stimulation of membrane-associated tyrosine kinases. Raf is unrelated in sequence to Ste11 and Byr2. Thus, Raf may represent a divergence in mammalian cells from the pheromone-responsive protein kinase system defined in yeast. Cell and receptor specific differences in the regulation of MAPKs suggest that other Raf independent regulators of mammalian MEKs exist.

Certain biological functions, such as growth and differentiation, are tightly regulated by signal transduction pathways within cells. Signal transduction pathways maintain the balanced steady state functioning of a cell. Disease states can arise when signal transduction in a cell breaks down, thereby removing the tight control that typically exists over cellular functions. For example, tumors develop when regulation of cell growth is disrupted enabling a clone of cells to expand indefinitely. Because signal transduction networks regulate a multitude of cellular functions depending upon the cell type, a wide variety of diseases can result from abnormalities in such networks. Devastating diseases such as cancer, autoimmune diseases, allergic reactions, inflammation, neurological disorders and hormone-related diseases can result from abnormal signal transduction.

Despite a long-felt need to understand and discover methods for regulating cells involved in various disease states, the complexity of signal transduction pathways has precluded the development of products and processes for regulating cellular function by manipulating signal transduction pathways in a cell. As such, there remains a need for products and processes that permit the implementation of predictable controls of signal transduction in cells, thus enabling the treatment of various diseases that are caused by abnormal cellular function.

SUMMARY OF THE INVENTION

The present invention provides a solution to the complex problem of identifying putative regulatory compounds which can be used to regulate cellular responses. Despite the complexity of signal transduction networks in cells, the present invention provides for an efficient method for identifying compounds capable of specifically regulating signal transduction in a cell, preferably through identifying signal transduction pathways regulated by such compounds, and more preferably through identifying a site of activity of a putative regulatory compound within a complex signal transduction pathway. In particular, the present invention provides a method to the identify compounds that act at a specific site in a signal transduction pathway involving MEKK protein.

The present application incorporates herein by this reference in their entirety all subject matter as taught in related U.S. patent application Ser. No. 08/440,421, entitled "METHOD AND PRODUCT FOR REGULATING CELL RESPONSIVENESS TO EXTERNAL SIGNALS," filed May 15, 1995; U.S. patent application Ser. No. 08/410,602, entitled "AN ASSAY AND METHOD FOR SCREENING CELL REGULATORY REAGENTS," filed Mar. 24, 1995; U.S. patent application Ser. No. 08/354,516 entitled "METHOD AND PRODUCT FOR REGULATING CELL RESPONSIVENESS TO EXTERNAL SIGNALS," filed Dec. 13, 1994; U.S. Pat. Ser. No. 5,405,941, entitled "MEKK PROTEIN, CAPABLE OF PHOSPHORYLATING MEK," issued Apr. 11, 1995; U.S. patent application Ser. No. 08/323,460, entitled "METHOD AND PRODUCT FOR REGULATING CELL RESPONSIVENESS TO EXTERNAL SIGNALS," filed Oct. 14, 1994; and as taught in related PCT Application No. PCT/US94/11690, entitled "METHOD AND PRODUCT FOR REGULATING CELL RESPONSIVENESS TO EXTERNAL SIGNALS," filed Oct. 14, 1994; and PCT Application No. PCT/US94/04178 for "METHOD AND PRODUCT FOR REGULATING CELL RESPONSIVENESS TO EXTERNAL SIGNALS," filed Apr. 15, 1994.

In particular, the present invention provides a method for identifying compounds which specifically regulate the activity of elements of the raf-independent arm of the MEK kinase (MEKK) pathway. Such MEKK pathway includes MEKK, Jun kinase kinase (JNKK) and other members of the MEK pathway, which in turn regulate the activity of signalling molecules such as MAPK, p38 and JNK. Those of skill in the art will immediately recognize the advantages arising from this invention which include the identification and uses of compounds which act to specifically modify the activity of a signal transduction pathway involving MEKK protein.

The present invention provides for an assay using cells having signal transduction pathways involving MEKK to identify regulatory compounds capable of altering signal transduction in a cell and determining at which step of signal transduction pathway the compound exerts its effect.

One embodiment of the present invention includes a method to identify compounds capable of regulating a signal transduction pathway in a cell, comprising: (a) contacting a cell having a signal transduction pathway with a putative regulatory compound, in which one of the signal transduction pathways includes an MEKK protein of the present invention; and (b) assessing the ability of the putative regulatory compound to regulate signal transduction in the cell by measuring the phosphorylation of proteins including MAPK, JNK, p38, MEKK, JNKK, Syk, Fyn, and Lyn protein. In particular, the step of assessing is performed using antibodies including anti-MEKK, anti-MAPK, anti-JNK, anti-p38, anti-MEK, anti-JNKK, anti-Syk, anti-Fyn, anti-Lyn and anti-phosphotyrosine antibodies.

The present invention also includes a method to identify a non-toxic signal transduction regulator that is capable of regulating an MEKK signal transduction pathway in a mammalian cell, in which the signal transduction regulator is identified by contacting a putative regulatory compound with at least one compound involved in an MEKK signal transduction pathway and identifying a signal transduction regulator by assessing the ability of the putative regulatory compound to regulate the MEKK signal transduction pathway, the method comprising contacting the signal transduction regulator with a mammalian cell having a signal transduction pathway, and assessing: (a) the ability of the signal transduction regulator to regulate the MEKK signal transduction pathway; and (b) the toxicity of the signal transduction regulator on the mammalian cell. In particular, the step of assessing toxicity is measured by Coomassie blue staining, acridine orange staining, terminal deoxynucelotidyl transferase (TDT) assays, neutral red exclusion, measuring changes in forward light scattering in a flow cytometer, and measuring changes in redox potential of a cell or its ability to reduce a chromogenic substrate.

One aspect of the present invention is a method to identify compounds capable of regulating an MEKK signal transduction pathway in a cell, comprising: (a) contacting a putative regulatory compound of a signal transduction pathway with a recombinant cell transfected with at least one nucleic acid molecule encoding a transcription factor and a reporter protein, and having a transcriptional activator binding nucleic acid sequence, in which the protein encoded by the transcription factor nucleic acid molecule, and the transcriptional activator binding nucleic acid sequence, are capable of regulating the transcription of the reporter protein nucleic acid molecule; and (b) assessing the ability of the putative regulatory compound to regulate the expression, of the reporter protein. Preferably, the recombinant cell has an activator recombinant molecule comprising a nucleic acid molecule operatively linked to an expression vector, the nucleic acid molecule encoding at least one transcription factor and at least one transcriptional activator. In addition, the recombinant cell can further comprise a reporter recombinant molecule comprising a nucleic acid molecule operatively linked to an expression vector, the nucleic acid molecule having at least one transcriptional activator binding nucleic acid sequence and at least one nucleic acid sequence encoding a reporter protein.

Yet another aspect of the present invention includes a method to identify compounds capable of regulating a biological response in a mammal, comprising: (a) contacting a mammalian cell with a putative regulatory compound, in which the mammalian cell has a signal transduction pathway involving MEKK; (b) assessing the ability of the putative regulatory compound to specifically regulate the activity of the signal transduction pathway by determining the phosphorylation of MEKK; and (c) administering the putative regulatory compound to an animal to determine the effectiveness of the putative regulatory compound in the regulation of a biological response in the animal, in which the biological response includes an inflammatory response, a response to an infectious agent, an autoimmune response, a metabolic response, a cardiovascular response, an allergic response and an abnormal cellular growth response.

DETAILED DESCRIPTION OF THE INVENTION

The present invention relates to a novel mitogen ERK kinase kinase protein (MEKK) capable of regulating signal transduction in cells. The present invention includes a novel method for treating disease by regulating the activity of cells involved in such disease. The present invention is particularly advantageous in that the novel product and method of the present invention is capable of regulating a signal transduction pathway that can lead to cellular apoptosis.

One embodiment of the present invention is an isolated MEKK protein. According to the present invention, an isolated protein is a protein that has been removed from its natural milieu. An isolated MEKK protein can, for example, be obtained from its natural source, be produced using recombinant DNA technology, or be synthesized chemically. As used herein, an isolated MEKK protein can be a full-length MEKK protein or any homologue of such a protein, such as an MEKK protein in which amino acids have been deleted (e.g., a truncated version of the protein, such as a peptide), inserted, inverted, substituted and/or derivatized (e.g., by glycosylation, phosphorylation, acetylation, myristoylation, prenylation, palmitoylation, amidation and/or addition of glycosylphosphatidyl inositol), wherein the modified protein is capable of phosphorylating mitogen ERK kinase (MEK) and/or Jun ERK kinase (JEK). A homologue of an MEKK protein is a protein having an amino acid sequence that is sufficiently similar to a natural MEKK protein amino acid sequence that a nucleic acid sequence encoding the homologue is capable of hybridizing under stringent conditions to (i.e., with) a nucleic acid sequence encoding the natural MEKK protein amino acid sequence. As used herein, stringent hybridization conditions refer to standard hybridization conditions under which nucleic acid molecules, including oligonucleotides, are used to identify similar nucleic acid molecules. Such standard conditions are disclosed, for example, in Sambrook et al., *Molecular Cloning: A Laboratory Manual*, Cold Spring Harbor Labs Press, 1989. A homologue of an MEKK protein also includes a protein having an amino acid sequence that is sufficiently cross-reactive such that the homologue has the ability to elicit an immune response against at least one epitope of a naturally-occurring MEKK protein.

The minimal size of a protein homologue of the present invention is a size sufficient to be encoded by a nucleic acid molecule capable of forming a stable hybrid with the complementary sequence of a nucleic acid molecule encoding the corresponding natural protein. As such, the size of the nucleic acid molecule encoding such a protein homologue is dependent on nucleic acid composition, percent homology between the nucleic acid molecule and complementary sequence, as well as upon hybridization conditions per se (e.g., temperature, salt concentration, and formamide concentration). The minimal size of such nucleic acid molecules is typically at least about 12 to about 15 nucleotides in length if the nucleic acid molecules are GC-rich and at least about 15 to about 17 bases in length if they are AT-rich. As such, the minimal size of a nucleic acid molecule used to encode an MEKK protein homologue of the present invention is from about 12 to about 18 nucleotides in length. There is no limit, other than a practical limit, on the maximal size of such a nucleic acid molecule in that the nucleic acid molecule can include a portion of a gene, an entire gene, or multiple genes, or portions thereof. Similarly, the minimal size of an MEKK protein homologue of the present invention is from about 4 to about 6 amino acids in length, with preferred sizes depending on whether a full-length, multivalent protein (i.e., fusion protein having more than one domain each of which has a function), or a functional portion of such a protein is desired.

MEKK protein homologues can be the result of allelic variation of a natural gene encoding an NEKK protein. A natural gene refers to the form of the gene found most often in nature. MEKK protein homologues can be produced using techniques known in the art including, but not limited to, direct modifications to a gene encoding a protein using, for example, classic or recombinant DNA techniques to effect random or targeted mutagenesis. The ability of an MEKK protein homologue to phosphorylate MEK and/or JEK protein can be tested using techniques known to those skilled in the art. Such techniques include phosphorylation assays described in detail in the Examples section.

In one embodiment, an MEKK protein of the present invention is capable of regulating an MEKK-dependent pathway. According to the present invention, an MEKK-dependent pathway refers generally to a pathway in which MEKK protein regulates a pathway substantially independent of Raf, and a pathway in which MEKK protein regulation converges with common members of a pathway involving Raf protein, in particular, MEK protein. A suitable MEKK-dependent pathway includes a pathway involving MEKK protein and JEK protein, but not Raf protein. One of skill in the art can determine that regulation of a pathway by an MEKK protein is substantially independent of Raf protein by comparing the ability of an MEKK protein and a Raf protein to regulate the phosphorylation of a downstream member of such pathway using, for example, the general method described in related U.S. patent application Ser. No. 08/440,421, entitled "METHOD AND PRODUCT FOR REGULATING CELL RESPONSIVENESS TO EXTERNAL SIGNALS," filed May 15, 1995. An MEKK protein regulates a pathway substantially independently of Raf protein if the MEKK protein induces phosphorylation of a member of the pathway downstream of MEKK (e.g., proteins including JEK, Jun kinase, Jun and/or ATF-2) by an amount significantly greater than that seen when Raf protein is utilized. For example, MEKK induction of phosphorylation of JNK is preferably at least about 10-fold, more preferably at least about 20-fold and even more preferably at least about 30-fold, greater phosphorylation of JNK protein than the phosphorylation induced when using Raf protein. If MEKK induction of phosphorylation is similar to Raf protein induction of phosphorylation, then one of skill in the art can conclude that regulation of a pathway by an MEKK protein includes members of a signal transduction pathway that could also include Raf protein. For example, MEKK induction of phosphorylation of NAPK is of a similar magnitude as induction of phosphorylation with Raf protein.

A "Raf-dependent pathway" can refer to a signal transduction pathway in which Raf protein regulates a signal transduction pathway substantially independently of MEKK protein, and a pathway in which Raf protein regulation converges with common members of a pathway involving MEKK protein. The independence of regulation of a pathway by a Raf protein from regulation of a pathway by an MEKK protein can be determined using methods similar to those used to determine MEKK independence.

In another embodiment, an MEKK protein is capable of regulating the activity of signal transduction proteins including, but not limited to, mitogen ERK kinase (MEK), mitogen activated protein kinase (MAPK), transcription control factor (TCF), Ets-like-1 transcription factor (Elk-1), Jun ERK kinase (JEK), Jun kinase (JNK; which is equivalent to SAPK), stress activated MAPK proteins, Jun, activating transcription factor-2 (ATF-2) and/or Myc protein. As used herein, the "activity" of a protein can be directly correlated with the phosphorylation state of the protein and/or the ability of the protein to perform a particular function (e.g., phosphorylate another protein or regulate transcription). Preferred MEK proteins regulated by an MEKK protein of the present invention include MEK-1 and/or MEK-2. Preferred MAPK proteins regulated by an MEKK protein of the present invention include p38 MAPK, p42 MAPK (which is equivalent to ERK2) and/or p44 (which is equivalent to ERK1) MAPK. Preferred stress activated MAPK proteins regulated by an MEKK protein of the present invention include Jun kinase (JNK), stress activated MAPK-α and/or stress activated MAPK-β.

An MEKK protein of the present invention is capable of increasing the activity of an MEK protein over basal levels of MEK (i.e., levels found in nature when not stimulated). For example, an MEKK protein is preferably capable of increasing the phosphorylation of an MEK protein by at least about 2-fold, more preferably at least about 3-fold, and even more referably at least about 4-fold over basal levels when measured under conditions described in related U.S. patent application Ser. No. 08/440,421, entitled "METHOD AND PRODUCT FOR REGULATING CELL RESPONSIVENESS TO EXTERNAL SIGNALS," filed May 15, 1995.

A preferred MEKK protein of the present invention is also capable of increasing the activity of an MAPK protein over basal levels of MAPK (i.e., levels found in nature when not stimulated). For example, an MEKK protein of the present invention is preferably capable of increasing MAPK activity at least about 2-fold, more preferably at least about 3-fold, and even more preferably at least about 4-fold over basal activity when measured under the conditions described in related U.S. patent application Ser. No. 008/440,421, entitled "METHOD AND PRODUCT FOR REGULATING CELL RESPONSIVENESS TO EXTERNAL SIGNALS," filed May 15, 1995.

Moreover, an MEKK protein of the present invention is capable of increasing the activity of a JNK protein. JNK regulates the activity of the transcription factor JUN which is involved in controlling the growth and differentiation of different cell types, such as T cells, neural cells or fibroblasts. JNK shows structural and regulatory homologies with MAPK. For example, an MEKK protein of the present invention is preferably capable of inducing the phosphorylation of JNK protein at least about 30 times more than Raf, more preferably at least about 40 times more than Raf, and even more preferably at least about 50 times more than Raf, when measured under conditions described in related U.S. patent application Ser. No. 08/440,421, entitled "METHOD AND PRODUCT FOR REGULATING CELL RESPONSIVENESS TO EXTERNAL SIGNALS," filed May 15, 1995.

In addition, an MEKK protein of the present invention is capable of binding to Ras protein. In particular, an MEKK protein is capable of binding to a Ras protein that is associated with GTP. According to the present invention, an MEKK protein binds to Ras via the COOH terminal region of the MEKK protein.

In a preferred embodiment, an MEKK protein of the present invention is capable of phosphorylating MEK, MKK, Jun kinase kinase (JNKK) and stress activated ERK kinase (SEK), in particular MEK1, MEK2, MKK1, MKK2, MKK3, MKK4, JNKK1, JNKK2, SEK1 and SEK2 protein. As described herein, MEK1 and MEK2 are equivalent to MKK1 and MKK2, respectively and are referred to 20 as MEK1 and MEK2. In addition, JNKK1 and JNKK2 are equivalent to MKK3 and MKK4, which are equivalent to SEK1 and SEK2, respectively, and are referred to herein as JNKK1 and JNKK2.

A preferred MEKK protein of the present invention is additionally capable of inducing the phosphorylation of a c-Myc transcriptional transactivation domain protein in such a manner that the phosphorylated transcriptional transactivation domain of c-Myc is capable of regulating gene transcription. The ability of an MEKK protein to regulate phosphorylation of a c-Myc transcriptional transactivation domain protein exceeds the ability of Raf protein or cyclic AMP-dependent protein kinase to regulate a c-Myc protein. For example, an NEKK protein of the present invention is preferably capable of inducing luciferase gene transcription by phosphorylated c-Myc transcriptional transctivation domain protein at least about 25-fold, more preferably at least about 35-fold, and even more preferably at least about 45-fold, over Raf induction when measured under the conditions described in related U.S. patent application Ser. No. 08/440, 421entitled "METHOD AND PRODUCT FOR REGULATING CELL RESPONSIVENESS TO EXTERNAL SIGNALS," filed May 15, 1995.

Another aspect of the present invention relates to the ability of MEKK activity to be stimulated by growth factors including, but not limited to, epidermal growth factor (EGF), neuronal growth factor (NGF), tumor necrosis factor (TNF), C5A, interleukin-8 (IL-8), monocyte chemotactic protein 1 (MIPla), monocyte chemoattractant protein 1 (MCP-1), platelet activating factor (PAF), N-Formyl-methionyl-leucyl- phenylalanine (FMLP), leukotriene $B_4$ ($LTB_4R$), gastrin releasing peptide (GRP), IgE, major histocompatibility protein (MHC), peptide, superantigen, antigen, vasopressin, thrombin, bradykinin and acetylcholine. In addition, the activity of an MEKK protein of the present invention is capable of being stimulated by compounds including phorbol esters such as TPA. A preferred MEKK protein is also capable of being stimulated by EGF, NGF and TNF (especially TNFα).

Preferably, the activity of an MEKK protein of the present invention is capable of being stimulated at least 2-fold over basal levels (i.e., levels found in nature when not stimulated), more preferably at least about 4-fold over basal levels and even more preferably at least about 6-fold over basal levels, when a cell producing the MEKK protein is contacted with EGF under the conditions described in related U.S. patent application Ser. No. 08/440,421, entitled "METHOD AND PRODUCT FOR REGULATING CELL RESPONSIVENESS TO EXTERNAL SIGNALS," filed May 15, 1995.

Similarly, the activity of an MEKK protein of the present invention is capable of being stimulated at least 1-fold over basal levels, more preferably at least about 2-fold over basal levels and even more preferably at least about 3-fold over basal levels by NGF stimulation, when a cell producing the.

MEKK protein is contacted with NGF under the conditions described in related U.S. patent application Ser. No. 08/440,421, entitled "METHOD AND PRODUCT FOR REGULATING CELL RESPONSIVENESS TO EXTERNAL SIGNALS," filed May 15, 1995.

Preferably, an MEKK protein of the present invention is capable of being stimulated at least 0.5-fold over basal levels, more preferably at least about 1-fold over basal levels and even more preferably at least about 2-fold over 5 basal levels by TPA stimulation when a cell producing the MEKK protein is contacted with TPA under the conditions described in related U.S. patent application Ser. No. 08/440,421, entitled "METHOD AND PRODUCT FOR REGULATING CELL RESPONSIVENESS TO EXTERNAL SIGNALS," filed May 15, 1995.

TNF is capable of regulating cell death and other functions in different cell types. The present inventor discovered that MEKK stimulation by TNF is independent of Raf.

Similarly, the present inventor is the first to appreciate that an MEKK protein can be directly stimulated by ultraviolet light (UV) damage of cells while a Raf-dependent pathway cannot. Therefore, both TNF and UV stimulate MEKK activity without substantially activating Raf. In addition, both UV and TNF activation of MEKK is Ras dependent.

Another aspect of the present invention is the recognition that an MEKK protein of the present invention is capable of regulating the apoptosis of a cell, an ability not shared by Raf protein. As used herein, apoptosis refers to the form of cell death that comprises: progressive contraction of cell volume with the preservation of the integrity of cytoplasmic organelles; condensation of chromatin, as viewed by light or electron microscopy; and DNA cleavage, as determined by centrifuged sedimentation assays. Cell death occurs when the membrane integrity of the cell is lost and cell lysis occurs. Apoptosis differs from necrosis in which cells swell and eventually rupture.

A preferred MEKK protein of the present invention is capable of inducing the apoptosis of cells, such that the cells have characteristics substantially similar to cytoplasmic shrinkage and/or nuclear condensation as described in related U.S. patent application Ser. No. 08/440,421, entitled "METHOD AND PRODUCT FOR REGULATING CELL RESPONSIVENESS TO EXTERNAL SIGNALS," filed May 15, 1995. Cells were microinjected with expression plasmids encoding MEKK protein. Injected cells were identified using anti-β-Gal antibody and the DNA of the cells were stained with propidium iodide. Cytoplasmic organization was monitored using an anti-tubulin antibody. The cells were then imaged by differential fluorescent imaging microscopy using techniques standard in the art. The cells demonstrated apoptosis by displaying a morphology having cytoplasmic shrinkage and nuclear condensation.

A schematic representation of the cell growth regulatory signal transduction pathway that is MEKK dependent. An MEKK protein of the present invention is capable of regulating the activity of JEK protein, JNK protein, Jun protein and/or ATF-2 protein, and Myc protein, such regulation being substantially, if not entirely, independent of Raf protein. Such Raf-independent regulation can regulate the growth characteristics of a cell, including the apoptosis of a cell. In addition, an MEKK protein of the present invention is capable of regulating the activity of MEK protein, which is also capable of being regulated by Raf protein. As such, an MEKK protein of the present invention is capable of regulating the activity of MAPK protein and members of the Ets family of transcription factors, such as TCF protein, also referred to as Elk-1 protein.

An MEKK protein of the present invention is capable of being activated by a variety of growth factors capable of activating Ras protein. In addition, an MEKK protein is capable of activating JNK protein which is also activated by Ras protein, but is not activated by Raf protein. As such, an MEKK protein of the present invention comprises a protein kinase at a divergence point in a signal transduction pathway initiated by different cell surface receptors. An MEKK protein is also capable of being regulated by TNF protein independent of Raf, thereby indicating an association of MEKK protein to a novel signal transduction pathway which is independent of Ras protein and Raf protein. Thus, an MEKK protein is capable of performing numerous unique functions independent of or by-passing Raf protein in one or more signal transduction pathways. An MEKK protein is capable of regulating the activity of MEK and/or JEK activity. As such, an MEKK protein is capable of regulating the activity of members of a signal transduction pathway that does not substantially include Raf activity. Such members include, but are not limited to, JNK, Jun, ATF and Myc protein. In addition, an MEKK protein is capable of regulating the members of a signal transduction pathway that does involve Raf, such members including, but are not limited to, MEK, MAPK and TCF. An MEKK protein of the present invention is thus capable of regulating the apoptosis of a cell independent of significant involvement by Raf protein.

In addition to the numerous functional characteristics of an MEKK protein, an MEKK protein of the present invention comprises numerous unique structural characteristics.

For example, in one embodiment, an MEKK protein of the present invention includes at least one of two different structural domains having particular functional characteristics. Such structural domains include an $NH_2$-terminal regulatory domain that serves to regulate a second structural domain comprising a COOH-terminal protein kinase catalytic domain that is capable of phosphorylating an MEK protein and/or JEK protein.

According to the present invention, an MEKK protein of the present invention includes a full-length MEKK protein, as well as at least a portion of an MEKK protein capable of performing at least one of the functions defined above. The phrase "at least a portion of an MEKK protein" refers to a portion of an MEKK protein encoded by a nucleic acid molecule that is capable of hybridizing, under stringent conditions, with a nucleic acid encoding a full-length MEKK protein of the present invention. Preferred portions of MEKK proteins are useful for regulating apoptosis in a cell. Additional preferred portions have activities useful for regulating MEKK kinase activity. Suitable sizes for portions of an MEKK protein of the present invention are as disclosed for MEKK protein homologues of the present invention.

In another embodiment, an MEKK protein of the present invention includes at least a portion of an MEKK protein having molecular weights ranging from about 70 kD to about 250 kD as determined by Tris-glycine SDS-PAGE, preferably using an 8% polyacrylamide SDS gel (SDS-PAGE) and resolved using methods standard in the art. A preferred MEKK protein has a molecular weight ranging from about 75 kD to about 225 kD and even more preferably from about 80 kD to about 200 kD.

In yet another embodiment, an MEKK protein of the present invention comprises at least a portion of an MEKK protein encoded by an MRNA (messenger ribonucleic acid) ranging from about 3.5 kb to about 12.0 kb, more preferably ranging from about 4.0 kb to about 11.0 kb, and even more preferably ranging from about 4.5 kb to about 10.0 kb. Particularly preferred MEKK proteins comprise at least a portion of an MEKK protein encoded by an mRNA having a size ranging from about 4.5 kb to about 5.0 kb, a size ranging from about 6.0 kb to about 6.5 ki, a size of about 7.0 kb, or a size ranging from about 8.0 kb to about 10.0 kb.

In another embodiment, an $NH_2$-terminal regulatory domain of the present invention includes an $NH_2$-terminal comprising about 400 amino acids having at least about 10% serine and/or threonine residues, more preferably about 400 amino acids having at least about 15% serine and/or threonine residues, and even more preferably about 400 amino acids having at least about 20% serine and/or threonine residues.

A preferred an $NH_2$-terminal regulatory domain of the present invention includes an $NH_2$-terminal comprising about 360 amino acids having at least about 10% serine and/or threonine residues, more preferably about 360 amino acids having at least about 15% serine and/or threonine residues, and even more preferably about 360 amino acids having at least about 20% serine and/or threonine residues.

Another preferred an $NH_2$-terminal regulatory domain of the present invention includes an $NH_2$-terminal comprising about 370 amino acids having at least about 10% serine and/or threonine residues, more preferably about 370 amino acids having at least about 15% serine and/or threonine residues, and even more preferably about 370 amino acids having at least about 20% serine and/or threonine residues.

In one embodiment, an MEKK protein of the present invention is devoid of SH2 and SH3 domains.

In another embodiment, an MEKK protein of the present invention includes at least a portion of an MEKK protein homologue preferably having at least about 50%, more preferably at least about 75%, and even more preferably at least about 85% amino acid homology (identity within comparable regions) with the kinase catalytic domain of a naturally occurring MEKK protein. Another MEKK protein of the present invention also includes at least a portion of an MEKK homologue of the present invention has at least about 10%, more preferably at least about 20%, and even more preferably at least about 30% amino acid homology with the $NH_2$-terminal regulatory domain of an MEKK protein of a naturally occurring MEKK protein.

The sequences comprising the catalytic domain of an MEKK protein are involved in phosphotransferase activity, and therefore display a relatively conserved amino acid sequence. The $NH_2$-terminal regulatory domain of an MEKK protein, however, can be substantially divergent. The lack of significant homology between MEKK protein $NH_2$-terminal regulatory domains is related to the regulation of each of such domains by different upstream regulatory proteins. For example, an MEKK protein can be regulated by the protein Ras, while others can be regulated independent of Ras. In addition, some MEKK proteins can be regulated by the growth factor TNFα, while others cannot. As such, the $NH_2$-terminal regulatory domain of an MEKK protein provides selectivity for upstream signal transduction regulation, while the catalytic domain provides for MEKK substrate selectivity function.

A preferred MEKK homologue has at least about 50%, more preferably at least about 75% and even more preferably at least about 85% amino acid homology with the kinase catalytic domain of an MEKK protein having an amino acid sequence as shown in sequence identification numbers disclosed in U.S. Pat. No. 5,405,941, PCT Patent Application No. 94/04178, and U.S. patent application Ser. Nos. 08/323,460 and 08/440,421. Such sequence listings are incorporated herein by this reference in their entirety. Another preferred MEKK homologue has at least about 10%, more preferably at least about 20% and even more preferably at least about 30% amino acid homology with the $NH_2$-terminal regulatory domain of an MEKK protein having the amino acid sequence shown in the sequence listings incorporated by reference herein.

In a preferred embodiment, an MEKK protein of the present invention includes at least a portion of an MEKK protein homologue of the present invention that is encoded by a nucleic acid molecule having at least about 50%, more preferably at least about 75%, and even more preferably at least about 85% homology with a nucleic acid molecule encoding the kinase catalytic domain of an MEKK protein. Another preferred MEKK protein homologue is encoded by a nucleic acid molecule having at least about 10%, more preferably at least about 20%, and even more preferably at least about 30% homology with a nucleic acid molecule encoding the NH2-terminal regulatory domain of an MEKK protein.

Still another preferred MEKK homologue is encoded by a nucleic acid molecule having at least about 50%, more preferably at least about 75% and even more preferably at least about 85% amino acid homology with the kinase catalytic domain of an MEKK protein encoded by the nucleic acid sequence shown in the sequence listings incorporated by reference herein. An MEKK homologue also includes those encoded by a nucleic acid molecule having at least about 10%, more preferably at least about 20% and even more preferably at least about 30% amino acid homology with the $NH_2$-terminal regulatory domain of an MEKK protein encoded by the nucleic acid sequence shown in the sequence listings incorporated by reference herein.

It should be noted that since nucleic acid and amino acid sequencing technology is not entirely error-free, the foregoing sequences, at best, represent apparent nucleic acid and amino acid sequences of an MEKK protein of the present invention.

According to the present invention, an MEKK protein of the present invention can include MEKK proteins that have undergone post-translational modification. Such modification can include, for example, glycosylation (e.g., including addition of N-linked and/or 0-linked oligosaccharides) or post-translational conformational changes or post-translational deletions.

Another embodiment of the present invention is an isolated nucleic acid molecule capable of hybridizing, under stringent conditions, with an MEKK protein gene encoding an MEKK protein of the present invention. In accordance with the present invention, an isolated nucleic acid molecule is a nucleic acid molecule that has been removed from its natural milieu (i.e., that has been subject to human manipulation). As such, "isolated" does not reflect the extent to which the nucleic acid molecule has been purified. An isolated nucleic acid molecule can include DNA, RNA, or derivatives of either DNA or RNA.

An isolated nucleic acid molecule of the present invention can be obtained from its natural source either as an entire (i.e., complete) gene or a portion thereof capable of forming a stable hybrid with that gene. As used herein, the phrase "at least a portion of" an entity refers to an amount of the entity that is at least sufficient to have the functional aspects of that entity. For example, at least a portion of a nucleic acid sequence, as used herein, is an amount of a nucleic acid sequence capable of forming a stable hybrid with a particular desired gene (e.g., MEKK genes) under stringent hybridization conditions. An isolated nucleic acid molecule of the present invention can also be produced using recombinant DNA technology (e.g., polymerase chain reaction (PCR) amplification, cloning) or chemical synthesis. Isolated MEKK protein nucleic acid molecules include natural nucleic acid molecules and homologues thereof, including, but not limited to, natural allelic variants and modified nucleic acid molecules in which nucleotides have been inserted, deleted, substituted, and/or inverted in such a manner that such modifications do not substantially interfere with the nucleic acid molecule's ability to encode an MEKK protein of the present invention or to form stable hybrids under stringent conditions with natural nucleic acid molecule isolates of MEKK.

Preferred modifications to an MEKK protein nucleic acid molecule of the present invention include truncating a full-length MEKK protein nucleic acid molecule by, for example: deleting at least a portion of an MEKK protein nucleic acid molecule encoding a regulatory domain to produce a constitutively active MEKK protein; deleting at least a portion of an MEKK protein nucleic acid molecule encoding a catalytic domain to produce an inactive MEKK protein; and modifying the MEKK protein to achieve desired inactivation and/or stimulation of the protein, for example, substituting a codon encoding a lysine residue in the catalytic domain (i.e., phosphotransferase domain) with a methionine residue to inactivate the catalytic domain.

A preferred truncated MEKK nucleic acid molecule encodes a form of an MEKK protein containing a catalytic domain but that lacks a regulatory domain. Preferred catalytic domain truncated MEKK nucleic acid molecules encode particular residues as disclosed in sequence identification numbers disclosed in U.S. Pat. No. 5,405,941, PCT Patent Application No. 94/04178, and U.S. patent application Ser. Nos. 08/323,460 and 08/440,421.

Another preferred truncated MEKK nucleic acid molecule encodes a form of an MEKK protein comprising an NH$_2$-terminal regulatory domain a catalytic domain but lacking a catalytic domain. Preferred regulatory domain truncated MEKK nucleic acid molecules encode particular residues as disclosed in sequence identification numbers disclosed in U.S. Pat. No. 5,405,941, PCT Patent Application No. 94/04178, and U.S. patent application Ser. Nos. 08/323,460 and 08/440,421.

An isolated nucleic acid molecule of the present invention can include a nucleic acid sequence that encodes at least one MEKK protein of the present invention, examples of such proteins being disclosed herein. Although the phrase "nucleic acid molecule" primarily refers to the physical nucleic acid molecule and the phrase "nucleic acid sequence" primarily refers to the sequence of nucleotides that comprise the nucleic acid molecule, the two phrases can be used interchangeably. As heretofore disclosed, MEKK proteins of the present invention include, but are not limited to, proteins having full-length MEKK protein coding regions, portions thereof, and other MEKK protein homologues.

As used herein, an MEKK protein gene includes all nucleic acid sequences related to a natural MEKK protein gene such as regulatory regions that control production of an MEKK protein encoded by that gene (including, but not limited to, transcription, translation or post-translation control regions) as well as the coding region itself. A nucleic acid molecule of the present invention can be an isolated natural MEKK protein nucleic acid molecule or a homologue thereof. A nucleic acid molecule of the present invention can include one or more regulatory regions, full-length or partial coding regions, or combinations thereof. The minimal size of an MEEK protein nucleic acid molecule of the present invention is the minimal size capable of forming a stable hybrid under stringent hybridization conditions with a corresponding natural gene.

An MEKK protein nucleic acid molecule homologue can be produced using a number of methods known to those skilled in the art (see, e.g., Sambrook et al., ibid.). For example, ucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologues can be selected from a mixture of modified nucleic acids by screening for the function of the protein encoded by the nucleic acid (e.g., the ability of a homologue to phosphorylate MEK protein or JEK protein) and/or by hybridization with isolated MEEK protein nucleic acids under stringent conditions.

One embodiment of the present invention is an MEKK protein nucleic acid molecule capable of encoding at least a portion of an MEKK protein, or a homologue thereof, as described herein. A preferred nucleic acid molecule of the present invention includes, but is not limited to, a nucleic acid molecule that encodes a protein having at least a portion of an amino acid sequence shown in the sequence listings incorporated by reference herein, or homologues thereof.

A preferred nucleic acid molecule of the present invention is capable of hybridizing under stringent conditions to a nucleic acid that encodes at least a portion of an MEKK protein, or a homologue thereof. Also preferred is an MEKK protein nucleic acid molecule that includes a nucleic acid sequence having at least about 50%, preferably at least about 75%, and more preferably at least about 85% homology with the corresponding region(s) of the nucleic acid sequence encoding the catalytic domain of an MEKK protein, or a homologue thereof. Also preferred is an MEKK protein nucleic acid molecule that includes a nucleic acid sequence having at least about 20%, preferably at least about 30%, and more preferably at least about 40% homology with the corresponding region(s) of the nucleic acid sequence encoding the NH$_2$-terminal regulatory domain of an MEKK protein, or a homologue thereof. A particularly preferred nucleic acid sequence is a nucleic acid sequence having at least about 50%, preferably at least about 75%, and more preferably at least about 85% homology with a nucleic acid sequence encoding the catalytic domain of an amino acid sequence shown in the sequence listings incorporated by reference herein. Another particularly preferred nucleic acid sequence is a nucleic acid sequence having at least about 20%, preferably at least about 30%, and more preferably at least about 40% homology with a nucleic acid sequence encoding the NH$_2$-terminal regulatory domain of the amino acid sequence shown in the sequence listings incorporated by reference herein, or homologues thereof.

Such nucleic acid molecules can be a full-length gene and/or a nucleic acid molecule encoding a full-length protein, a hybrid protein, a fusion protein, a multivalent protein or a truncation fragment. More preferred nucleic acid molecules of the present invention comprise isolated nucleic acid molecules having the nucleic acid sequence shown in the sequence listings incorporated by reference herein.

Knowing a nucleic acid molecule of an MEKK protein of the present invention allows one skilled in the art to make copies of that nucleic acid molecule as well as to obtain additional portions of MEKK protein-encoding genes (e.g., nucleic acid molecules that include the translation start site and/or transcription and/or translation control regions), and/or MEKK protein nucleic acid molecule homologues. Knowing a portion of an amino acid sequence of an MEKK protein of the present invention allows one skilled in the art to clone nucleic acid sequences encoding such an MEKK protein.

The present invention also includes nucleic acid molecules that are oligonucleotides capable of hybridizing, under stringent conditions, with complementary regions of other, preferably longer, nucleic acid molecules of the present invention that encode at least a portion of an MEKK protein, or a homologue thereof. A preferred oligonucleotide is capable of hybridizing, under stringent conditions, with a nucleic acid molecule that is capable of encoding at least a portion of the amino acid sequence shown in the sequence listings incorporated by reference herein, or homologues thereof. A more preferred oligonucleotide is capable of hybridizing to a nucleic acid molecule having the nucleic acid sequence shown in the sequence listings incorporated by reference herein, or complements thereof.

Oligonucleotides of the present invention can be RNA, DNA, or derivatives of either. The minimal size of such oligonucleotides is the size required to form a stable hybrid between a given oligonucleotide and the complementary sequence on another nucleic acid molecule of the present invention Minimal size characteristics are disclosed herein. The size of the oligonucleotide must also be sufficient for the use of the oligonucleotide in accordance with the present invention. oligonucleotides of the present invention can be used in a variety of applications including, but not limited to, as probes to identify additional nucleic acid molecules, as primers to amplify or extend nucleic acid molecules or in therapeutic applications to inhibit, for example, expression of MEKK proteins by cells. Such therapeutic applications include the use of such oligonucleotides in, for example, antisense-, triplex formation-, ribozyme- and/or RNA drug-based technologies. The present invention, therefore, includes use of such oligonucleotides and methods to interfere with the production of MEKK proteins.

In one embodiment, an isolated MEKK protein of the present invention is produced by culturing a cell capable of expressing the protein under conditions effective to produce the protein, and recovering the protein. A preferred cell to culture is a recombinant cell that is capable of expressing the MEKK protein, the recombinant cell being produced by transforming a host cell with one or more nucleic acid molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained.

The present invention also includes a recombinant vector which includes at least one MEKK protein nucleic acid molecule of the present invention inserted into any vector capable of delivering the nucleic acid molecule into a host cell. Such a vector contains heterologous nucleic acid sequences, for example nucleic acid sequences that are not naturally found adjacent to MEKK protein nucleic acid molecules of the present invention. The vector can be either RNA or DNA, and either prokaryotic or eukaryotic, and is typically a virus or a plasmid. Recombinant vectors can be used in the cloning, sequencing, and/or otherwise manipulating of MEKK protein nucleic acid molecules of the present invention. One type of recombinant vector, herein referred to as a recombinant molecule and described in more detail below, can be used in the expression of nucleic acid molecules of the present. invention. Preferred recombinant vectors are capable of replicating in the transformed cell.

Preferred nucleic acid molecules to insert into a recombinant vector includes a nucleic acid molecule that. encodes at least a portion of an MEKK protein, or a homologue thereof. A more preferred nucleic acid molecule to insert into a recombinant vector includes a nucleic acid molecule encoding at least a portion of the amino acid sequence shown in the sequence listings incorporated by reference herein, or homologues thereof. An even more preferred nucleic acid molecule to insert into a recombinant vector includes the nucleic acid molecule shown in the sequence listings incorporated by reference herien, or complements thereof.

Suitable host cells for transforming a cell can include any cell capable of producing MEKK proteins of the present invention after being transformed with at least one nucleic acid molecule of the present invention. Host cells can be either untransformed cells or cells that are already transformed with at least one nucleic acid molecule. Suitable host cells of the present invention can include bacterial, fungal (including yeast), insect, animal and plant cells. Preferred host cells include bacterial, yeast, insect and mammalian cells, with mammalian cells being particularly preferred.

A recombinant cell is preferably produced by transforming a host cell with one or more recombinant molecules, each comprising one or more nucleic acid molecules of the present invention operatively linked to an expression vector containing one or more transcription control sequences. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule.

Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, insect, animal, and/or plant cells. As such, nucleic acid molecules of the present invention can be operatively linked to expression vectors containing regulatory sequences such as promoters, operators, repressors, enhancers, termination sequences, origins of replication, and other regulatory sequences that are compatible with the recombinant cell and that control the expression of nucleic acid molecules of the present invention. As used herein, a transcription control sequence includes a sequence which is capable of controlling the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, and mammalian cells, such as, but not limited to, tac, lac, trp, trc, oxy-pro, omp/lpp, rrnB, bacteriophage lambda (λ) (such as λP$_L$ and λP$_R$ and fusions that include such promoters), bacteriophage T7, T7lac, bacteriophage T3, bacteriophage SP6, bacteriophage SPO1, metallothionein, alpha mating factor, baculovirus, vaccinia virus, herpesvirus, poxvirus, adenovirus, simian virus 40, retrovirus actin, retroviral long terminal repeat, Rous sarcoma virus, heat shock, phosphate and nitrate transcription control sequences, as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with a DNA sequence encoding an MEKK protein.

Preferred nucleic acid molecules for insertion into an expression vector include nucleic acid molecules that encode at least a portion of an MEKK protein, or a homologue thereof.

A more preferred nucleic acid molecule for insertion into an expression vector includes a nucleic acid molecule encoding at least a portion of the amino acid sequence shown in the sequence listings incorporated by reference herein, or homologues thereof.

Expression vectors of the present invention may also contain fusion sequences which lead to the expression of inserted nucleic acid molecules of the present invention as fusion proteins. Inclusion of a fusion sequence as part of an MEKK nucleic acid molecule of the present invention can enhance the stability during production, storage and/or use of the protein encoded by the nucleic acid molecule. Furthermore, a fusion segment can function as a tool to simplify purification of an MEKK protein, such as to enable purification of the resultant fusion protein using affinity chromatography. A suitable fusion segment can be a domain of any size that has the desired function (e.g., increased stability and/or purification tool). It is within the scope of the present invention to use one or more fusion segments. Fusion segments can be joined to amino and/or carboxyl termini of an MEKK protein. Linkages between fusion segments and MEKK proteins can be constructed to be susceptible to cleavage to enable straight-forward recovery of the MEKK proteins. Fusion proteins are preferably produced by culturing a recombinant cell transformed with a fusion nucleic acid sequence that encodes a protein including the fusion segment attached tc either the carboxyl and/or amino terminal end of an MEKK protein.

A recombinant cell of the present invention includes any cells transformed with at least one of any nucleic acid molecule of the present invention. A preferred recombinant cell is a cell transformed with at least one nucleic acid molecule that encodes at least a portion of an MEKK protein, or a homologue thereof. A more preferred recombinant cell is transformed with at least one nucleic acid molecule that is capable of encoding at least a portion of the amino acid sequence shown in the sequence listings incorporated by reference herein, or homologues thereof. An even more preferred recombinant cell is transformed with at least one nucleic acid molecule shown in the sequence listings incorporated by reference herein, or complements thereof. Particularly preferred recombinant cells include mammalian cells involved in a disease transformed with at least one of the aforementioned nucleic acid molecules. Methods to improve expression of transformed nucleic acid molecules are disclosed in U.S. Pat. No. 5,405,941, which is incorporated herein by this reference.

As used herein, amplifying the copy number of a nucleic acid sequence in a cell can be accomplished either by increasing the copy number of the nucleic acid sequence in the cell's genome or by introducing additional copies of the nucleic acid sequence into the cell by transformation. Copy number amplification is conducted in a manner such that greater amounts of enzyme are produced, leading to enhanced conversion of substrate to product. For example, recombinant molecules containing nucleic acids of the present invention can be transformed into cells to enhance enzyme synthesis. Transformation can be accomplished using any process by which nucleic acid sequences are inserted into a cell. Prior to transformation, the nucleic acid sequence on the recombinant molecule can be manipulated to encode an enzyme having a higher specific activity.

In accordance with the present invention, recombinant cells can be used to produce an MEKK protein of the present invention by culturing such cells under conditions effective to produce such a protein, and recovering the protein. Effective conditions to produce a protein include, but are not limited to, appropriate media, bioreactor, temperature, pH and oxygen conditions that permit protein production. An appropriate, or effective, medium refers to any medium in which a cell of the present invention, when cultured, is capable of producing an MEKK protein. Such a medium is typically an aqueous medium comprising assimilable carbohydrate, nitrogen and phosphate sources, as well as appropriate salts, minerals, metals and other nutrients, such as vitamins. The medium may comprise complex nutrients or may be a defined minimal medium.

Cells of the present invention can be cultured in conventional fermentation bioreactors, which include, but are, not limited to, batch, fed-batch, cell recycle, and continuous fermentors. Culturing can also be conducted in shake flasks, test tubes, microtiter dishes, and petri plates. Culturing is carried out at a temperature, pH and oxygen content appropriate for the recombinant cell. Such culturing conditions are well within the expertise of one of ordinary skill in the art.

Depending on the vector and host system used for production, resultant MEKK proteins may either remain within the recombinant cell or be secreted into the fermentation medium. The phrase "recovering the protein" refers simply to collecting the whole fermentation medium containing the protein and need not imply additional steps of separation or purification. MEKK proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, chromatofocusing and differential solubilization.

In addition, an MEKK protein of the present invention can be produced by isolating the MEKK protein from cells expressing the MEKK protein recovered from an animal. For example, a cell type, such as T cells, can be isolated from the thymus of an animal. MEKK protein can then be isolated from the isolated T cells using standard techniques described herein.

The present invention also includes a method to identify compounds capable of regulating signals initiated from a receptor on the surface of a cell, such signal regulation involving in some respect, MEKK protein. Such a method comprises the steps of: (a) contacting a cell containing an MEKK protein with a putative regulatory compound; (b) contacting the cell with a ligand capable of binding to a receptor on the surface of the cell; and (c) assessing the ability of the putative regulatory compound to regulate cellular signals by determining activation of a member of an MEKK-dependent pathway of the present invention. A preferred method to perform step (c) comprises measuring the phosphorylation of a member of an MEKK-dependent pathway. Such measurements can be performed using immunoassays having antibodies specific for phosphotyrosines, phosphoserines and/or phosphothreonines. Another preferred method to perform step (c) comprises measuring the ability of the MEKK protein to phosphorylate a substrate molecule comprising a protein including JEK, MEK1, MEK2, JNKK1, JNKK2, Raf-1, Ras-GAP and neurofibromin using methods described herein. Preferred substrates include JEK, MEK1, MEK2, JNKK1 and JNKK2. Yet another preferred method to perform step (c) comprises determining the ability of MEKK protein to bind to Ras protein. In particular, determining the ability of MEKK protein to bind to GST-Ras$^{V12}$(GTP$\lambda$S).

Putative compounds as referred to herein include, for example, compounds that are products of rational drug design, natural products and compounds having partially defined signal transduction regulatory properties. A putative compound can be a protein-based compound, a carbohydrate-based compound, a lipid-based compound, a nucleic acid-based compound, a natural organic compound, a synthetically derived organic compound, an anti-idiotypic antibody and/or catalytic antibody, or fragments thereof. A putative regulatory compound can be obtained, for example, from libraries of natural or synthetic compounds, in particular from chemical or combinatorial libraries (i.e., libraries of compounds that differ in sequence or size but that have the same building blocks; see for example, U.S. Pat. Nos. 5,010,175 and 5,266,684 of Rutter and Santi) or by rational drug design.

In another embodiment, a method to identify compounds capable of regulating signal transduction in a cell can comprise the steps of: (a) contacting a putative inhibitory compound with an MEKK protein to form a reaction mixture; (b) contacting the reaction mixture with MEK protein; and (c) assessing the ability of the putative inhibitory compound to inhibit phosphorylation of the NEK protein by the MEKK protein. The results obtained from step (c) can be compared with the ability of a putative inhibitory compound to inhibit the ability of Raf protein to phosphorylate MEK protein, to determine if the compound can selectively regulate signal transduction involving MEKK protein independent of Raf protein. MEKK, MEK and Raf proteins used in the foregoing methods can be recombinant proteins or naturally-derived proteins.

In another embodiment, a method to identify compounds capable of regulating signal transduction in a cell can comprise the steps of: (a) contacting a putative inhibitory compound with either an MEKK protein or a Ras protein, or functional equivalents thereof, to form a first reaction mixture; (b) combining the first reaction mixture with either Ras protein (or a functional equivalent thereof) if MEKK protein was used in the first reaction mixture, or MEKK protein (or a functional equivalent thereof) if Raf protein if MEKK protein was added to the first reaction mixture; and (c) assessing the ability of the putative inhibitory compound to inhibit the binding of the Ras protein to the MEKK protein. The lack of binding of the MEKK protein to the Ras protein indicates that the putative inhibitory compound is effective at inhibiting binding between MEKK and Ras. MEKK and Ras proteins used in the foregoing method can be recombinant proteins or naturally-derived proteins. Preferred Ras protein for use with the foregoing method includes, but is not limited to, GST-Ras$^{V12}$(GTPλS). Preferred MEKK protein for use with the method includes recombinant MEKK protein. More preferred MEKK protein includes at least a portion of an MEKK protein having the kinase domain of MEKK. Even more preferred MEKK protein includes a protein encoded by p-MEKK1, MEKK$_{COOH}$ and/or MEKK$_{COOH}$-His (as described in U.S. patent application Ser. No. 08/440,421.

The inhibition of binding of MEKK protein to Ras protein can be determined using a variety of methods known in the art. For example, immunoprecipitation assays can be performed to determine if MEKK and Ras co-precipitate. In addition, immunoblot assays can be performed to determine if MEKK and Ras co-migrate when resolved by gel electrophoresis. Another method to determine binding of MEKK to Ras comprises combining a substrate capable of being phosphorylated by MEKK protein with the Ras protein of the reaction mixture of step (b). In this method, Ras protein is separated from the reaction mixture of step (b) following incubation with MEKK protein. If MEKK protein is able to bind to the Ras, then the bound MEKK will be co-isolated with the Ras protein. The substrate is then added to the isolated Ras protein. Any co-isolated MEKK protein will phosphorylate the substrate. Thus, inhibition of binding between MEKK and Ras can be measured by determining the extent of phosphorylation of the substrate upon combination with the isolated Ras protein. The extent of phosphorylation can be determined using a variety of methods known in the art, including kinase assays using [λ$^{32}$P]ATP.

Moreover, one can determine whether the site of inhibitory action along a particular signal transduction pathway involves both Raf and MEKK proteins by carrying out experiments set forth above (i.e., see discussion on MEKK-dependent pathways).

Another aspect of the present invention includes a kit to identify compounds capable of regulating signals initiated from a receptor on the surface of a cell, such signals involving in some respect, MEKK protein. Such kits include: (a) at least one cell containing NEKK protein; (b) a ligand capable of binding to a receptor on the surface of the cell; and (c) a means for assessing the ability of a putative regulatory compound to alter phosphorylation of the MEKK protein. Such a means for detecting phosphorylation include methods and reagents known to those of skill in the art, for example, phosphorylation can be detected using antibodies specific for phosphorylated amino acid residues, such as tyrosine, serine and threonine. Using such a kit, one is, capable of determining, with a fair degree of specificity, the location along a signal transduction pathway of particular pathway constituents, as well as the identity of the constituents involved in such pathway, at or near the site of regulation.

In another embodiment, a kit of the present invention can includes: (a) MEKK protein; (b) MEK protein; and (c) a means for assessing the ability of a putative inhibitory compound to inhibit phosphorylation of the MEK protein by the MEKK protein. A kit of the present invention can further comprise Raf protein and a means for detecting the ability of a putative inhibitory compound to inhibit the ability of Raf protein to phosphorylate the MEK protein.

Another aspect of the present invention relates to the treatment of an animal having a medical disorder that is subject to regulation or cure by manipulating a signal transduction pathway in a cell involved in the disorder. Such medical disorders include disorders which result from abnormal cellular growth or abnormal production of secreted cellular products. In particular, such medical disorders include, but are not limited to, cancer, autoimmune disease, inflammatory responses, allergic responses and neuronal disorders, such as Parkinson's disease and Alzheimer's disease. Preferred cancers subject to treatment using a method of the present invention include, but are not limited to, small cell carcinomas, non-small cell lung carcinomas with overexpressed. EGF receptors, breast cancers with overexpressed EGF or Neu receptors, tumors having overexpressed growth factor receptors of established autocrine loops and tumors having overexpressed growth factor receptors of established paracrine loops. According to the present invention, the term treatment can refer to the regulation of the progression of a medical disorder or the complete removal of a medical disorder (e.g., cure). Treatment of a medical disorder can comprise regulating the signal transduction activity of a cell in such a manner that a cell involved in the medical disorder no longer responds to extracellular stimuli (e.g., growth factors or cytokines), or the killing of a cell involved in the medical disorder through cellular apoptosis.

One aspect of the present invention involves the recognition that an MEKK protein of the present invention is capable of regulating the homeostasis of a cell by regulating cellular activity such as cell growth cell death, and cell function (e.g., secretion of cellular products). Such regulation, in most cases, is independent of Raf, however, as discussed above, some pathways capable of regulation by MEKK protein may be subject to upstream regulation by Raf protein. Therefore, it is within the scope of the present invention to either stimulate or inhibit the activity of Raf protein and/or MEKK protein to achieve desired regulatory results. Without being bound by theory, it is believed that the regulation of Raf protein and MEKK protein activity at the divergence point from Ras protein can be controlled by a "2-hit" mechanism. For example, a first "hit" can comprise any means of stimulating Ras protein, thereby stimulating a Ras-dependent pathway, including, for example, contacting a cell with a growth factor which is capable of binding to a cell surface receptor in such a manner that Ras protein is activated. Following activation of Ras protein, a second "hit" can be delivered that is capable of increasing the activity of JNK activity compared with MAPK activity, or vice versa. A second "hit" can include, but is not limited to, regulation of JNK or MAPK activity by compounds capable of stimulating or inhibiting the activity of MEKK, JEK, Raf and/or MEK. For example, compounds such as protein kinase C or phospholipase C kinase, can provide the second "hit" needed to drive the divergent Ras-dependent pathway down the MEKK-dependent pathway in such a manner that JNK is preferentially activated over MAPK.

One embodiment of the present invention comprises a method for regulating the homeostasis of a cell comprising regulating the activity of an MEKK-dependent pathway relative to the activity of a Raf-dependent pathway in the cell. As used herein, the term "homeostasis" refers to the tendency of a cell to maintain a normal state using intracellular systems such as signal transduction pathways. Regulation of the activity of an MEKK-dependent pathway includes increasing the activity of an MEKK-dependent pathway relative to the activity of a Raf-dependent pathway by regulating the activity of a member of an MEKK-dependent pathway, a member of a Raf-dependent pathway, and combinations thereof, to achieve desired regulation of phosphorylation along a given pathway, and thus effect apoptosis. Preferred regulated members of an MEKK-dependent pathway or a Raf-dependent pathway to regulate include, but are not limited to, proteins including MEKK, Ras, Raf, JEK, MEK, MAPK, JNK, TCF, ATF-2, Jun and Myc, and combinations thereof.

In one embodiment, the activity of a member of an MEKK-dependent pathway, a member of a Raf-dependent pathway, and combinations thereof, are regulated by altering the concentration of such members in a cell. One preferred regulation scheme involves altering the concentration of proteins including MEKK, Ras, Raf, JEK, MEK, MAPK, JNK, TCF, Jun, ATF-2, and Myc, and combinations thereof. A more preferred regulation scheme involves increasing the concentration of proteins including MEKK, Ras, JEK, JNK, Jun, ATF-2, and Myc, and combinations thereof. Another more preferred regulation scheme involves decreasing the concentration of proteins including Raf, MEK, MAPK, and TCF, and combinations thereof. It is also within the scope of the present invention that the regulation of protein concentrations in two or more of the foregoing regulation schemes can be combined to achieve an optimal apoptotic effect in a cell.

A preferred method for increasing the concentration of a protein in a regulation scheme of the present invention includes, but is not limited to, increasing the copy number of a nucleic acid sequence encoding such protein within a cell, improving the efficiency with which the nucleic acid sequence encoding such protein is transcribed within a cell, improving the efficiency with which a transcript is translated into such a protein, improving the efficiency of post-translational modification of such protein, contacting cells capable of producing such protein with anti-sense nucleic acid sequences, and combinations thereof.

In a preferred embodiment of the present invention, the homeostasis of a cell is controlled by regulating the apoptosis of a cell. A suitable method for regulating the apoptosis of a cell is to regulate the activity of an MEKK- dependent pathway in which the MEKK protein regulates the pathway substantially independent of Raf. A particularly preferred method for regulating the apoptosis of a cell comprises increasing the concentration of MEKK protein by contacting a cell with a nucleic acid molecule encoding an MEKK protein that possesses unregulated kinase activity. A preferred nucleic acid molecule with which to contact a cell includes a nucleic acid molecule encoding the MEKK protein shown in the sequence listings incorporated by reference herein, and combinations thereof. A more preferred nucleic acid molecule with which to contact a cell includes a nucleic acid molecule encoding a truncated MEKK protein having only the kinase catalytic domain (i.e., no regulatory domain) of the MEKK protein shown in the sequence listings incorporated by reference herein. Again, suitable variation of an MEKK protein described herein comprises a protein encoded by a nucleic acid molecule that are able to hybridize to any of the above sequences under stringent conditions.

It is within the scope of the invention that the foregoing method can further comprise the step of decreasing the activity of MEK protein in the cell by contacting the cell with a compound capable of inhibiting MEK activity. Such compounds can include: peptides capable of binding to the kinase domain of MEK in such a manner that phosphorylation of MAPK protein by the MEK protein is inhibited; and/or peptides capable of binding to a portion of a MAPK protein in such a manner that phosphorylation of the MAPK protein is inhibited.

In another embodiment, the activity of a member of an MEKK-dependent pathway, a member of a Raf-dependent pathway, and combinations thereof, can be regulated by directly altering the activity of such members in a cell. A preferred method for altering the activity of a member of an MEKK-dependent pathway, includes, but is not limited to, contacting a cell with a compound capable of directly interacting with a protein including MEKK, Ras, JEK, JNK, Jun, ATF-2, and Myc, and combinations thereof, in such a manner that the proteins are activated; and/or contacting a cell with a compound capable of directly interacting with a protein including Raf, MEK, MAPK, TCF protein, and combinations thereof in such a manner that the activity of the proteins are inhibited. A preferred compound with which to contact a cell that is capable of regulating a member of an MEKK-dependent pathway includes a peptide capable of binding to the regulatory domain of proteins including MEKK, Ras, JEK, JNK, Jun, ATF-2, and Myc, in which the peptide inhibits the ability of the regulatory domain to regulate the activity of the kinase domains of such proteins. Another preferred compound with which to contact a cell includes TNFα, growth factors regulating tyrosine kinases, hormones regulating G protein-coupled receptors and FAS ligand.

A preferred compound with which to contact a cell that is capable of regulating a member of a Raf-dependent pathway includes a peptide capable of binding to the kinase catalytic domain of a protein selected from the group consisting of Raf, MEK-1, MEK-2, MAPK, and TCF, in which the peptide inhibits the ability of the protein to be phosphorylated or to phosphorylate a substrate.

In accordance with the present invention, a compound can regulate the activity of a member of an MEKK-dependent pathway by affecting the ability of one member of the pathway to bind to another member of the pathway. Inhibition of binding can be achieved by directly interfering at the binding site of either member, or altering the conformational structure, thereby precluding the binding between one member and another member.

Another preferred compound with which to contact a cell that is capable of regulating a member of an MEKK-dependent pathway includes an isolated compound that is capable of regulating the binding of MEKK protein to Ras protein (referred to herein as a Ras:MEKK binding compound). In one embodiment, a Ras:MEKK binding compound of the present invention comprises an isolated peptide (or mimetope thereof) comprising an amino acid sequence derived from a Ras protein. In another embodiment, a Ras:MEKK binding compound of the present invention comprises an isolated peptide (or mimetope thereof) comprising an amino acid sequence derived from an MEKK protein. According to the present invention, an isolated, or biologically pure, peptide, is a peptide that has been removed from its natural milieu. As such, "isolated" and "biologically pure" do not necessarily reflect the extent to which the protein has been purified. An isolated compound of the present invention can be obtained from a natural source or produced using recombinant DNA technology or chemical synthesis. As used herein, an isolated peptide can be a full-length protein or any homolog of such a protein in which amino acids have been deleted (e.g., a truncated version of the protein), inserted, inverted, substituted and/or derivatized (e.g., by glycosylation, phosphorylation, acetylation, myristylation, prenylation, palmitilation, and/or amidation) such that the peptide is capable of regulating the binding of Ras protein to MEKK protein.

In accordance with the present invention, a "mimetope" refers to any compound that is able to mimic the ability of an isolated compound of the present invention. A mimetope can be a peptide that has been modified to decrease its susceptibility to degradation but that still retain regulatory activity. Other examples of mimetopes include, but are not limited to, protein-based compounds, carbohydrate-based compounds, lipid-based compounds, nucleic acid-based compounds, natural organic compounds, synthetically derived organic compounds, anti-idiotypic antibodies and/or catalytic antibodies, or fragments thereof. A mimetope can be obtained by, for example, screening libraries of natural and synthetic compounds as disclosed herein that are capable of inhibiting the binding of Ras to MEKK. A mimetope can also be obtained by, for example, rational drug design. In a rational drug design procedure, the three-dimensional structure of a compound of the present invention can be analyzed by, for example, nuclear magnetic resonance (NMR) or x-ray crystallography. The three-dimensional structure can then be used to predict structures of potential mimetopes by, for example, computer modelling. The predicted mimetope structures can then be produced by, for example, chemical synthesis, recombinant DNA technology, or by isolating a mimetope from a natural source (e.g., plants, animals, bacteria and fungi).

In one embodiment, a Ras:MEKK binding compound of the present invention comprises an isolated peptide having a domain of a Ras protein that is capable of binding to an MEKK protein (i.e., that has an amino acid sequence which enables the peptide to be bound by an MEKK protein). A Ras peptide of the present invention is of a size that enables the peptide to be bound by an MEKK protein, preferably, at least about 4 amino acid residues, more preferably at least about 12 amino acid residues, and even more preferably at least about 25 amino acid residues. In particular, a Ras peptide of the present invention is capable of being bound by the COOH-terminal region of MEKK, preferably the region of MEKK containing the MEKK kinase domain. Preferably, a Ras peptide of the present invention comprises the effector domain of Ras and more preferably amino acid residues 17–42 of H-Ras.

In another embodiment, a Ras:MEKK binding compound of the present invention comprises an isolated MEKK peptide that has a domain of an MEKK protein that is capable of binding to a Ras protein (i.e., that has an amino acid sequence which enables the peptide to be bound by a Ras protein). An MEKK peptide of the present invention is of a size that enables the peptide to be bound by a Ras protein, in particular by the effector domain of a Ras protein. Preferably, an MEKK peptide of the present invention at least about 320 amino acids in length. Preferably, an MEKK peptide of the present invention comprises the COOH-terminal region of an MEKK protein and more preferably $MEKK_{COOH}$ (as described in U.S. patent application Ser. No. 08/440,421.

Ras is a critical component of tyrosine kinase growth factor receptor and G-protein coupled receptor regulation of signal transduction pathways controlling mitogenesis and differentiation. According to the present invention, the protein serine-threonine kinases Raf-1 and MEKK1 are Ras effectors and selectively bind to Ras in a GTP dependent manner. The p110 catalytic subunit of the lipid kinase has also been shown to directly interact with Ras in a GTP dependent manner. Ras-GAP and neurofibromin also regulate Ras GTPase activity. Raf-1, MEKK1 and PI3-kinase are capable of increasing the activity in cells expressing GTPase-deficient Ras consistent with their interaction with Ras-GTP being involved in their regulation.

Different functional domains of Ras effectors bind to Ras in a GTP dependent manner. The Ras binding domain for Raf-1 is encoded in the extreme $NH_2$-terminal regulatory domain of Raf-1. The Ras binding domain is encoded within the catalytic domain of MEKK1. Both Raf-1 and MEKK1 binding to Ras is blocked by a Ras effector domain peptide. Thus, Raf-1, MEKK1 and other Ras effectors can compete for interaction with Ras-GTP presumably at the Ras effector domain. The relative abundance and affinity of each Ras effector in different cells may influence the magnitude, onset and duration of each effector response. Secondary inputs, such as phosphorylation of the different Ras effectors, can also influence their interaction with Ras-GTP. The kinetic properties of Ras effector activation in cells relative to effector affinity for Ras-GTP are predictable based on the foregoing information. For example, MEKK1 can preferentially regulate the SEK/Jun kinase pathways relative to MAPK. Activation of the SEK/Jun kinase pathway is generally slower in onset and maintained as maximal activity longer than the activation of MAPK. As additional MEKKs are characterized it will be important to characterize their regulation and interaction with Ras-GTP. Undoubtedly additional Ras effectors will be identified in the near future.

The present invention also includes a method to administer isolated compounds of the present invention to a cell to regulate signal transduction activity in the cell. In particular, the present invention includes a method to administer an isolated compound of the present invention to a cell to regulate apoptosis of the cell.

The present invention also includes a method for regulating the homeostasis of a cell comprising injecting an area of a subject's body with an effective amount of a naked plasmid DNA compound (such as is taught, for example in Wolff et al., 1990, *Science* 247, 1465–1468). A naked plasmid DNA compound comprises a nucleic acid molecule encoding an MEKK protein of the present invention, operatively linked to a naked plasmid DNA vector capable of being taken up by and expressed in a recipient cell located in the body area. A preferred naked plasmid DNA compound of the present invention comprises a nucleic acid molecule encoding a truncated MEKK protein having deregulated kinase activity. Preferred naked plasmid DNA vectors of the present invention include those known in the art. When administered to a subject, a naked plasmid DNA compound of the present invention transforms cells within the subject and directs the production of at least a portion of an MEKK protein or RNA nucleic acid molecule that is capable of regulating the apoptosis of the cell.

A naked plasmid DNA compound of the present invention is capable of treating a subject suffering from a medical disorder including cancer, autoimmune disease, inflammatory responses, allergic responses and neuronal disorders, such as Parkinson's disease and Alzheimer's disease. For example, a naked plasmid DNA compound can be administered as an anti-tumor therapy by injecting an effective amount of the plasmid directly into a tumor so that the plasmid is taken up and expressed by a tumor cell, thereby killing the tumor cell. As used herein, an effective amount of a naked plasmid DNA to administer to a subject comprises an amount needed to regulate or cure a medical disorder the naked plasmid DNA is intended to treat, such mode of administration, number of doses and frequency of dose capable of being decided upon, in any given situation, by one of skill in the art without resorting to undue experimentation.

One aspect of the present invention relates to the recognition that an MEKK protein is capable of activating MAPK and that MAPK can regulate various cellular functions as disclosed in U.S. Pat. No. 5,405,941, which is incorporated herein by this reference.

An isolated compound of the present invention can be used to formulate a therapeutic composition. In one embodiment, a therapeutic composition of the present invention includes at least one isolated peptide of the present invention. A therapeutic composition of the present invention can further comprise suitable excipients. A therapeutic composition of the present invention can be formulated in an excipient that the subject to be treated can tolerate. Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful excipients include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, m-or o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In another embodiment, a therapeutic composition can also comprise a carrier. Carriers are typically compounds that increase the half-life of a therapeutic composition in the treated animal. Suitable carriers include, but are not limited to, liposomes, micelles, cells, polymeric controlled release formulations, biodegradable implants, bacteria, viruses, oils, esters, and glycols. Preferred carriers include liposomes and micelles.

A therapeutic composition of the present invention can be administered to any subject having a medical disorder as herein described. Acceptable protocols by which to administer therapeutic compounds of the present invention in an effective manner can vary according to individual dose size, number of doses, frequency of dose administration, and mode of administration. Determination of such protocols can be accomplished by those skilled in the art without resorting to undue experimentation. An effective dose refers to a dose capable of treating a subject for a medical disorder as described herein. Effective doses can vary depending upon, for example, the therapeutic composition used, the medical disorder being treated, and the size and type of the recipient animal. Effective doses to treat a subject include doses administered over time that are capable of regulating the activity, including growth, of cells involved in a medical disorder. For example, a first dose of a naked plasmid DNA compound of the present invention can comprise an amount of that causes a tumor to decrease in size by about 10% over 7 days when administered to a subject having a tumor. A second dose can comprise at least the same the same therapeutic compound than the first dose.

Another aspect of the present invention includes a method for prescribing treatment for subjects having a medical disorder as described herein. A preferred method for prescribing treatment comprises: (a) measuring the MEKK protein activity in a cell involved in the medical disorder to determine if the cell is susceptible to treatment using a method of the present invention; and (b) prescribing treatment comprising regulating the activity of an MEKK-dependent pathway relative to the activity of a Raf-dependent pathway in the cell to induce the apoptosis of the cell. The step of measuring MEKK protein activity can comprise: (1) removing a sample of cells from a subject; (2) stimulating the cells with a TNFα; and (3) detecting the state of phosphorylation of JEK protein using an immunoassay using antibodies specific for phosphothreonine and/or phosphoserine.

The present invention also includes antibodies capable of selectively binding to an MEKK protein of the present invention. Such an antibody is herein referred to as an anti-MEKK antibody. Polyclonal populations of anti-MEKK antibodies can be contained in an MEKK antiserum. MEKK antiserum can refer to affinity purified polyclonal antibodies, ammonium sulfate cut antiserum or whole antiserum. As used herein, the term "selectively binds to" refers to the ability of such an antibody to preferentially bind to MEKK proteins. Binding can be measured using a variety of methods known to those skilled in the art including immunoblot assays, immunoprecipitation assays, enzyme immunoassays (e.g., ELISA), radioimmunoassays, immunofluorescent antibody assays and immunoelectron microscopy; see, for example, Sambrook et al., *Molecular Cloning: A Laboratory Manual*, Cold Spring Harbor Labs Press, 1989.

Antibodies of the present invention can be either polyclonal or monoclonal antibodies and can be prepared using techniques standard in the art. Antibodies of the present invention include functional equivalents such as antibody fragments and genetically-engineered antibodies, including single chain antibodies, that are capable of selectively binding to at least one of the epitopes of the protein used to obtain the antibodies. Preferably, antibodies are raised in response to proteins that are encoded, at least in part, by a MEKK nucleic acid molecule. More preferably antibodies are raised in response to at least a portion of an MEKK protein, and even more preferably antibodies are raised in response to either the amino terminus or the carboxyl terminus of an MEKK protein. Preferably, an antibody of the present invention has a single site binding affinity of from about $10^3 M^{-1}$ to about $10^{12} M^{-1}$ for an MEKK protein of the present invention.

A preferred method to produce antibodies of the present invention includes administering to an animal an effective amount of an MEKK protein to produce the antibody and recovering the antibodies. Antibodies of the present invention have a variety of potential uses that are within the scope of the present invention. For example, such antibodies can be used to identify unique MEKK proteins and recover MEKK proteins.

Another aspect of the present invention comprises a therapeutic compound capable of regulating the activity of an MEKK-dependent pathway in a cell identified by a process, comprising: (a) contacting a cell with a putative regulatory molecule; and (b) determining the ability of the putative regulatory compound to regulate the activity of an MEKK-dependent pathway in the cell by measuring the activation of at least one member of said MEKK-dependent pathway. Preferred methods to measure the activation of a member of an MEKK-dependent pathway include measuring the transcription regulation activity of c-Myc protein, measuring the phosphorylation of a protein selected from the group consisting of MEKK, JEK, JNK, Jun, ATF-2, Myc, and combinations thereof.

Mitogen-activated protein kinase kinase (MEKK1) is a serine/threonine protein kinase that functions parallel to Raf-1 in the regulation of sequential protein kinase pathways that involve both mitogen-activated and stress-activated protein kinases. In this study, we examined the interaction of MEKK1 with 14-3-3 proteins. The T cell 14-3-3 isoform, but not the β and stratifin isoforms, interacted with MEKK1 in the two-hybrid system. We also prepared GST fusion proteins of the T cell, β, and stratifin 14-3-3 isoforms to further characterize the domains of MEKK1 and Raf-1 that interact with these proteins. We demonstrate that the T cell and β 14-3-3 isoform, but not stratifin, interact with COS cell-expressed MEKK1. Furthermore, the amino-terminal moiety, but not the carboxyl-terminal moiety, of expressed MEKK1 interacts with the GST•14-3-3 although the interaction is best when holoMEKK1 is expressed. In contrast, GST•14-3-3 proteins interact with both the amino- and carboxyl-regions of COS cell-expressed Raf-1 protein. Thus, although MEKK1 and Raf-1 function at a parallel point in the sequential protein kinase pathways, the interaction of 14-3-3 proteins with these kinases is not identical, suggesting a differential regulation between Raf-1 and MEKK1-stimulated pathways.

Examples related to the present invention are incorporated by this reference in their entirety as taught in U.S. Pat. No. 5,405,941 PCT Patent Application No. 94/04178, and U.S. patent application Ser. Nos. 08/323,460 and 08/440,421.

The foregoing description of the invention has been presented for purposes of illustration and description. Further, the description is not intended to limit the invention to the form disclosed herein. Consequently, variations and modifications commensurate with the above teachings, and the skill or knowledge in the relevant art are within the scope of the present invention. The preferred embodiment described herein above is further intended to explain the best mode known of practicing the invention and to enable others skilled in the art to utilize the invention in various embodiments and with various modifications required by their particular applications or uses of the invention. It is intended that the appended claims be construed to include alternate embodiments to the extent permitted by the prior art.

What is claimed:

1. An assay for identifying compounds which regulate signal transduction by a mitogen ERK kinase kinase (MEKK), comprising:

(a) providing a reaction mixture comprising a mammalian MEKK polypeptide;

(b) contacting the reaction mixture with a test compound; and (c) determining the effect of the test compound on an indicator of signal transduction by the mammalian MEKK polypeptide in the reaction mixture to thereby identify a compound which regulates signal transduction by an MEKK.

2. The assay of claim 1, wherein the mammalian MEKK polypeptide comprises an amino acid sequence having at least 75% identity with a kinase catalytic domain of an MEKK polypeptide selected from the group consisting of SEQ ID NO:2, SEQ ID NO:4, SEQ ID NO:6, SEQ ID NO:8, SEQ ID NO:10, and SEQ ID NO:12.

3. The assay of claim 1, wherein the mammalian MEKK polypeptide comprises an amino acid sequence having at least 85% identity with a kinase catalytic domain of an MEKK polypeptide selected from the group consisting of SEQ ID NO:2, SEQ ID NO:4, SEQ ID NO:6, SEQ ID NO:8, SEQ ID NO:10, and SEQ ID NO:12.

4. The assay of claim 1, wherein the mammalian MEKK polypeptide comprises an amino acid sequence having at least 75% identity with a regulatory domain of an MEKK polypeptide selected from the group consisting of SEQ ID NO:2, SEQ ID NO:4, SEQ ID NO:6, SEQ ID NO:8, SEQ ID NO:10, and SEQ ID NO:12.

5. The assay of claim 1, wherein the mammalian MEKK polypeptide comprises an amino acid sequence having at least 85% identity with a regulatory domain of an MEKK polypeptide selected from the group consisting of SEQ ID NO:2, SEQ ID NO:4, SEQ ID NO:6, SEQ ID NO:8, SEQ ID NO:10, and SEQ ID NO:12.

6. The assay of claim 1, wherein the mammalian MEKK polypeptide is encoded by a nucleic acid molecule which hybridizes under highly stringent conditions with a nucleic acid molecule selected from the group consisting of SEQ ID NO:1, SEQ ID NO:3, SEQ ID NO:5, SEQ ID NO:7, SEQ ID NO:9, and SEQ ID NO:11.

7. An assay for identifying compounds having potential to regulate signal transduction by a mitogen ERK kinase kinase (MEKK), comprising:

(a) providing a reaction mixture comprising a mammalian MEKK polypeptide, wherein the reaction mixture is a cell or a cell-free mixture;

(b) contacting the reaction mixture with a test compound; and (c) determining the effect of the test compound on an indicator of signal transduction by the mammalian MEKK polypeptide in the reaction mixture, wherein the indicator is interaction of the mammalian MEKK polypeptide with an MEKK interactor molecule or activity of a signaling pathway, to thereby identify a compound having potential to regulate signal transduction by an MEKK.

8. The assay of claim 1, wherein:

the reaction mixture comprises:

(i) a mammalian MEKK polypeptide, (ii) an MEKK interactor molecule which binds to the mammalian MEKK polypeptide, and (iii) a test compound; and the effect of the test compound on an indicator of signal transduction by the mammalian MEKK polypeptide in the reaction mixture is determined by:

detecting interaction of the mammalian MEKK polypeptide with the MEKK interactor molecule, wherein a change in the level of interaction of the mammalian MEKK polypeptide and MEKK interactor molecule in the presence of the test compound, relative to the level of interaction in the absence of the test compound, indicates that the test compound has the potential to regulate signal transduction by an MEKK.

9. The assay of claim 8, wherein the reaction mixture is a cell-free mixture.

10. The assay of claim 8, wherein the reaction mixture is a recombinant cell.

11. The assay of claim 8, wherein the MEKK interactor molecule is a polypeptide which specifically binds to the mammalian MEKK polypeptide.

12. The assay of any of claims 8, 9, or 10, wherein the mammalian MEKK polypeptide is a recombinant polypeptide.

13. The assay of claim 8, wherein the mammalian MEKK polypeptide includes a polypeptide sequence of an MEKK selected from the group consisting of SEQ ID NO:2, SEQ ID NO:4, SEQ ID NO:6, SEQ ID NO:8, SEQ ID NO:10, SEQ ID NO:12.

14. The assay of any of claims 8, 9 or 10, wherein the step of detecting the interaction of the mammalian MEKK polypeptide with the MEKK interactor molecule includes detecting an enzymatic activity of the mammalian MEKK polypeptide.

15. The assay of any of claims 8, 9 or 10 wherein the step of detecting the interaction of the MEKK interactor molecule with the mammalian MEKK polypeptide comprises detecting, in the reaction mixture, the formation of complexes ("MEKK complexes") including the MEKK interactor molecule and the mammalian MEKK polypeptide.

16. The assay of claim 15, wherein at least one of the mammalian MEKK polypeptide and the MEKK interactor molecule comprises a detectable label, and the level of MEKK complexes formed in the test mixture is quantitated by detecting the label in at least one of the MEKK interactor molecule, the mammalian MEKK polypeptide, and the MEKK complexes.

17. The assay of any of claims 8, 9 or 10, wherein the step of detecting the interaction of the MEKK interactor molecule with the mammalian MEKK polypeptide comprises an immunoassay.

18. The assay of claim 10, wherein the step of detecting the interaction of the MEKK interactor molecule with the mammalian MEKK polypeptide comprises detecting an intracellular signal produced in a signal transduction pathway involving the mammalian MEKK polypeptide.

19. The assay of claim 18, wherein the recombinant cell includes a reporter gene sensitive to MEKK signal transduction.

20. The assay of claim 10, wherein the ability of the test compound to regulate apoptosis of acell is measured.

21. The assay of claim 9, wherein the mammalian MEKK polypeptide is provided as a purified protein.

22. The assay of claim 9, wherein the mammalian MEKK polypeptide is provided as a cell lysate.

23. The assay of claim 8, wherein the MEKK intetactor molecule comprises Ras or a portion thereof.

24. The assay of claim 8, wherein the MEKKF interactor molecule is selected from the group comprising MEK1, MEK2, MKK1, MKK2, MKK3, MKK4, JNKK1, JNKK2, SEK1, SEK2.

25. The assay of claim 10, wherein the recombinant cell includes a heterologous nucleic acid encoding the mammalian MEKK polypeptide.

26. The assay of claim 10, wherein the recombinant cell includes a reporter gene construct comprising a reporter gene in operable linkage with a transcriptional regulatory sequence sensitive to intracellular signals transduced by interaction of the mammalian MEKK polypeptide and the MEKK interactor molecule.

27. The assay of claim 8, wherein the test compound is selected from the group consisting of: protein based, carbohydrate based, lipid based, nucleic acid based, natural organic based, synthetically derived organic based, and antibody based compounds.

28. The assay of claim 8, further comprising the step of preparing a therapeutic composition of a test compound identified in said assay.

29. The assay of claim 8, wherein the test compound is an inhibitor of the interaction between the MEKK interactor molecule and the mammalian MEKK polypeptide.

30. The assay of claim 8, wherein the test compound is a potentiator of the interaction between the MEKK interactor molecule and the mammalian MEKK polypeptide.

* * * * *

UNITED STATES PATENT AND TRADEMARK OFFICE
CERTIFICATE OF CORRECTION

PATENT NO. : 5,753,446
DATED : May 19, 1998
INVENTOR(S) : Gary L. Johnson

It is certified that error appears in the above-identified patent and that said Letters Patent is hereby corrected as shown below:

In claim 20, line 2, please delete "acell" and insert -- a cell--.

In claim 23, line 1, please delete "intetactor" and insert --interactor--.

In claim 24, line 1, please delete "MEKKF" and insert --MEKK--.

Signed and Sealed this

Twentieth Day of July, 1999

Attest:

Attesting Officer

Q. TODD DICKINSON

Acting Commissioner of Patents and Trademarks